(12) United States Patent
Seybold et al.

(10) Patent No.: US 10,653,513 B2
(45) Date of Patent: May 19, 2020

(54) BARORECEPTOR TESTING PRIOR TO IMPLANTATION METHODS AND APPARATUS

(71) Applicant: Vascular Dynamics, Inc., Mountain View, CA (US)

(72) Inventors: Brent Seybold, Santa Clara, CA (US); Christopher Ken, San Mateo, CA (US); Jennifer Gong, San Jose, CA (US); Suji Shetty, San Jose, CA (US); Robert Stern, Los Altos, CA (US); Edmund Roschak, Coto de Caza, CA (US)

(73) Assignee: Vascular Dynamics, Inc., Mountain View, CA (US)

( * ) Notice: Subject to any disclaimer, the term of this patent is extended or adjusted under 35 U.S.C. 154(b) by 148 days.

(21) Appl. No.: 15/901,790

(22) Filed: Feb. 21, 2018

(65) Prior Publication Data

US 2018/0235745 A1 Aug. 23, 2018

Related U.S. Application Data

(60) Provisional application No. 62/461,394, filed on Feb. 21, 2017.

(51) Int. Cl.
*A61F 2/06* (2013.01)
*A61B 5/00* (2006.01)
(Continued)

(52) U.S. Cl.
CPC .............. *A61F 2/06* (2013.01); *A61B 5/0205* (2013.01); *A61B 5/4047* (2013.01); *A61B 34/10* (2016.02);
(Continued)

(58) Field of Classification Search
CPC ...... A61F 2/06; A61F 2/82; A61F 2/91; A61F 2/885; A61B 5/0215
(Continued)

(56) References Cited

U.S. PATENT DOCUMENTS 5,707,400 A 1/1998 Terry, Jr. et al.
6,050,952 A 4/2000 Hakki et al.
(Continued)

FOREIGN PATENT DOCUMENTS

EP 1962949 A1 9/2008
EP 2026695 A2 2/2009
(Continued)

OTHER PUBLICATIONS

"International Search Report and Written Opinion dated Jun. 25, 2018 for International PCT Patent Application No. PCT/US18/19037".

*Primary Examiner* — Suzette J Gherbi
(74) *Attorney, Agent, or Firm* — Wilson Sonsini Goodrich and Rosati, P.C.

(57) ABSTRACT

Systems and methods for screening a subject for a therapy are described. A mechanical stimulation device positioned near at target location of a blood vessel to provide a mechanical stimulus to the blood vessel. The mechanical stimulus increases strain in one or more regions of the blood vessel, such as by modifying the cross-sectional geometry and/or area of the blood vessel to have different regions of different curvature A baroreflex or related physiological response in response to the mechanical stimulation is detected. In response to the detected response, it is determined whether the subject is appropriate for the therapy and/or which of a plurality of implants with different geometries and/or cross-sectional areas is most optimally suited for deployment in the subject.

30 Claims, 38 Drawing Sheets

(51) Int. Cl.
    *A61B 34/10*             (2016.01)
    *A61F 2/856*           (2013.01)
    *A61F 2/90*             (2013.01)
    *A61F 2/95*             (2013.01)
    *A61F 2/89*             (2013.01)
    *A61F 2/915*           (2013.01)
    *A61B 5/0205*         (2006.01)
    *A61B 90/00*           (2016.01)

(52) U.S. Cl.
    CPC ................ *A61F 2/856* (2013.01); *A61F 2/89* (2013.01); *A61F 2/90* (2013.01); *A61F 2/915* (2013.01); *A61F 2/95* (2013.01); *A61B 5/0053* (2013.01); *A61B 2034/108* (2016.02); *A61B 2090/3966* (2016.02); *A61F 2002/068* (2013.01)

(58) Field of Classification Search
    USPC ............................................... 623/1.15–1.48
    See application file for complete search history.

(56) References Cited

U.S. PATENT DOCUMENTS

| | | | |
|---|---|---|---|
| 6,073,048 A | 6/2000 | Kieval et al. | |
| 6,375,666 B1 | 4/2002 | Mische | |
| 6,764,498 B2 | 7/2004 | Mische | |
| 6,850,801 B2 | 2/2005 | Kieval et al. | |
| 6,985,774 B2 | 1/2006 | Kieval et al. | |
| 7,300,449 B2 | 11/2007 | Mische | |
| 7,499,747 B2 | 3/2009 | Kieval et al. | |
| 7,643,875 B2 | 1/2010 | Heil et al. | |
| 7,647,114 B2 | 1/2010 | Libbus | |
| 7,869,881 B2 | 1/2011 | Libbus et al. | |
| 8,175,712 B2 | 5/2012 | Tang et al. | |
| 8,195,289 B2 | 6/2012 | Heil, Jr. et al. | |
| 8,209,033 B2 | 6/2012 | Zhang et al. | |
| 8,321,024 B2 | 11/2012 | Georgakopoulos et al. | |
| 8,326,430 B2 | 12/2012 | Gerogakopoulos et al. | |
| 8,594,794 B2 | 11/2013 | Kieval et al. | |
| 8,600,511 B2 | 12/2013 | Yared et al. | |
| 8,620,422 B2 | 12/2013 | Kieval et al. | |
| 8,744,586 B2 | 6/2014 | Georgakopoulos et al. | |
| 8,755,907 B2 | 6/2014 | Kieval et al. | |
| 8,788,066 B2 | 7/2014 | Cates et al. | |
| 8,874,211 B2 | 10/2014 | Libbus et al. | |
| 8,923,972 B2 | 12/2014 | Gross | |
| 9,011,355 B2 | 4/2015 | Ehrenreich et al. | |
| 9,125,567 B2 | 9/2015 | Gross et al. | |
| 9,125,732 B2 | 9/2015 | Gross et al. | |
| 9,199,082 B1 | 12/2015 | Yared et al. | |
| 9,265,948 B2 | 2/2016 | Libbus et al. | |
| 9,271,825 B2 | 3/2016 | Arkusz et al. | |
| 9,457,174 B2 | 10/2016 | Gross | |
| 9,550,048 B2 | 1/2017 | Gross | |
| 9,592,136 B2 | 3/2017 | Gross et al. | |
| 9,642,726 B2 | 5/2017 | Gross et al. | |
| 9,999,532 B2 | 6/2018 | Mische | |
| 10,279,184 B2 * | 5/2019 | Pierce .................. | A61B 5/0215 |
| 2002/0065530 A1 | 5/2002 | Mische | |
| 2005/0015129 A1 | 1/2005 | Mische | |
| 2005/0027346 A1 | 2/2005 | Arkusz et al. | |
| 2006/0253193 A1 | 11/2006 | Lichtenstein et al. | |
| 2006/0259119 A1 * | 11/2006 | Rucker .................. | A61F 2/82 623/1.11 |
| 2007/0129746 A1 | 6/2007 | Mische | |
| 2007/0135845 A1 | 6/2007 | Mische et al. | |
| 2007/0142879 A1 | 6/2007 | Greenberg et al. | |
| 2007/0287879 A1 | 12/2007 | Gelbart et al. | |
| 2008/0077174 A1 | 3/2008 | Mische | |
| 2008/0161865 A1 | 7/2008 | Hagen | |
| 2008/0288030 A1 | 11/2008 | Zhang et al. | |
| 2010/0004714 A1 | 1/2010 | Georgakopoulos et al. | |
| 2011/0077729 A1 | 3/2011 | Gross et al. | |
| 2012/0095523 A1 | 4/2012 | Yared | |
| 2013/0030309 A1 | 1/2013 | Yared et al. | |
| 2013/0090703 A1 | 4/2013 | Georgakopoulos et al. | |
| 2013/0178750 A1 | 7/2013 | Sheehan et al. | |
| 2013/0304102 A1 * | 11/2013 | Gross .................. | A61B 17/12 606/158 |
| 2014/0343590 A1 | 11/2014 | Solem et al. | |
| 2015/0366467 A1 * | 12/2015 | De Kock ............... | A61B 5/021 600/377 |
| 2016/0038317 A1 * | 2/2016 | Yeh ........ | A61F 2/915 623/1.2 |
| 2016/0058989 A1 | 3/2016 | Gross et al. | |
| 2016/0158051 A1 | 6/2016 | Mische | |
| 2016/0303381 A1 * | 10/2016 | Pierce .................. | A61B 5/0215 |
| 2016/0324443 A1 * | 11/2016 | Rowland ............... | A61B 5/076 |
| 2017/0135829 A1 * | 5/2017 | Gross ........................ | A61F 2/82 |
| 2017/0196713 A1 | 7/2017 | Gross et al. | |
| 2018/0008279 A1 | 1/2018 | Celermajer et al. | |
| 2018/0028817 A1 * | 2/2018 | Libbus ............... | A61N 1/36146 |
| 2018/0214157 A1 | 8/2018 | Celermajer et al. | |
| 2018/0303648 A1 | 10/2018 | Mische | |
| 2019/0224484 A1 * | 7/2019 | Pierce .................. | A61B 5/0215 |
| 2019/0247306 A1 * | 8/2019 | Cleek .................. | A61K 9/0024 |

FOREIGN PATENT DOCUMENTS

| | | |
|---|---|---|
| EP | 2155052 A2 | 2/2010 |
| EP | 2214777 A1 | 8/2010 |
| EP | 2661217 A2 | 11/2013 |
| EP | 2755608 A1 | 7/2014 |
| WO | WO-2007013065 A2 | 2/2007 |
| WO | WO-2007075593 A1 | 7/2007 |
| WO | WO-2007146360 A3 | 4/2008 |
| WO | WO-2008083120 A2 | 7/2008 |
| WO | WO-2008143832 A2 | 11/2008 |
| WO | WO-2009048378 A1 | 4/2009 |
| WO | WO-2010035271 A1 | 4/2010 |
| WO | WO-2011138780 A2 | 11/2011 |
| WO | WO-2012094613 A2 | 7/2012 |
| WO | WO-2013038013 A1 | 3/2013 |
| WO | WO-2013096548 A1 | 6/2013 |
| WO | WO-2013169995 A1 | 11/2013 |
| WO | WO-2014186107 A1 | 11/2014 |
| WO | WO-2015088972 A1 | 6/2015 |
| WO | WO-2015167194 A1 | 11/2015 |
| WO | WO-2017024357 A1 | 2/2017 |

* cited by examiner

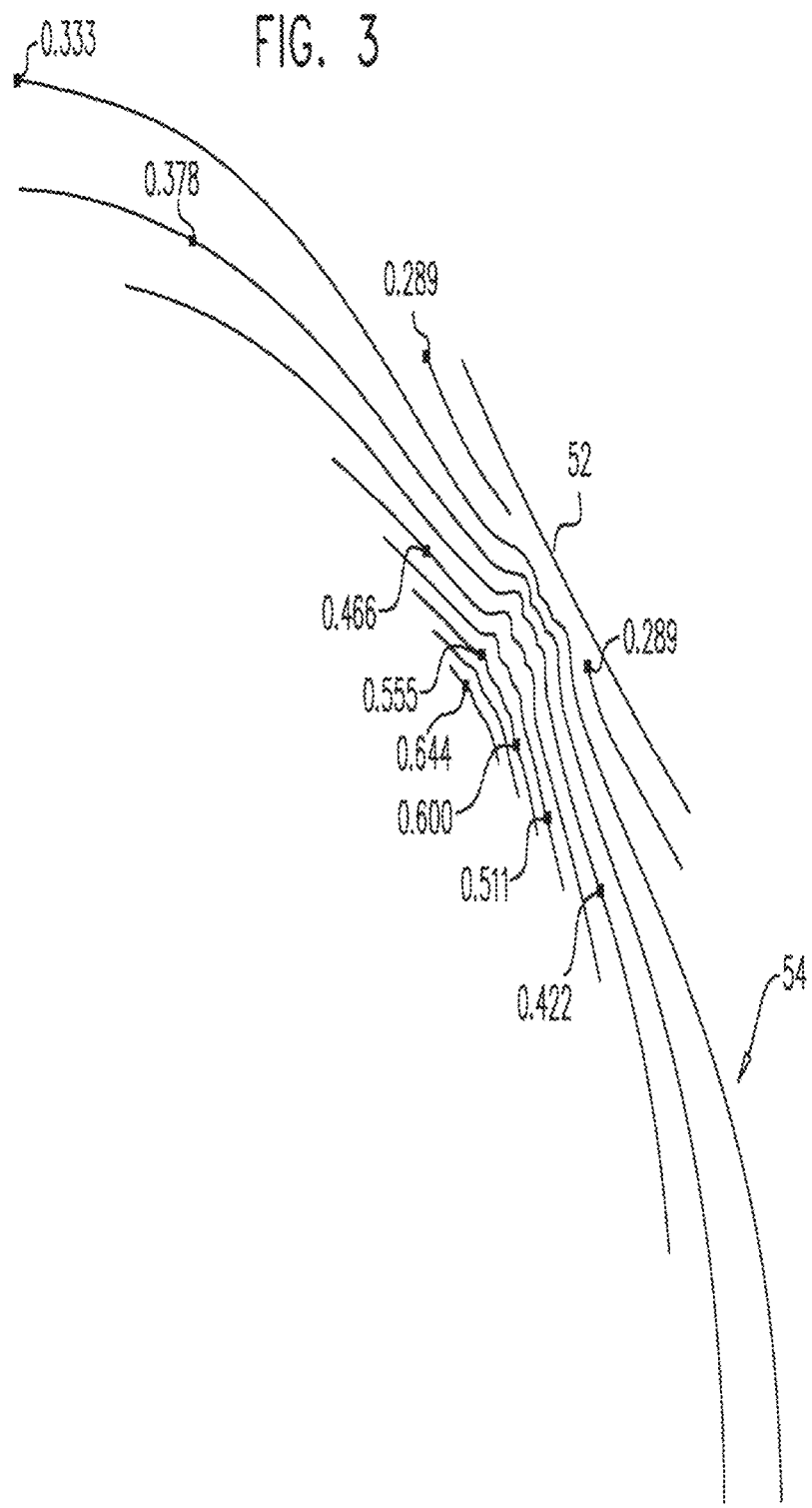

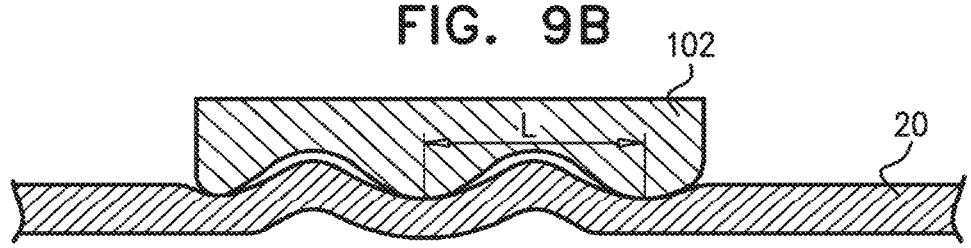
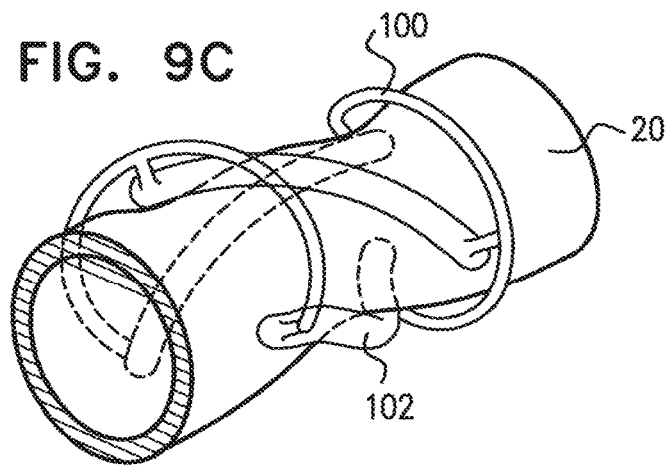
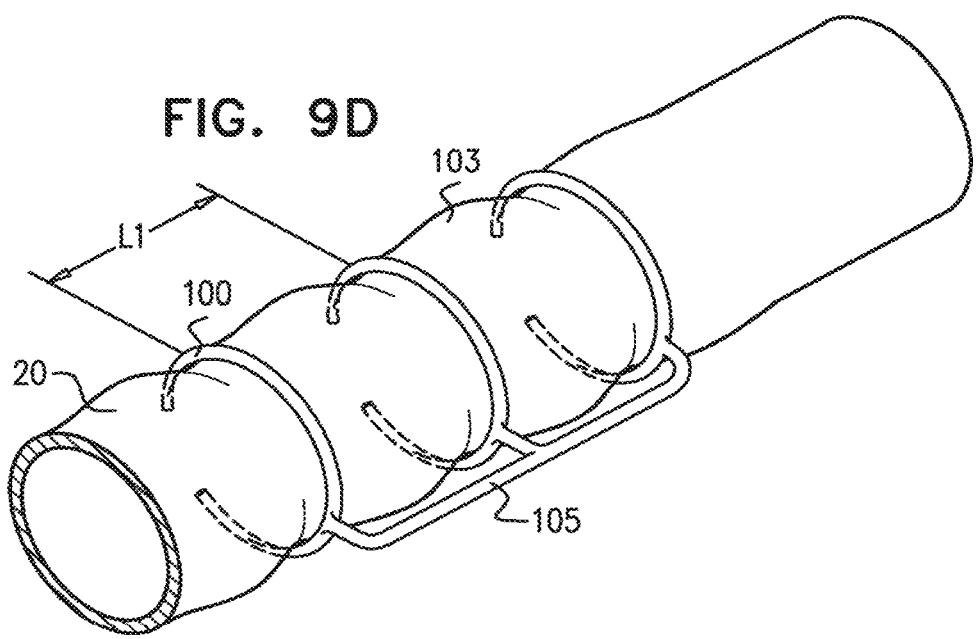

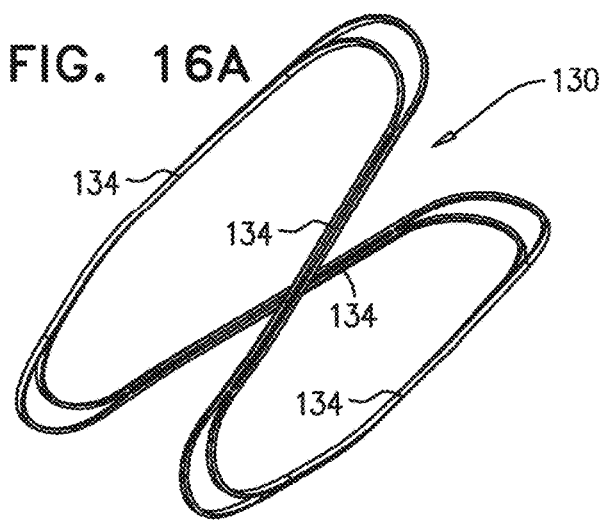
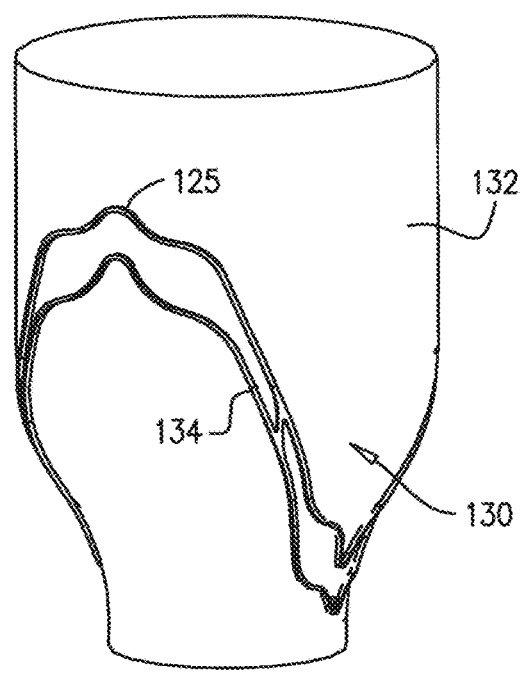
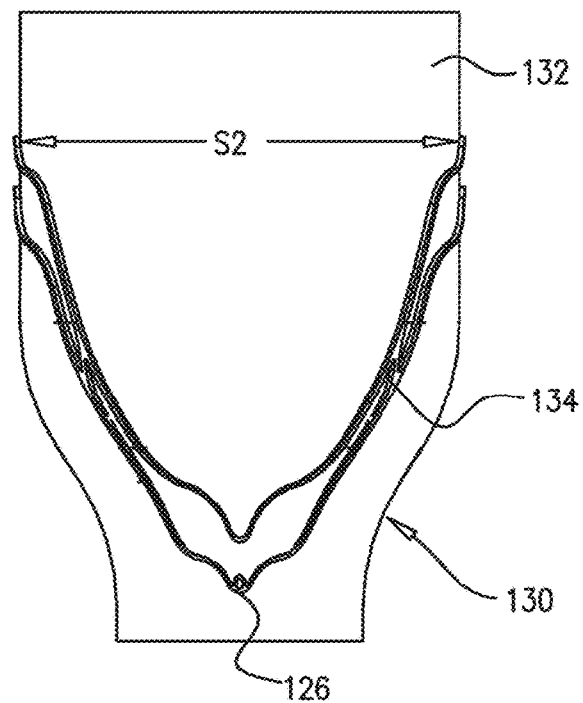
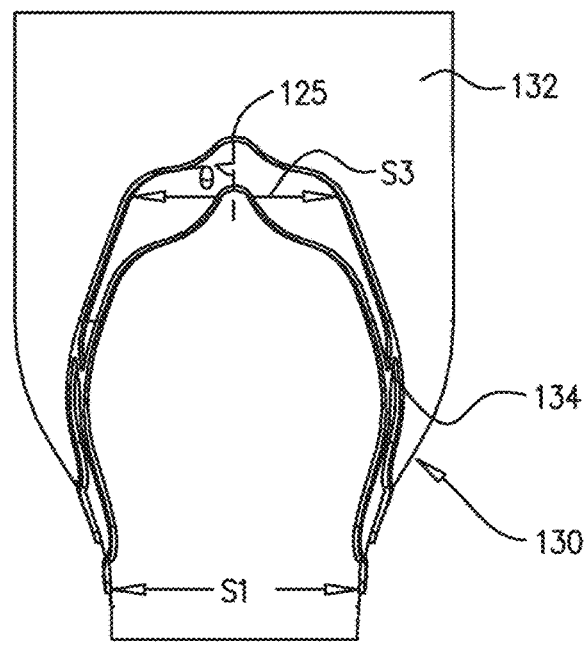

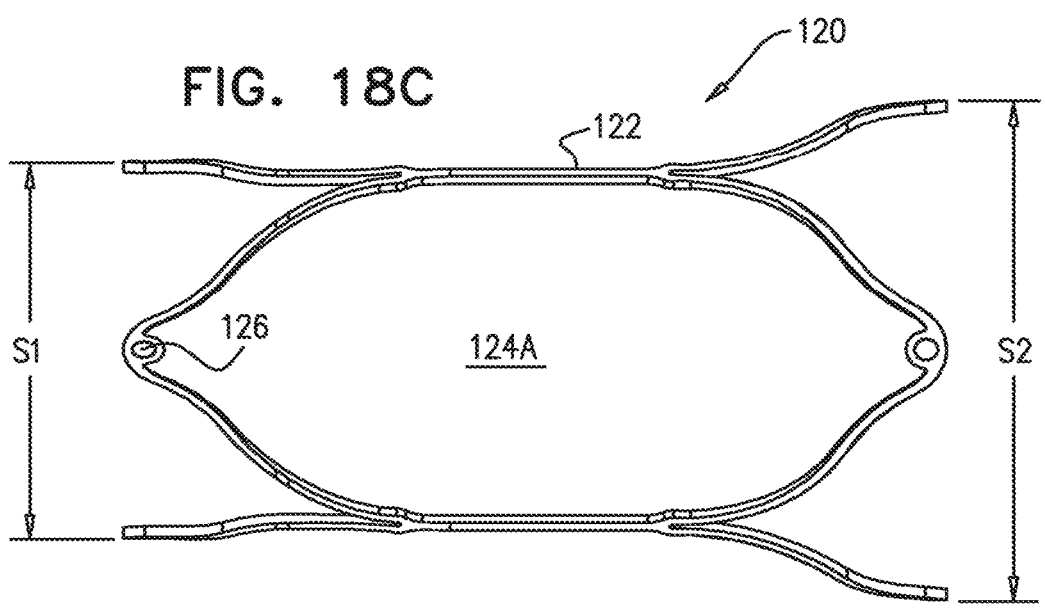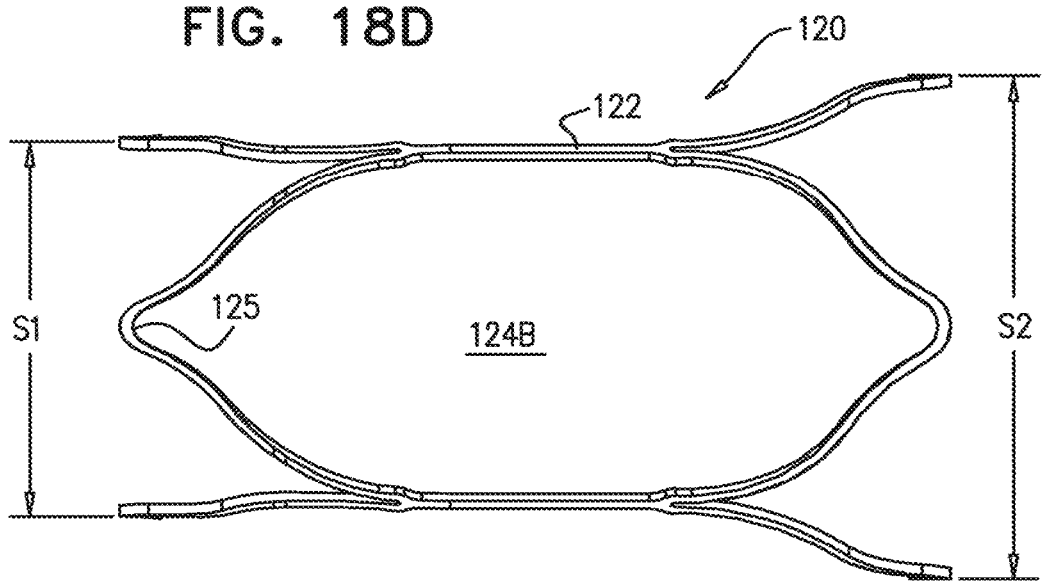

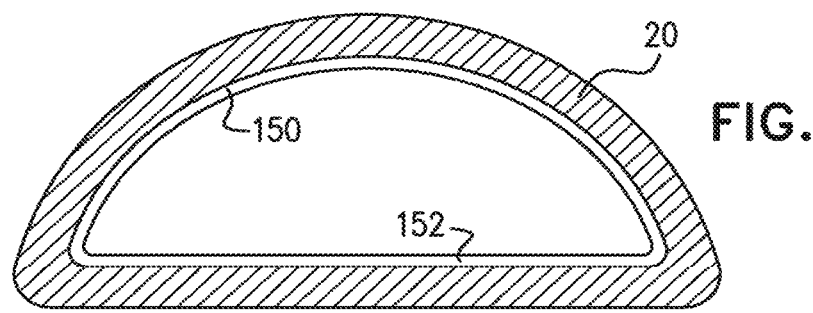
FIG. 19
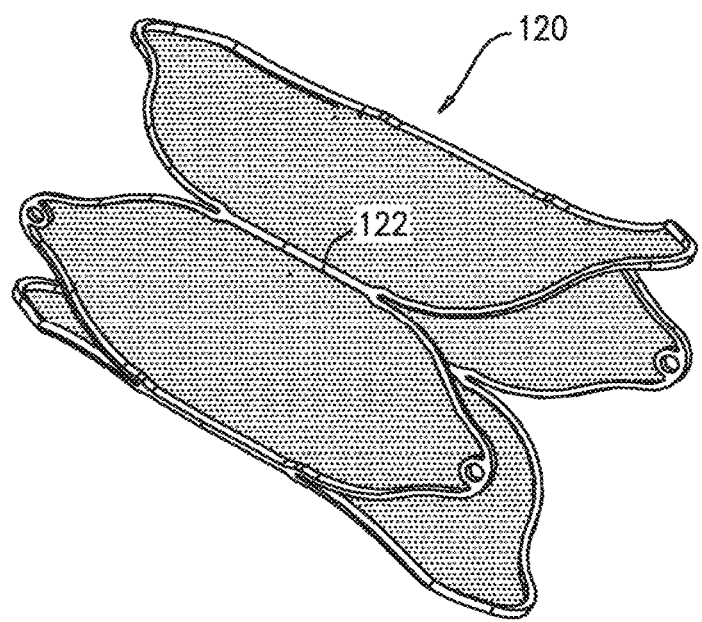
FIG. 20
FIG. 21
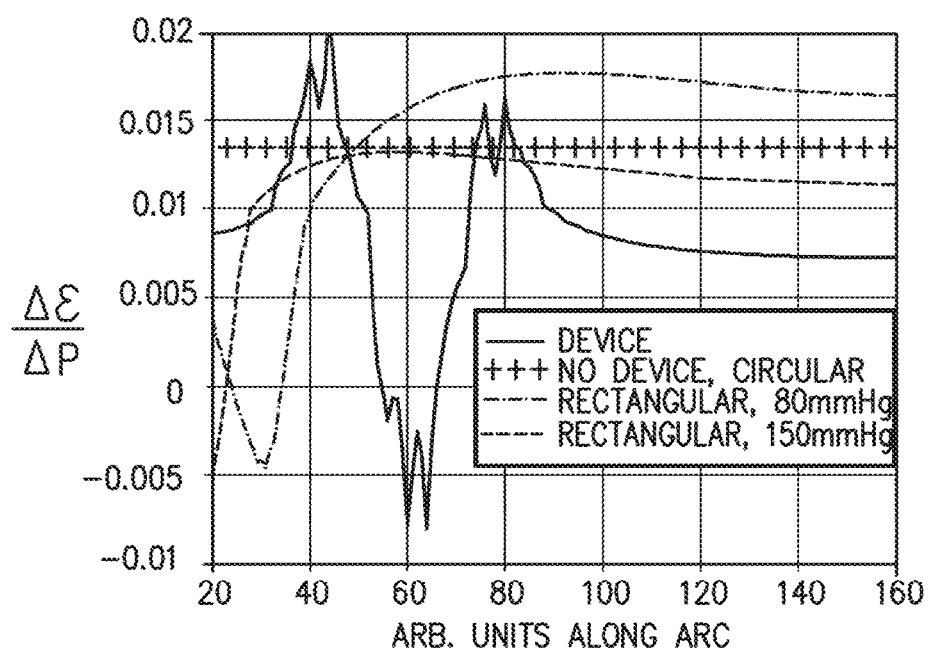

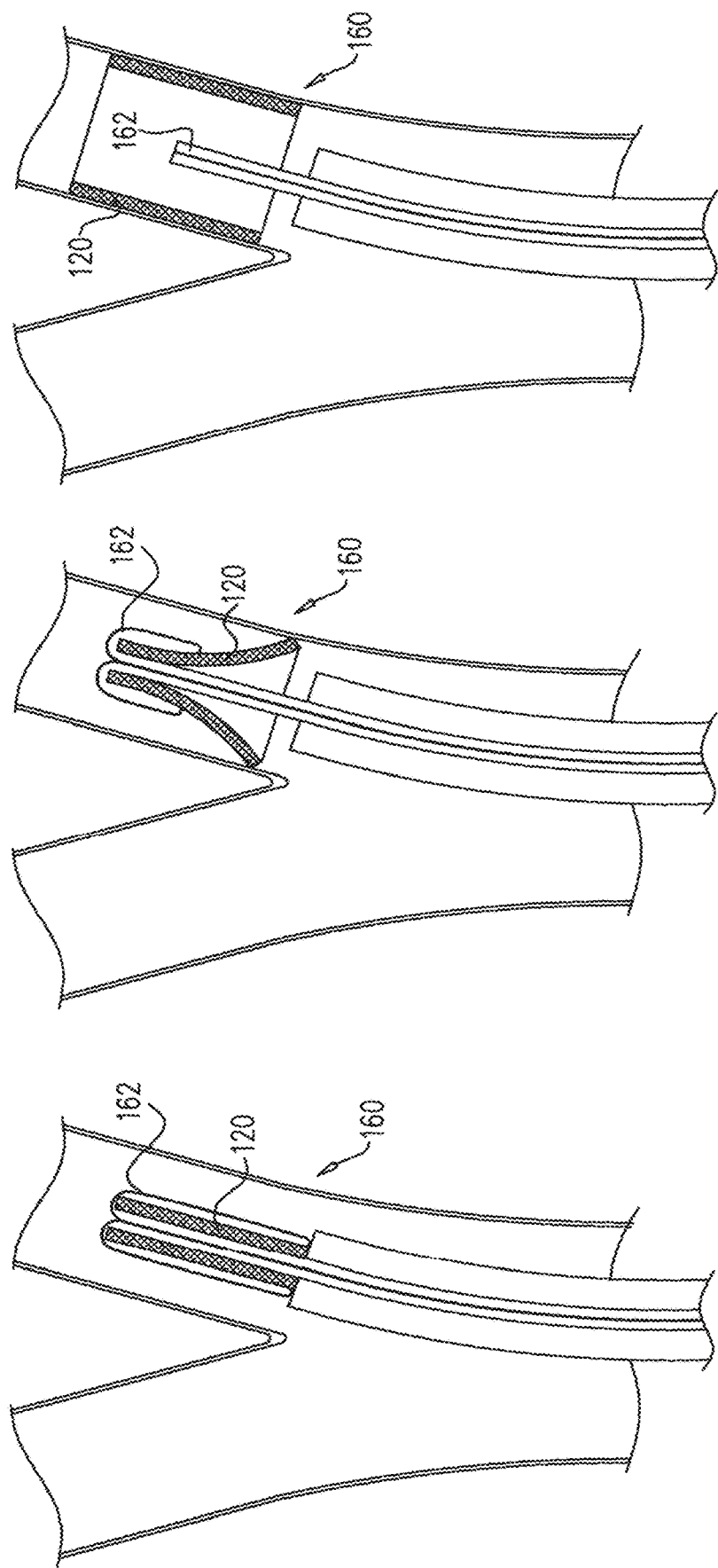

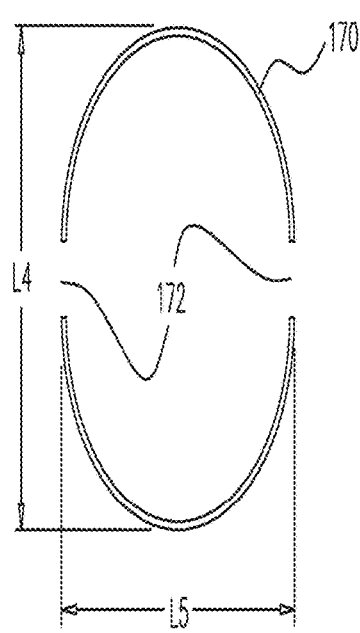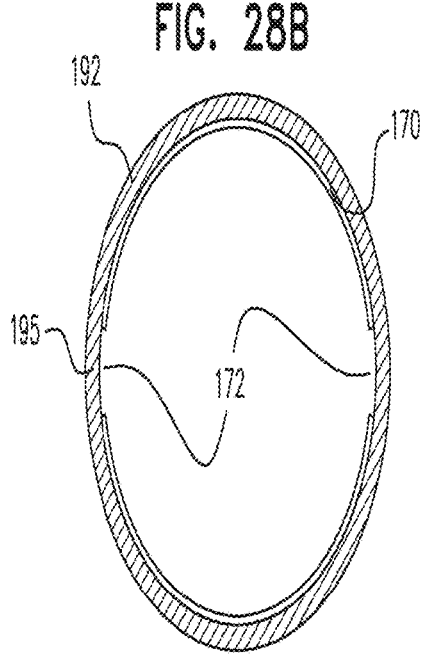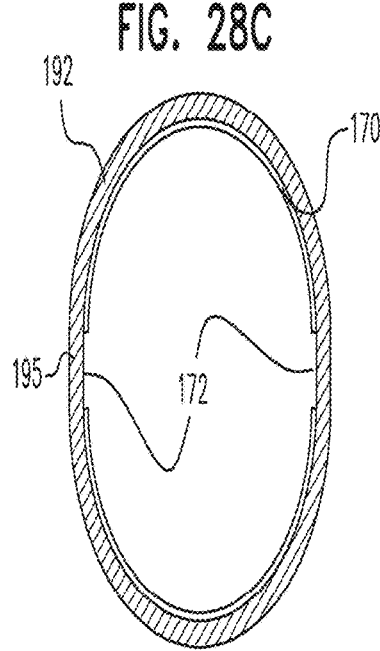

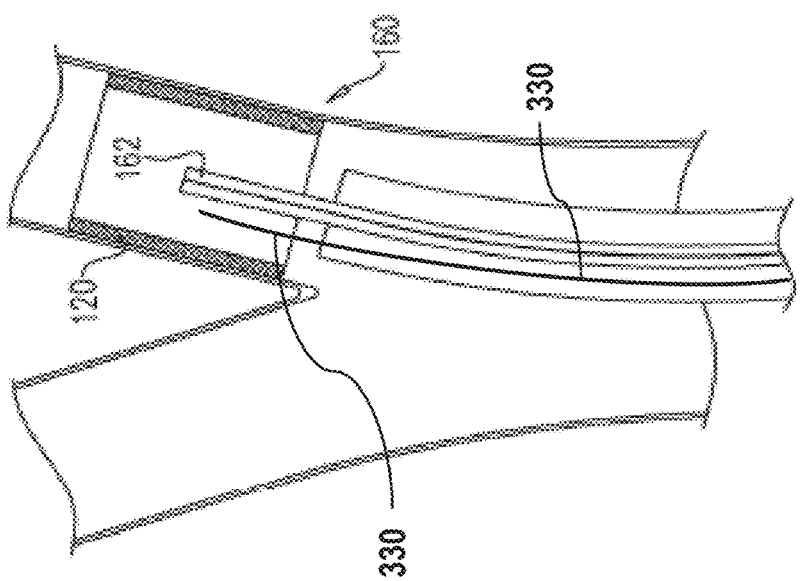
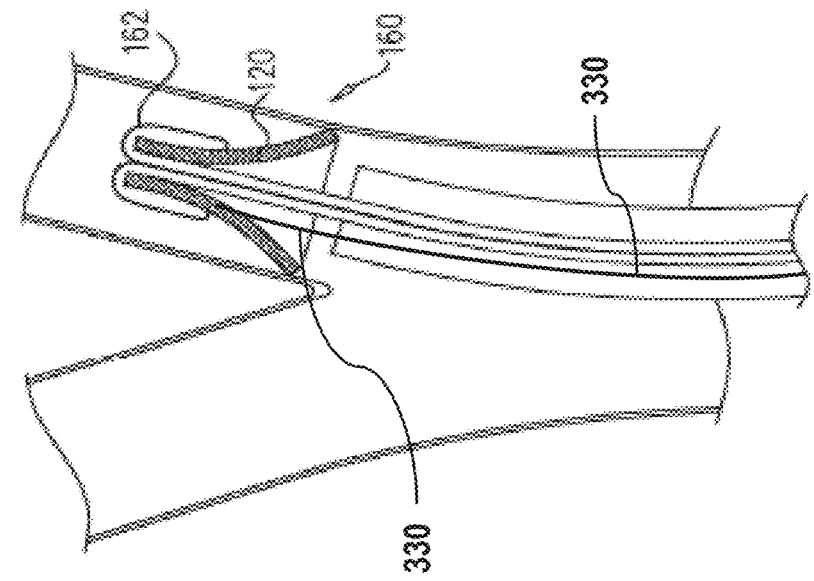
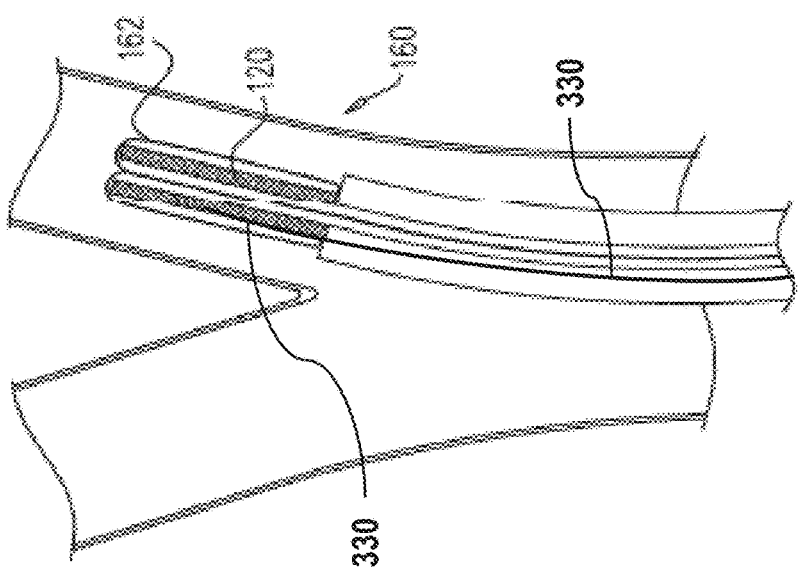

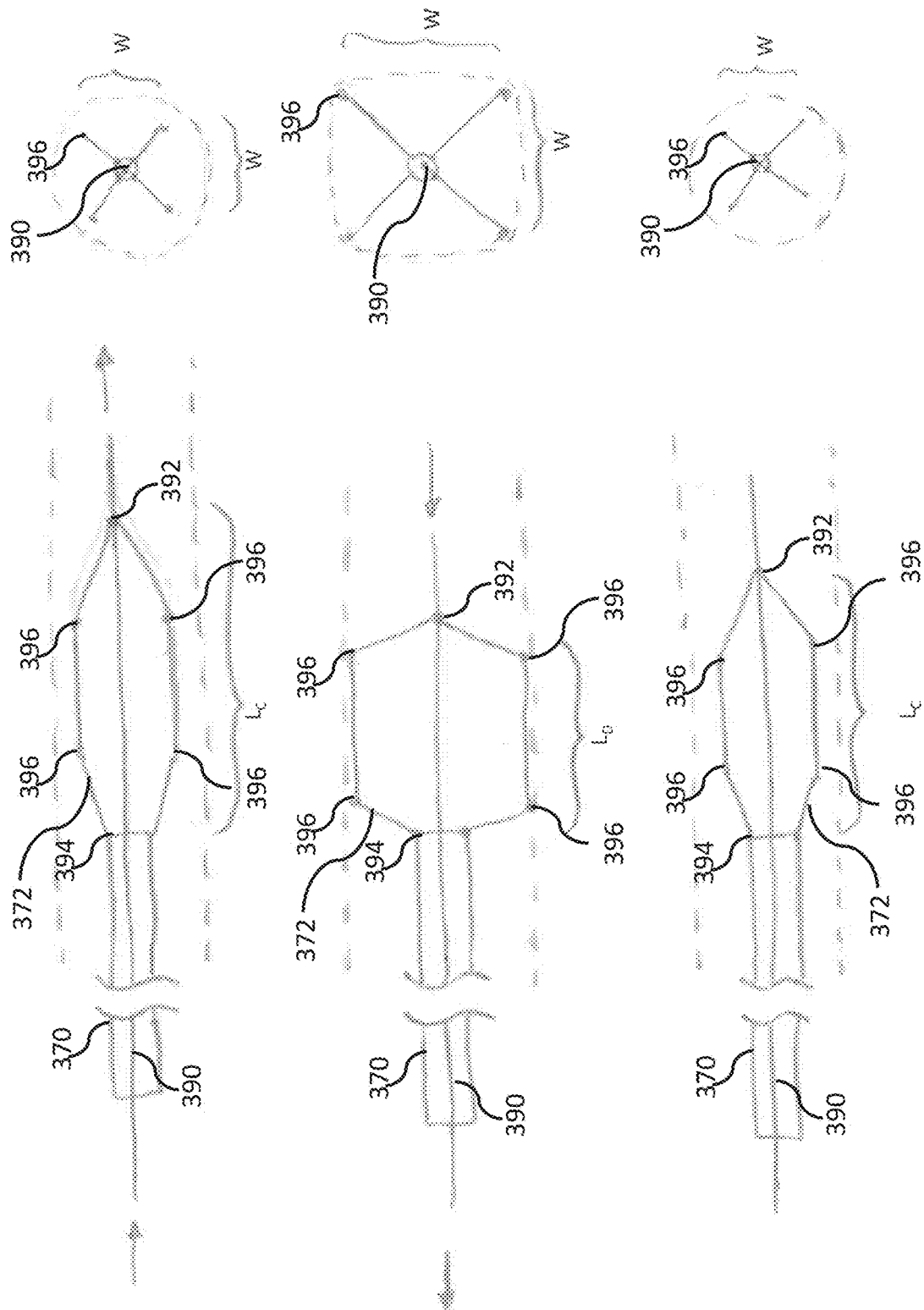

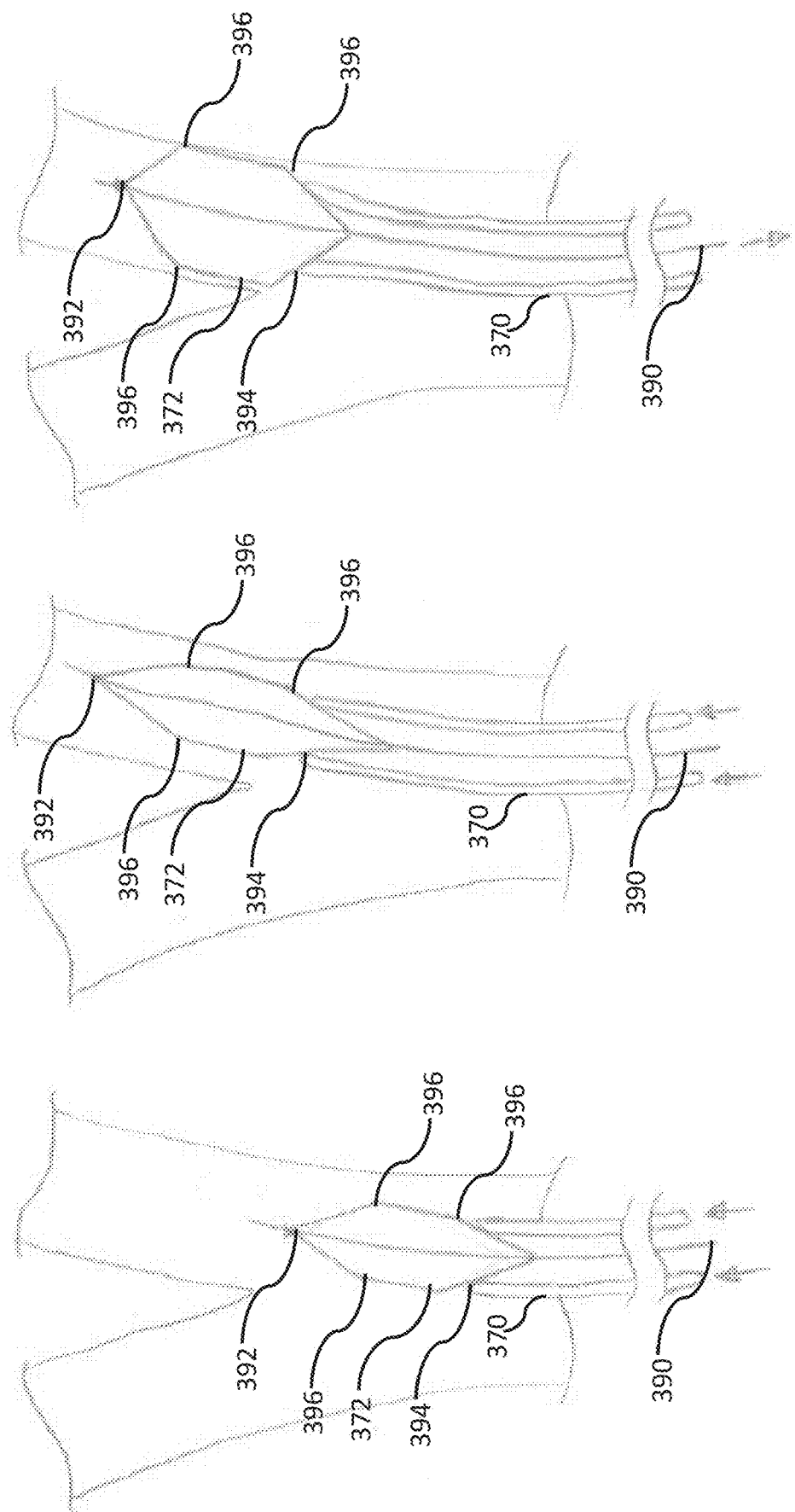

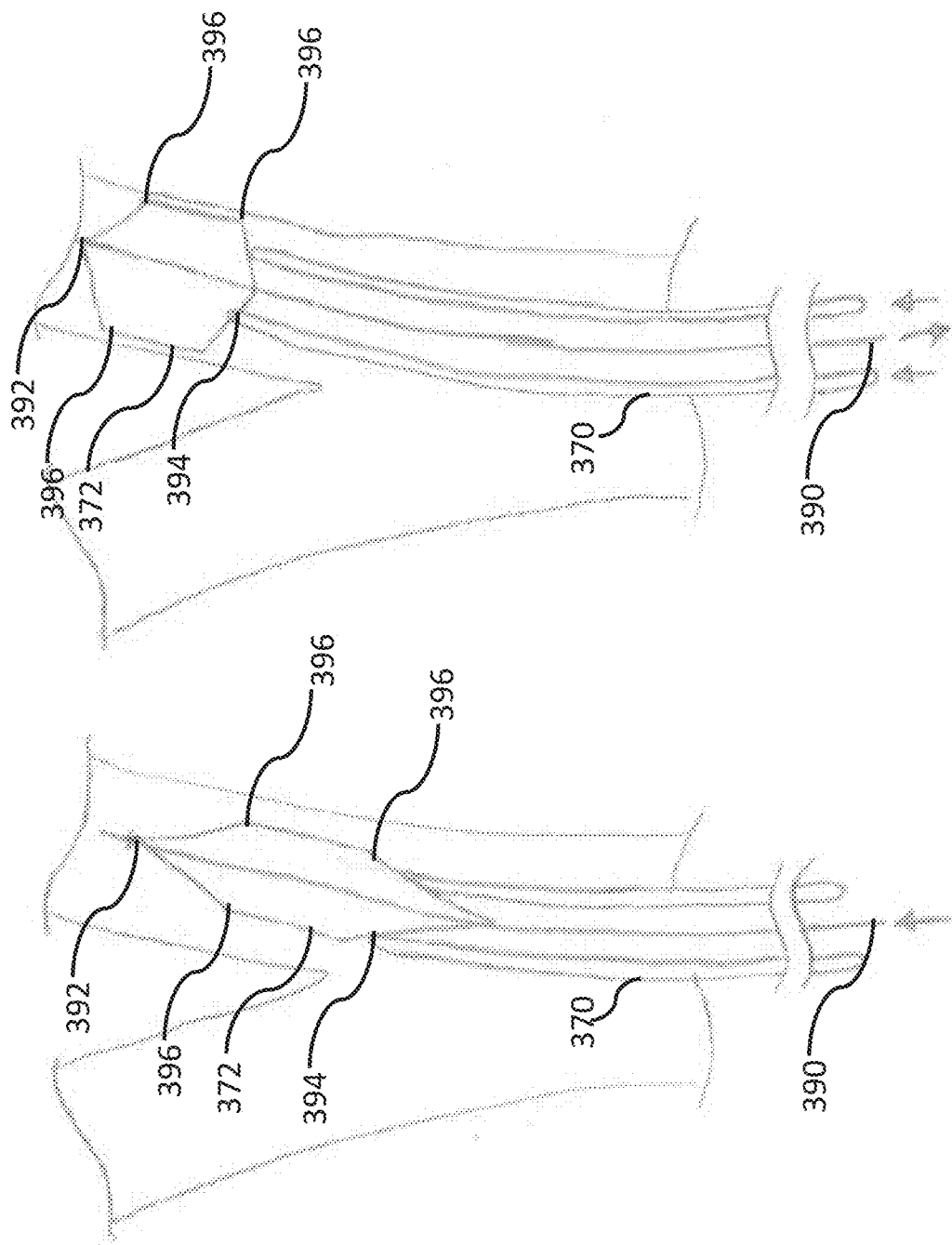

BARORECEPTOR TESTING PRIOR TO IMPLANTATION METHODS AND APPARATUS

CROSS-REFERENCES TO RELATED APPLICATIONS

This application claims priority to U.S. Provisional Patent Application No. 62/461,394, filed Feb. 21, 2017, the entire contents of which are incorporated herein by reference.

The subject matter of this application is related to the subject matter of U.S. application Ser. No. 13/455,005 to Gross et al. (published as US 2013/0172981), filed Apr. 24, 2012, which is a continuation-in-part of U.S. application Ser. No. 12/774,254 to Gross et al. (published as US 2011/0077729), filed May 5, 2010; and U.S. Ser. No. 13/030,384 to Gross et al. (published as US 2011/0178416), filed Feb. 18, 2011, which is a continuation-in-part of U.S. Ser. No. 12/774,254 to Gross et al., the entire contents of which are incorporated herein by reference.

The subject matter of this application is also related to the subject matter of U.S. patent application Ser. No. 11/881,256 (US 2008/0033501), filed Jul. 25, 2007, entitled "Elliptical element for blood pressure reduction," which is a continuation-in-part of PCT Application No. PCT/IL2006/000856 to Gross (WO 07/013065), filed Jul. 25, 2006, entitled, "Electrical stimulation of blood vessels," which claims the benefit of (a) U.S. Provisional Application 60/702,491, filed Jul. 25, 2005, entitled, "Electrical stimulation of blood vessels," and (b) U.S. Provisional Application 60/721,728, filed Sep. 28, 2005, entitled, "Electrical stimulation of blood vessels." The present application is related to U.S. patent application Ser. No. 12/602,787 (published as US 2011/0213408), which is the U.S. national phase of PCT Application No. PCT/IL2009/000932 to Gross et al. (WO 10/035271), filed Sep. 29, 2009, which claims priority from U.S. Provisional Patent Application 61/194,339, filed Sep. 26, 2008, entitled "Devices and methods for control of blood pressure." All of the above applications are incorporated herein by reference.

BACKGROUND

Some applications of the present disclosure generally relate to implanted medical apparatus. Specifically, some applications of the present disclosure relate to apparatus and methods for reducing blood pressure.

Hypertension is a condition from which many people suffer. It is a constant state of elevated blood pressure which can be caused by a number of factors, for example, genetics, obesity or diet. Baroreceptors located in the walls of blood vessels act to regulate blood pressure. They do so by sending information to the central nervous system (CNS) regarding the extent to which the blood vessel walls are stretched by the pressure of the blood flowing therethrough. In response to these signals, the CNS adjusts certain parameters so as to maintain a stable blood pressure.

SUMMARY

For some applications, a subject's hypertension may be treated by modulating the subject's baroreceptor activity. Mechanical forces and other stimuli can be applied directly or indirectly to one or more of the subject's arteries in order to modulate the baroreceptor response to the blood pressure. The forces can be applied to arteries that are rich in baroreceptors, for example, the carotid arteries, the aorta, the subclavian arteries and/or arteries of the brain. For some applications, the forces can be applied to other regions of the body that contain baroreceptors, such as the atria, the renal arteries, or veins.

In a hypertensive patient, the pressure-strain relationship can be shifted to higher pressures, such that the artery may be subject to a given strain at a higher blood pressure than the blood pressure in a healthy vessel that would give rise to the given strain. Thus, the baroreceptors may be activated at a higher blood pressure in a hypertensive patient than they are in a healthy patient. The devices described herein can cause the pressure-strain curve to shift back to lower pressures.

At constant pressure, by increasing the radius of curvature of a region of an arterial wall, the strain in the region of the wall may be increased. Thus, the baroreceptor nerve endings in the region (which may be disposed between the medial and adventitial layers of the artery, as described in further detail hereinbelow) may experience greater strain, ceteris paribus. The intravascular devices described herein may increase the radius of curvature of regions of the arterial wall without causing a substantial decrease in the cross-section of the artery (and can, in fact, cause an increase in the cross-section of the artery), thereby maintaining blood flow through the artery. For some applications, the devices can change the shape of the artery such that the artery is less circular than in the absence of the device, thereby increasing the radius of curvature of sections of the arterial wall.

For some applications the devices described herein may be implanted temporarily and may be subsequently removed. For example, devices described herein may be implanted for a period of less than one month, e.g., less than one week, less than a day, less than an hour, less than several minutes, less than a minute, etc. Temporary implantation of the devices can be used to treat an acute condition of the subject. For some applications, the shape of the artery in which the device is implanted can be permanently altered by temporarily implanting the device.

Typically, the devices described herein may be implanted inside or outside of the subject's carotid artery, e.g., in the vicinity of the carotid bifurcation. In accordance with respective embodiments, the devices may be implanted bilaterally, or inside or outside of only one of the subject's carotid arteries. Alternatively or additionally, the devices can be placed inside or outside of a different artery, e.g., the aorta or the pulmonary artery.

The devices may be self-anchoring and structurally stable. Further typically, the devices may be passive devices, i.e., subsequent to the devices being implanted inside or outside of the artery, the devices may act to increase baroreceptor sensitivity without requiring electrical or real-time mechanical activation.

Work in relation to embodiments of the present disclosure has revealed that while many subjects in a patient population are responsive to the baroreceptor modulation device and therapies described above and herein, at least some subject in the patient population may not be responsive or may only be partially responsive, for example, minimally responsive. For this subset of subjects or patients, the results obtained with implantation of a baroreceptor modulating implantable device such as those described herein may be less than ideal. Therefore, aspects of the present disclosure may also include systems and methods for screening a subject or patient before fully deploying the baroreceptor modulating implantable device.

Aspects of the present disclosure provide methods for screening a subject for therapy. Methods for screening a subject for therapy may comprise a step for providing at least one mechanical stimulus to a blood vessel, wherein the at least one mechanical stimulus can generate an increased radius of curvature at a first region of the blood vessel and a decreased radius of curvature at a second region of the blood vessel.

Consistent with methods described herein, a first region having an increased radius of curvature or a second region having a decreased radius of curvature can comprise at least one region of the blood vessel with increased strain. Furthermore, generating at least a first region of a blood vessel having an increased radius of curvature and at least a second region of a blood vessel having a decreased radius of curvature can result in the blood vessel increasing or maintaining its cross-sectional area, in accordance with methods described herein.

Methods described herein may comprise generating a plurality of first regions having an increased radius of curvature and a plurality of second regions having a decreased radius of curvature. For example, methods described herein can include generating at least three first regions having increased radius of curvature and at least three second regions having decreased radius of curvature. Methods described herein may also comprise generating three to seven first regions having an increased radius of curvature and three to seven second regions having a decreased radius of curvature. According to methods described herein, the first and second regions may alternate with one another around the circumference of the blood vessel.

Methods for screening a subject for therapy may comprise a step for detecting at least one change in at least one physiological parameter in response to at least one mechanical stimulus. In accordance with methods described herein, the at least one physiological parameter may comprise one or more of a baroreflex response, blood pressure, heart rate, blood vessel impedence, a sympathetic nerve activity, or a nerve activity.

Methods for screening a subject for therapy may also comprise a step for selecting an implant to provide the therapy based at least one change in at least one physiological parameter. As described herein, methods comprising selecting an implant to provide a therapy based on the detected at least one change in the at least one physiological parameter can also comprise selecting one implant of a plurality of implants, wherein the selected implant is suited to effect an optimal therapeutic response. An optimal therapeutic response described in relation to methods described herein can comprise an optimal baroreflex response modification.

Methods described herein may comprise selecting an implant, selection of the implant comprises selecting one or more of a size or geometry of the implant. In some cases, methods described herein comprise selecting an implant based on the implant's cross-sectional area. In accordance with methods described herein, an implant's size can be a cross-sectional area, and the implant's cross-sectional area can be in the range of 50.0 $mm^2$ to 60.0 $mm^2$, 60.0 $mm^2$ to 70.0 $mm^2$, 70.0 $mm^2$ to 80.0 $mm^2$, 80.0 $mm^2$ to 90.0 $mm^2$, 90.0 $mm^2$ to 100.0 $mm^2$, 100.0 $mm^2$ to 110.0 $mm^2$, 110.0 $mm^2$ to 120.0 $mm^2$, or 120.0 $mm^2$ to 130.0 $mm^2$. In accordance with methods described herein, an implant's geometry can comprise one or more of a number of vertices or corners of a cross-section of the implant, an orientation of the vertices or corners, or a number of vessel wall contacting struts of the implant.

According to the methods described herein, an implant can comprise an expandable scaffold. In certain embodiments of the methods described herein, the expandable scaffold can be configured to alter one or more of a geometry or cross-sectional area of a target region.

At least one mechanical stimulus may be provided intra-vascularly or extra-vascularly during a method for screening a subject for therapy. A method comprising providing at least one mechanical stimulus intra-vascularly may involve advancing a mechanical stimulus device for delivering a mechanical stimulus through the vasculature of a subject or patient to at least one target location or target region, which can be in a carotid artery, a carotid sinus, the aorta, the aortic arch, a subclavian artery, a cranial artery, the heart, or a common artery.

In accordance with methods described herein, the at least one mechanical stimulus can be provided by deploying a first implant from the mechanical stimulus device to the target location. Deploying the first implant to the target location can result in an increase in the curvature of at least a first region and a decreasing in the curvature of at least a second region of the blood vessel.

In accordance with methods described herein, providing the at least one mechanical stimulus can also comprise retracting the first implant from the target location. For example, the first implant can be retracted from the target location after a period of between 0 minutes and 1 minute, from 1 minute to 2 minutes, from 2 minutes to 3 minutes, from 3 minutes to 4 minutes, from 4 minutes to 5 minutes, from 5 minutes to 10 minutes, from 10 minutes to 20 minutes, from 20 minutes to 30 minutes, from 30 minutes to 1 hour, or from 1 hour to 2 hours. According to methods described herein, a second implant can be deployed from the mechanical stimulus device to the target location after retracting the first implant. In some cases, the second implant can increase the curvature of at least the first region of the blood vessel and decrease the curvature of at least the second region of the blood vessel differently than the first implant.

Aspects of the present disclosure provide systems for screening a subject for therapy. Systems for screening a subject for therapy may comprise a mechanical stimulus apparatus. A mechanical stimulus apparatus can be configured to provide at least one mechanical stimulus to a blood vessel according to the present disclosure. In certain embodiments, a mechanical stimulus can generate at least one first region of a blood vessel having an increased radius of curvature and at least one second region of the blood vessel having a decreased radius of curvature.

Systems for screening a subject for therapy may also comprise a sensor configured to detect at least one change in at least one physiological parameter in response to one or more mechanical stimulus. In certain embodiments, a sensor can comprise one or more of a baroreflex response sensor, a blood pressure monitor, a heart rate monitor, a blood vessel impedence monitor, a sympathetic nerve monitor, or a nerve sensor.

In some cases, systems for screening a subject for therapy can comprise an implant or a plurality of implants. An implant of systems described herein can comprise an expandable scaffold. Each implant of a system for screening a subject for therapy may have a number of vessel wall contacting struts in a range of between three and seven. In certain embodiments, each implant of a system described herein may have a cross-section having a polygonal shape with at least three vertices or corners. In some cases, the polygonal shape has three to seven vertices or corners. As described herein, an implant of a system or each implant of a system comprising a plurality of implants can have a cross-sectional area in a range between 50.0 mm$^2$ to 60.0 mm$^2$, 60.0 mm$^2$ to 70.0 mm$^2$, 70.0 mm$^2$ to 80.0 mm$^2$, 80.0 mm$^2$ to 90.0 mm$^2$, 90.0 mm$^2$ to 100.0 mm$^2$, 100.0 mm$^2$ to 110.0 mm$^2$, 110.0 mm$^2$ to 120.0 mm$^2$, or 120.0 mm$^2$ to 130.0 mm$^2$.

As described herein, a mechanical stimulus apparatus of a system for screening a subject for therapy can be configured to provide at least one mechanical stimulus intra-vascularly. A mechanical stimulus apparatus of a system for screening a subject can also be configured to provide at least one mechanical stimulus extra-vascularly.

A mechanical stimulus apparatus, as described herein, can be configured to provide one or more mechanical stimulus by deploying a first implant of a plurality of implants. In some cases, the first implant may apply a first mechanical stimulus to the blood vessel when deployed and may elicit a first change in at least one physiological parameter. A mechanical stimulus apparatus can also be configured to deploy a second implant of the plurality of implants. In certain embodiments, the second implant may apply a second mechanical stimulus to the blood vessel when deployed and may elicit a second change in the at least one physiological parameter. In some cases, the second change in the at least one physiological parameter is different from the first change. A mechanical stimulus apparatus, as described herein, can also be configured to retract an implant of a plurality of implants.

In some cases, either a first or second implant of a plurality of implants can be selected for long-term deployment in a blood vessel based on a first and a second change to at least one physiological parameter. In some cases, selection of either a first or second implant of a plurality of implants for long-term deployment can be based on which of a first or a second change to at least one physiological parameter indicates a more optimal therapeutic response. In some embodiments, an optimal therapeutic response can comprise an optimal baroreflex response modification, and, in some embodiments, long-term deployment of a selected implant in a blood vessel can comprise deployment of the selected implant for more than one day.

In certain embodiments, an implant of a system or each implant of a plurality of implants of a system described herein can be configured to alter one or more of the geometry or cross-sectional area of a target region in a blood vessel. In some cases, an implant of a system or each implant of a plurality of implants comprising a system described herein can be configured to alter the geometry of the target region by generating one or more first region of a blood vessel having an increased radius of curvature and one or more second region of a blood vessel having a decreased radius of curvature when deployed in a target region. In certain embodiments, the first regions and second regions generated by an implant of systems described herein may alternate with one another around a circumference of a blood vessel.

In certain embodiments, an individual implant of a plurality of implants of a system described herein can be selected for implantation into in the subject based on the at least one change in at least one physiological parameter detected by the sensor.

Aspects of the present disclosure may provide methods of screening a subject for a therapy. An implant delivery device may be advanced along the vasculature of the subject to a target location. An implant may be at least partially deployed from the implant delivery device to the target location. The target location may comprise a baroreceptor-rich region of the vasculature, such as the carotid artery, carotid sinus, aorta, aortic arch, subclavian artery, cranial artery, heart, or common artery, to name a few examples. A target change in blood pressure in response to the partially deployed implant may be detected. In response to the detected target change in blood pressure, it may then be determined whether to fully deploy the implant into the target region. The target change in blood pressure may indicate baroreceptor activity in the target location, such as a desired baroreceptor response. The target change in blood pressure may comprise a target drop in blood pressure.

If the target change in blood pressure is detected, the implant may be fully deployed to the target region as described above and herein. For example, the implant may comprise an expandable scaffold or stent-like device configured to be supported within a blood or other structure of the vasculature. The expandable scaffold may be configured to alter one or more of a geometry or a cross-sectional area of the target region. The implant may be configured to passively increase a baroreceptor signal in the target region when fully deployed, such as without additional electrical and/or thermal stimulus as described herein.

If the target change in blood pressure is not detected, the implant and the implant delivery device may be withdrawn from the target region. In at least some cases, the at least partially deployed implant may be repositioned in response to the detected target change in blood pressure. After repositioning, the target change in blood pressure may be again measured or detected, and the screening determination may again be made.

When the implant is at least partially deployed, the implant may contact an inner wall of the target region with a contact region of the implant. The at least partially deployed implant may one or more of increase a radius of curvature or increase a cross-sectional area of the target region with the implant contacting the inner wall of the target region with the contact region of the implant. To contact the inner wall of the target region, an expanded distal region of the implant may contact the contact region while a proximal region of the implant is maintained in a collapsed state or an expanded proximal region of the implant may contact the contact region while a distal region of the implant is maintained in a collapsed state. The inner wall of the target location may be contacted and the inner wall may be electrically mapped, such as with the at least partially deployed implant.

In some embodiments, the method may further comprise stimulating the target region. The target region may be stimulated from a stimulation device external of the vasculature and the target region. Alternatively or in combination, the target region may be stimulated intravascularly, such as with one or more of the at least partially deployed implant or implant delivery device advanced to the target region. The stimulation may comprise the application of one or more of electrical, radiofrequency, thermal, chemical, or mechanical energy to the target region. For example, electrical energy may be applied to the target region through at least one lead coupled to one or more of the at least partially deployed implant or implant delivery device. The electrical energy may be in direct current (DC) or alternating current (AC). The lead may traverse at least a distal portion of the implant delivery device to be in conductive contact with a collapsed portion of the at least partially deployed implant. The conductive contact may comprise a metal-to-metal contact between the lead and the collapsed portion. The collapsed portion may be a proximal or distal portion of the implant.

Mechanical energy may be applied with the contact region of the at least partially deployed stent in contact with the inner wall of the target region.

The target change in blood pressure may be detected in response to the stimulation of the target region. Furthermore, heart rate and/or changes in heart rate may be measured as an indicator of baroreceptor response as well. For example, a baro-reflex may be determined based on changes in blood pressure and changes in heart rate timing. Baroreceptor response may also be detected electrically using one or more electrodes to measure electrical activity in the target region tissue and/or adjacent nerves, by monitoring blood flow characteristics such as velocity and flow rate, by monitoring blood oxygenation, or by measuring mechanical forces to the target region tissue, to name a few examples. Based on such indicators, it may be determined whether to fully deploy the implant into the target region.

Aspects of the present disclosure may provide systems for screening a subject for a therapy. The system may comprise an implant delivery device configured to be advanced along vasculature, an implant configured to be deployed by the implant delivery device, a lead coupled to one or more of the implant delivery device or the implant to deliver a stimulation signal to a target region, and a sensor configured to detect a target change in blood pressure in response to the implant being at least partially deployed in the target region and the stimulation signal delivered to the target region. The target change in blood pressure may indicate baroreceptor activity in the target location, such as a desired baroreceptor response. The target change in blood pressure may comprise a target drop in blood pressure.

The implant delivery device may comprise a delivery catheter, such as a retractable sheath enclosing at least a portion of the implant and retractable to deliver the implant to the target site. The implant may comprise an expandable scaffold configured to be supported within a blood vessel or other structure of the vasculature. The expandable scaffold may be configured to alter one or more of a geometry or cross-sectional area of the target region. Such stent-like implantable devices or expandable scaffolds are described herein, for example, with reference to FIGS. 17A-17C. The retractable sheath may be retractable in the distal direction to expose an expanded proximal portion of the implant while maintaining the distal portion of the implant in a collapsed configuration. Such delivery devices and scaffolding or stent-like implantable devices are described herein, for example, with reference to FIGS. 22A-22C. Alternatively, the retractable sheath may be retractable in the proximal direction to expose an expanded distal portion of the implant while maintaining the proximal portion of the implant in a collapsed configuration. Also, as described herein, the implant may be configured to passively increase a baroreceptor signal in the target region when fully deployed. The implant may comprise a contact region configured to contact an inner wall of the target region when at least partially deployed. The at least partially deployed implant may one or more of increase a radius of curvature or increase a cross-sectional area of the target region with the contact region. The contact region may comprise one or more longitudinal struts, such as a plurality of longitudinal struts. The plurality of longitudinal struts may be arranged to form at least four sides, at least two of the four sides being configured to contact and apply pressure to the inner wall of the target region. At least two of the four sides may be configured to be crimping regions to facilitate transitioning the implant to a collapsed configuration.

The lead may be configured to deliver the stimulation signal to the target region through one or more of the implant delivery device or implant. The lead may be configured to contact an inner wall of a blood vessel to deliver the stimulation signal to the target region. The stimulation signal may comprise an electrical stimulation signal, and the lead may be configured to convey the electrical signal to the target region. The lead may traverse at least a distal portion of the implant delivery device to be in conductive contact with a collapsed portion of the at least partially deployed implant. The conductive contact may comprise a metal-to-metal contact between the lead and the collapsed portion. The collapsed portion may be a proximal or distal portion of the implant. The electrical stimulation signal may be in direct current (DC) or alternating current (AC). The stimulation signal may comprise a thermal stimulation signal, and the lead may be configured to convey the thermal signal to the target region. The stimulation signal may comprise a mechanical stimulation signal, and one or more of the implant delivery device or implant may be configured to convey the mechanical stimulation signal to the target region. The mechanical stimulation signal may comprise an expansion of at least a portion of the implant to contact and apply pressure to an inner wall of the target region.

The sensor may comprise one or more of a blood pressure sensor, an arterial line, a heart rate monitor, an impedance sensor, or a mapping electrode, which may be, for example, coupled to the lead. Baroreceptor response may also be detected electrically using one or more electrodes to measure electrical activity in the target region tissue and/or adjacent nerves, by monitoring blood flow characteristics such as velocity and flow rate, by monitoring blood oxygenation, or by measuring mechanical forces to the target region tissue, to name a few examples.

The present disclosure will be more fully understood from the following detailed description of embodiments thereof, taken together with the drawings, in which:

BRIEF DESCRIPTION OF THE DRAWINGS

FIG. 3 is a contour plot of the strain in the wall of an artery, an extravascular device having been implanted outside the wall, in accordance with some applications of the present disclosure;

FIGS. 9A-9D are schematic illustrations of extravascular devices placed around an artery, in accordance with some applications of the present disclosure;

FIGS. 16A-16D are schematic illustrations of another device for placing in a subject's artery, in accordance with some applications of the present disclosure;

FIGS. 18A-18D are schematic illustrations of further devices for placing in a subject's artery, in accordance with some applications of the present disclosure;

FIG. 19 is a schematic illustration of a device having a D-shaped cross-section for placing in a subject's artery, in accordance with some applications of the present disclosure;

FIG. 20 is a schematic illustration of an intra-arterial device that includes a mesh between artery contact regions of the device, in accordance with some applications of the present disclosure;

FIG. 21 is a graph showing the derivative of strain versus pressure as a function of rotational position around the artery, in accordance with respective models of an artery, in accordance with some applications of the present disclosure;

FIGS. 22A-22C are schematic illustrations of a delivery device for placing an intra-arterial device at a subject's carotid bifurcation, in accordance with some applications of the present disclosure;

FIGS. 23A-23B, 24A-24B, 25A-25B, 26A-26B, 27A-27D, and 28A-28C are schematic illustration of stent-based intra-arterial devices, in accordance with some applications of the present disclosure;

FIGS. 33A-33C is a schematic illustration of a delivery device for screening a subject or patient for placement of an intra-arterial device at a subject's carotid bifurcation, in accordance with some applications of the present disclosure.

FIGS. 39A-39C are schematic illustrations of additional devices and steps useful in the screening of a subject or patient for therapy, in accordance with some applications of the present disclosure.

FIGS. 40A-40E are schematic illustrations of steps in the use of a system for the screening of a subject or patient for therapy, in accordance with some applications of the present disclosure.

DETAILED DESCRIPTION

Figure 1:
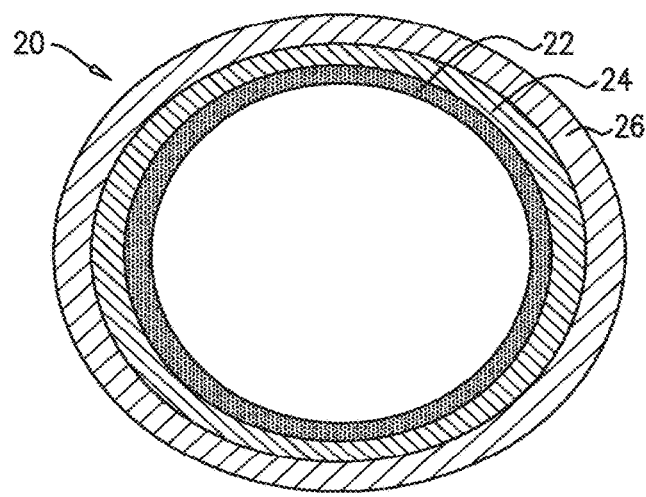
FIG. 1 is a cross-sectional illustration of an artery.

Reference is now made to FIG. 1, which is a cross-sectional illustration of an artery 20. The arterial wall includes three layers 22, 24, and 26, which are called, respectively, the intima, the media, and the adventitia. For some applications of the present disclosure, an intravascular device is placed inside an artery, baroreceptors being disposed at the interface between adventitia 26 and media 24 of the artery. The device causes the curvature of the arterial wall to flatten in some regions of the circumference of the arterial wall, thereby causing the baroreceptors to become stretched, while allowing the regions to pulsate over the course of the subject's cardiac cycle.

Figure 2A:
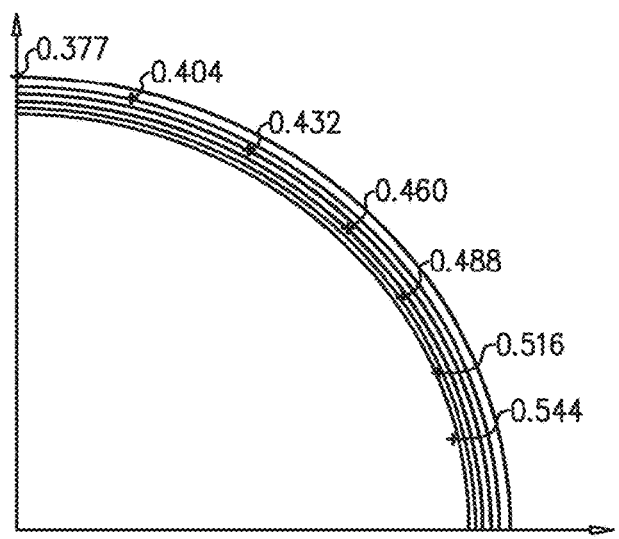
FIGS. 2A-2B are contour plots of the strain in the wall of an artery, respectively, when the artery does have and does not have inserted therein an intravascular device, in accordance with some applications of the present disclosure.
Figure 2B:
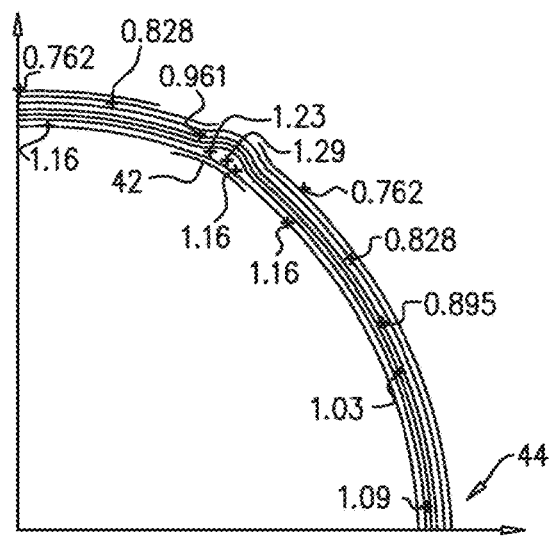

Reference is now made to FIGS. 2A and 2B, which are contour plots of the strain in the top right quarter of an arterial wall, in the absence of an intravascular device (FIG. 2A) and in the presence of an intravascular device (FIG. 2B), analyzed and/or provided in accordance with some applications of the present disclosure. The contour plot in FIG. 2B was generated for a device (e.g., as shown hereinbelow in FIGS. 7A-B) having four elements, each of which contacts the arterial wall at a contact region 42. The contour plots shown in FIGS. 2A-B are computer simulations of the strain in the wall of an artery, at a blood pressure of 100 mmHg, the artery having a radius of 3 mm, and a wall thickness of 0.6 mm. The scope of the present application includes intravascular devices having different structures from that used to generate FIG. 2B, as would be obvious to one skilled in the art.

As seen in FIGS. 2A-2B, relative to the strain in the arterial wall in the absence of an intravascular device, the intravascular device causes there to be increased strain in the arterial wall both (a) in the vicinity of contact regions 42, at which the arterial wall becomes more curved than in the absence of the device, and (b) in flattened regions 44 of the wall, in which regions the arterial wall is flatter than it is in the absence of the device. Thus, the intravascular device increases the strain in the arterial wall even in regions of the arterial wall which are able to pulsate, i.e., flattened regions 44. The increased strain in the flattened regions relative to the strain in the wall in the absence of the intravascular device is due to the increased radius of curvature of the flattened regions of the wall.

Reference is now made to FIG. 3, which is a contour plot of the strain in the top right quarter of an arterial wall, in the presence of an extravascular device, in accordance with some applications of the present disclosure. The contour plot in FIG. 3 was generated for a device having four elements that contact the artery at four contact regions 52. However, the scope of the present disclosure includes extravascular devices having different structures, as described hereinbelow. For example, an extravascular device may provide three to six contact regions. The contour plot shown in FIG. 3 is a computer simulation of the strain in the wall of an artery, at a blood pressure of 100 mmHg, the artery having a radius of 3 mm, and a wall thickness of 0.6 mm.

As may be observed by comparing FIG. 3 to FIG. 2A, the extravascular device causes there to be strain in the arterial wall in the vicinity of contact regions 52, at which the arterial wall becomes more curved than in the absence of the device. Furthermore, it may be observed that the strain at non-contact regions 54 of the wall is lower than in the absence of the device. The extravascular device typically breaks the circumferential symmetry of the arterial strain by applying force at discrete points or surfaces around the sinus. For some applications, the extravascular device increases the strain in certain regions of the arterial wall, and decreases the strain in other regions of the arterial wall, while maintaining the average strain almost unchanged or even slightly reduced with respect to the strain in the wall in the absence of the device. For some applications, the extravascular device increases the strain in the arterial wall even at non-contact regions 54, by causing the non-contact regions to become more curved than in the absence of the device.

Figure 4:
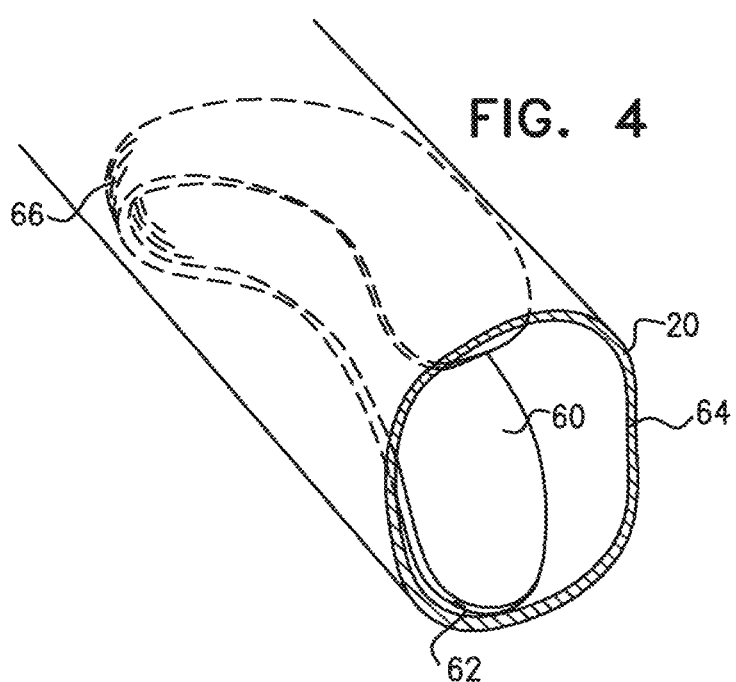
FIG. 4 is a schematic illustration of an intravascular device for placing inside an artery of a subject suffering from hypertension, in accordance with some applications of the present disclosure.

Reference is now made to FIG. 4, which is a schematic illustration of an intravascular device 60 for placing inside artery 20 of a subject suffering from hypertension, in accordance with some applications of the present disclosure. As shown, device 60 contacts the arterial wall at two contact regions 62. At the contact regions, device 60 pushes the arterial wall outward, thereby flattening non-contact regions 64 of the arterial wall between the contact regions. Typically, non-contact regions 64 are flattened, or partially flattened during diastole of the subject, but expand during systole such that they become more curved than during diastole. Therefore, strain in the flattened regions of the arterial wall is increased. However, the flattened regions still pulsate over the course of the subject's cardiac cycle in the presence of device 60.

As shown, device 60 is shaped such that the device substantially does not reduce blood flow. Typically, device 60 is shaped such that no portion of the device intersects the longitudinal axis of the artery. For example, as shown, contact surfaces of the device (which contact the arterial wall at contact regions 60) are coupled to each other by a joint 66 that does not intersect the longitudinal axis of the artery. The joint is disposed asymmetrically with respect to centers of the contact surfaces of the device.

Figure 5A:
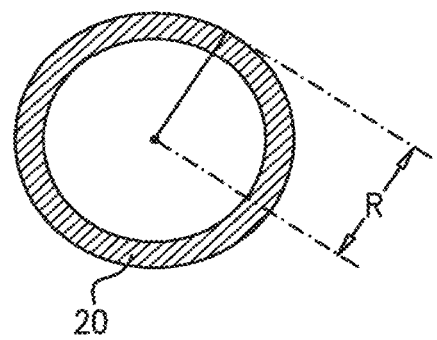
FIGS. 5A-5B are schematic illustrations of an artery, showing the radius of curvature of the artery, respectively, before and after placement of the device shown in FIG. 4, in accordance with some applications of the present disclosure.
Figure 5B:
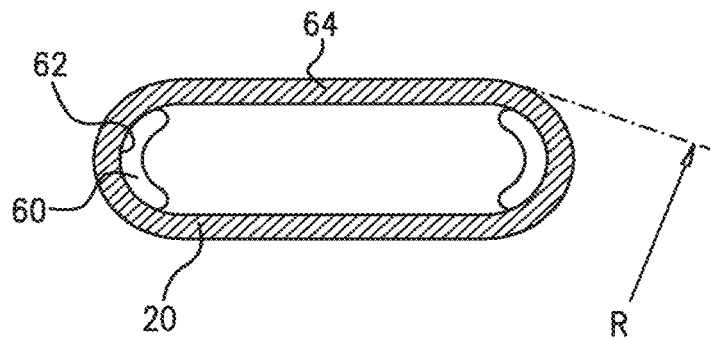

Reference is now made to FIGS. 5A-5B, which are schematic illustrations of an artery, showing the radius R of artery 20, respectively, before and after placement of the device 60 shown in FIG. 4, in accordance with some applications of the present disclosure. It may be observed that, for some applications, insertion of device 60 increases the systolic radius of curvature of the artery at non-contact regions 64, for example, such that the radius of curvature at non-contact regions 64 is more than 1.1 times (e.g., twice, or more than twenty times) the systolic radius of curvature of regions 64 in the absence of device 60, ceteris paribus. For some applications, device 60 causes the radius of curvature of at least a portion of a non-contact region to become infinite, by flattening the non-contact regions. For example, the center of non-contact region 64 in FIG. 5B has an infinite radius of curvature.

For some applications, device 60 increases the systolic radius of curvature of the artery at non-contact regions 64 in the aforementioned manner, and increases the systolic cross-sectional area of the artery by more than five percent (e.g., ten percent), relative to the systolic cross-sectional area of the artery in the absence of device 60.

In accordance with the description hereinabove, by flattening non-contact regions 64 of the wall of artery 20, device 60 causes increased strain in regions 64, thereby causing an increase in baroreceptor firing at regions 64. Alternatively or additionally, device 60 causes increased baroreceptor firing at contact regions 62, by deforming the arterial wall at the contact regions.

Typically, device 60 exerts a force on artery 20, such that, during systole when the artery is in the stretched configuration shown in FIG. 5B, non-contact regions 64 comprise more than ten percent, e.g., more than 20 percent, of the circumference of the arterial wall at longitudinal sites at which device 60 stretches the artery. For some applications, during systole, non-contact regions 64 comprise more than 60 percent, e.g., more than 80 percent, of the circumference of the arterial wall at longitudinal sites at which device 60 stretches the artery.

Figure 5C:
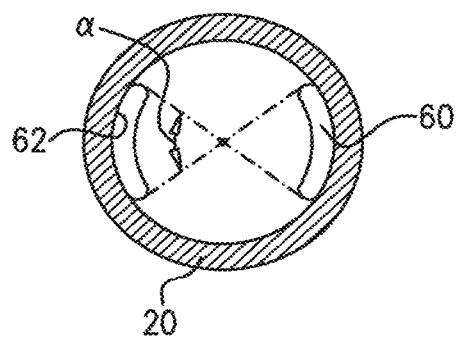
FIG. 5C is a schematic illustration of the device of FIG. 4 disposed inside the artery, without stretching the artery, for illustrative purposes.

Reference is now made to FIG. 5C, which shows device 60 disposed inside artery 20, but without the device stretching artery 20. FIG. 5C is for illustrative purposes, since typically once device 60 is inserted into the artery, the device will stretch the artery, as shown in FIG. 5B. FIG. 5C demonstrates that the device contacts the walls of the artery at contact regions 62 at less than 360 degrees of the circumference of the artery at any longitudinal point along artery 20 (e.g., at the cross-section shown in FIGS. 5A-C). As shown in FIG. 5C, each of the contact regions 62 encompasses an angle alpha of the circumference of the artery, such that the contact that device 60 makes with the walls of the artery encompasses two times alpha degrees. For devices that contact the artery at more than two contact regions, the contact that the device makes with the walls of the artery encompasses an angle that is a correspondingly greater multiple of alpha degrees. Typically, device 60 (and the other intravascular devices described herein) contacts the walls of the artery at less than 180 degrees (e.g., less than 90 degrees) of the circumference of the artery at any longitudinal site along the artery. Typically, device 60 contacts the walls of the artery at more than 5 degrees (e.g., more than 10 degrees) of the circumference of the artery at any longitudinal site along the artery. For example, device 60 may contact the walls of the artery at 5-180 degrees, e.g., 10-90 degrees, at a given longitudinal site.

Figure 6A:
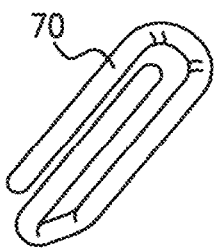
FIGS. 6A-6B are schematic illustrations of, respectively, a device, and the device implanted inside an artery, in accordance with some applications of the present disclosure.
Figure 6B:
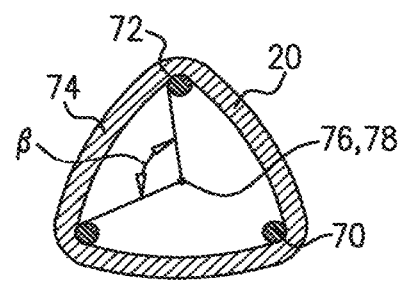

Reference is now made to FIGS. 6A-6B, which are schematic illustrations of, respectively, a device 70, and device 70 implanted inside artery 20, in accordance with some applications of the present disclosure. Device 70 contacts the wall of the artery at three contact regions 72, thereby increasing the radius of curvature (i.e., flattening) of non-contact regions 74 of the artery that are between the contact regions. The flattened non-contact regions and the contact regions alternate with each other. The flattened non-contact regions are typically able to pulsate over the course of the subject's cardiac cycle, as described hereinabove. As shown in FIG. 6B, each contiguous non-contact region at a given longitudinal site of the artery, encompasses an angle beta around a longitudinal axis 76 of the artery. For some devices (e.g., device 70, and device 90 described hereinbelow with reference to FIGS. 8A-8B), the angle beta is also defined by the angle that edges of adjacent contact regions of the device define around longitudinal axis 78 of the device. When the device is placed in the artery longitudinal axis 78 of the device is typically aligned with longitudinal axis 76 of the artery. Typically, angle beta is greater than 10 degree, e.g., greater than 20 degree, or greater than 50 degrees. Further typically, angle beta is less than 180 degrees, e.g., less than 90 degrees. For some applications angle beta is 10-180 degree, e.g., 20-90 degrees. Typically, each of the contiguous non-contact regions is able to pulsate.

Figure 7A:
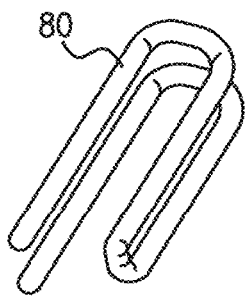
FIGS. 7A-7B are schematic illustrations of, respectively, another device, and the device implanted inside an artery, in accordance with some applications of the present disclosure.
Figure 7B:
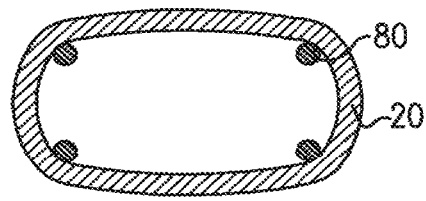

Reference is now made to FIGS. 7A-7B, which are schematic illustrations of, respectively, a device 80, and device 80 implanted inside artery 20, in accordance with some applications of the present disclosure. Device 80 contacts the wall of the artery at four contact regions, thereby flattening the non-contact regions of the artery that are between the contact regions. Each contiguous non-contact region at a given longitudinal site of the artery, encompasses an angle beta around the longitudinal axis of the artery, angle beta being as described hereinabove.

Figure 8A:
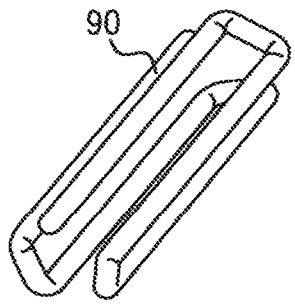
FIGS. 8A-8B are schematic illustrations of, respectively, a further device, and the device implanted inside an artery, in accordance with some applications of the present disclosure.
Figure 8B:
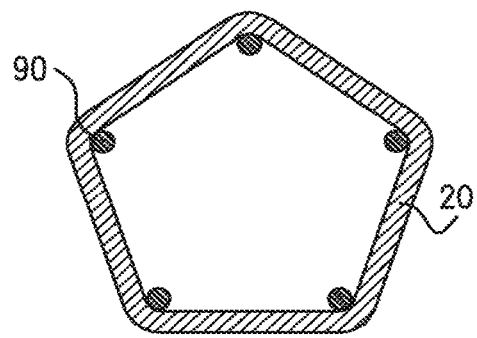

Reference is now made to FIGS. 8A-8B, which are schematic illustrations of, respectively, a device 90, and device 90 implanted inside artery 20, in accordance with some applications of the present disclosure. Device 90 contacts the wall of the artery at five contact regions, thereby flattening the non-contact regions of the artery that are between the contact regions. Each contiguous non-contact region at a given longitudinal site of the artery, encompasses an angle beta around the longitudinal axis of, angle beta being as described hereinabove.

Apart from the fact that devices 70, 80, and 90 contact the artery at, respectively three, four, and five contact regions, devices 70, 80, and 90 function in a generally similar manner to each other, and to device 60, described with reference to FIGS. 4 and 5A-5C. For example, devices 70, 80, and 90 typically contact the arterial wall around substantially less than 360 degrees of the circumference of the artery, for example, around 10-90 degrees, or around an angle as described hereinabove with reference to FIGS. 5A-5C. Furthermore, devices 70, 80, and 90 typically increase the cross-sectional area of the artery relative to the cross-sectional area of the artery in the absence of the device.

For some applications, a device having three or more contact regions with the arterial wall, for example, as shown in FIGS. 6A-8B, is used. It is noted that since device 60 (shown in FIG. 4) contacts the artery at two contact points, as the device applies increasing pressure to the artery, it will, at a given stage, decrease the cross-section of the artery, as the artery becomes increasingly elliptical. By contrast, devices 70, 80, and 90, which contact the artery at three or more contact points, increase the cross-section of the artery, as they apply increasing pressure to the wall of the artery. Thus, for some applications, a device with three or more contact regions is used in order that the cross-sectional area of the artery is increased as the force which the device exerts on the wall increases, as compared with a device with only two contact regions.

Although devices that contact artery 20 at two, three, four and five contact regions have been described, the scope of the present disclosure includes devices that contact the artery at a different number of contact regions, and/or that have different structures from those shown, mutatis mutandis.

The intravascular devices described herein are generally shaped such that the devices contact the intravascular wall at relatively small contact regions, and provide relatively large contiguous non-contact regions, which are able to pulsate due to the subject's cardiac cycle.

The devices are typically shaped such that the total contact region that the device makes with the arterial wall at any longitudinal point along the artery is less than 2 mm, e.g., less than 0.5 mm. The contact region is usually larger than 0.05 mm, e.g., greater than 0.2 mm. For example, the contact region may be 0.05-2 mm, e.g., 0.1-0.4 mm, or 0.2-0.5 mm. The devices are typically inserted into an artery that has an internal circumference during systole of 6-8 mm. Thus, the intravascular devices described herein are typically configured to contact less than 35 percent of the circumference of the artery at any longitudinal point along the artery, and at any point in the subject's cardiac cycle (or, for at least a portion of the cardiac cycle). Further typically, the intravascular devices described herein are configured to contact more than 0.5 percent of the circumference of the artery at any longitudinal point along the artery, and at any point in the subject's cardiac cycle (or, for at least a portion of the cardiac cycle). For some applications, the contact region may be 0.5-35 percent of the circumference of the artery (or, for at least a portion of the cardiac cycle).

For some applications, the intravascular devices described herein have a total cross-sectional area of less than 5 sq mm, e.g., less than 0.8 sq mm, or less than 0.5 sq mm. (The total cross-sectional area should be understood to refer to the cross-sectional area of the solid portions of the devices, and not the space in between the solid portions.) The devices typically have this cross-sectional area over a length of the device of more than 4 mm, e.g., more than 6 mm, and/or less than 12 mm, e.g. less than 10 mm. For example, the devices may have the aforementioned cross sectional area over a length of 4 mm-12 mm, e.g., 6 mm-10 mm. The devices are typically manufactured from nitinol, cobalt chrome, and/or passivated stainless steel 316L.

Figure 9A:
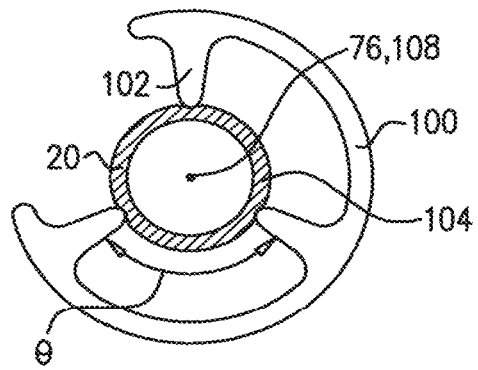

Reference is now made to FIGS. 9A-9D, which are schematic illustrations of extravascular devices 100 that are implanted around the outside of artery 20, in accordance with some applications of the present disclosure. For some applications, an extravascular device having three contact elements 102 (as shown in FIGS. 9A and 9C) is placed around the artery. Alternatively, the extravascular device has a different number of contact elements 102, e.g., four to six contact elements. The contact elements increase the strain in the arterial wall at the regions at which the contact elements contact the arterial wall, relative to the strain in the arterial wall in the absence of device 100. For some applications, the device increases the strain in the arterial wall even at regions of the arterial wall between the contact regions, relative to the strain of the arterial wall in the absence of the device.

As with the intravascular devices described hereinabove, typically contact between extravascular device 100 and the artery at a given longitudinal location is limited to several (e.g., three to six) contact regions around the circumference of the artery, and is generally minimized. Thus, when the device is placed around the artery there is at least one, and typically a plurality of, non-contact regions 104 around the circumference of the artery, at which the device does not contact the arterial wall. As shown in FIG. 9A, each contiguous non-contact region at a given longitudinal site of the artery, encompasses an angle theta around a longitudinal axis 76 of the artery. For some devices, as shown, the angle theta is also defined by the edges of adjacent contact elements 102 of the device and longitudinal axis 108 of the device. When the device is placed in the artery longitudinal axis 108 of the device is typically aligned with longitudinal axis 76 of the artery.

Typically, angle theta is greater than 10 degrees, e.g., greater than 20 degrees, or greater than 50 degrees. Further typically, angle theta is less than 180 degrees, e.g., less than 90 degrees. For some applications angle theta is 10-180 degrees, e.g., 20-90 degrees. This may be beneficial, since providing contiguous non-contact regions around the artery, as described, allows a greater area of the artery to pulsate in response to pressure changes than if the device were to provide smaller contiguous non-contact regions.

FIG. 9B shows a cross-section of one of contact elements 102 on a wall of artery 20, in accordance with some applications of the present disclosure. For some applications, some or all of contact elements 102 are shaped to define grooves. Each of the grooves has a length L. Typically, length L is more than 0.5 mm (e.g., more than 2 mm), and/or less than 8 mm (e.g., less than 6 mm). For example, length L may be 0.5-8 mm, e.g., 2-6 mm. The contact element typically facilitates pulsation of the arterial wall into the groove.

Typically (as shown for example in FIGS. 9A and 9C), extravascular device 100 does not encompass the full circumference of the artery. For example, the extravascular device may encompass less than 90 percent, e.g., less than 70 percent of the circumference of the artery. For some applications, using a device that does not encompass the whole circumference of the artery facilitates placement of the device on the artery. For example, it may be possible to place such a device on the artery (a) without dissecting the artery free from its surrounding tissues, and/or (b) without fully mobilizing the artery.

For some applications, using a device that does not encompass the whole circumference of the artery reduces damage to the artery, and/or damage to baroreceptors, during placement of the device on the artery. Alternatively or additionally, using a device that does not encompass the whole circumference of the artery makes placement of the device on the artery a less complex procedure than placement on the artery of a device that fully encompasses the artery.

For some applications, device 100 does not encompass the whole circumference of the artery, and contact elements 102 curve around the artery, as shown in FIG. 9C. Typically, the curvature of the contact elements facilitates coupling of device 100 to the artery.

Typically, extravascular device 100 encompasses more than 50 percent of the circumference of the artery, for example, in order to prevent the device from slipping from the artery. However, the scope of the present disclosure includes devices that encompass less than 50 percent of the artery.

For some applications, extravascular device 100 encompasses the whole circumference of artery 20. For example, an extravascular device may be used that comprises two pieces that are coupled to each other such that the device encompasses the whole artery.

Typically, the device causes an increase in the strain in at least a portion of the arterial wall, relative to the strain in the arterial wall in the absence of the device, without substantially reducing the cross-sectional area of the artery. For example, the cross-sectional area of the artery in the presence of device 100 may be more than 50 percent, e.g., more than 80 percent of the cross-sectional area of the artery in the absence of the device, at a given stage in the subject's cardiac cycle. The device does not cause a substantial reduction in the cross-sectional area of the artery because the device only contacts the artery at discrete points around the circumference of the artery. Therefore the device does not substantially constrict the artery, but rather reshapes the artery relative to the shape of the artery in the absence of the device.

Further typically, the device causes an increase in the strain in at least a portion of the arterial wall, relative to the strain in the arterial wall in the absence of the device, without substantially affecting blood flow through the artery. For example, the rate of blood flow through the artery in the presence of device 100 may be more than 70 percent, e.g., more than 90 percent of the blood flow in the absence of the device.

For some applications, an insubstantial effect on flow is achieved by maintaining an internal diameter of the artery, in the presence of the device, that is at least 30 percent of the diameter of the artery, in the absence of the device, throughout the cardiac cycle. Alternatively or additionally, an insubstantial effect on flow is achieved by maintaining the cross sectional area of the artery, in the presence of the device, to be at least 20 percent of the sectional area, in the absence of the device, at a given stage in the subject's cardiac cycle.

For some applications, the flow through the artery to which the device is coupled is monitored during the implantation of the device, and the device is configured to not reduce the flow by more than 15 percent. For some applications, the degree of force applied to the artery, and/or a physical distance between parts of the device, is modulated until the measured flow is not reduced by more than 15 percent. For some applications the absolute minimal distance across the artery is limited to no less than 1.5 mm.

For some applications, the extravascular devices contact the artery around which they are placed along a length of 5 mm.

For some applications, an extravascular device is used that is in accordance with one or more of the devices described in U.S. patent application Ser. No. 12/602,787 to Gross, which is incorporated herein by reference.

For some applications, a plurality of extravascular devices 100 are placed around the artery, as shown in FIG. 9D. For some applications, the plurality of extravascular devices are coupled to each other by a coupling element 105. The extravascular devices are typically spaced from each other such that there are non-contact regions 103 between each of the extravascular devices. Each of the non-contact regions is contiguous and, typically, has a length L1 of more than 0.5 mm (e.g., more than 2 mm), and/or less than 8 mm (e.g., less than 6 mm). For example, length L1 may be 0.5-8 mm, e.g., 2-6 mm. The arterial wall is typically able to pulsate at the non-contact regions.

Figure 10:
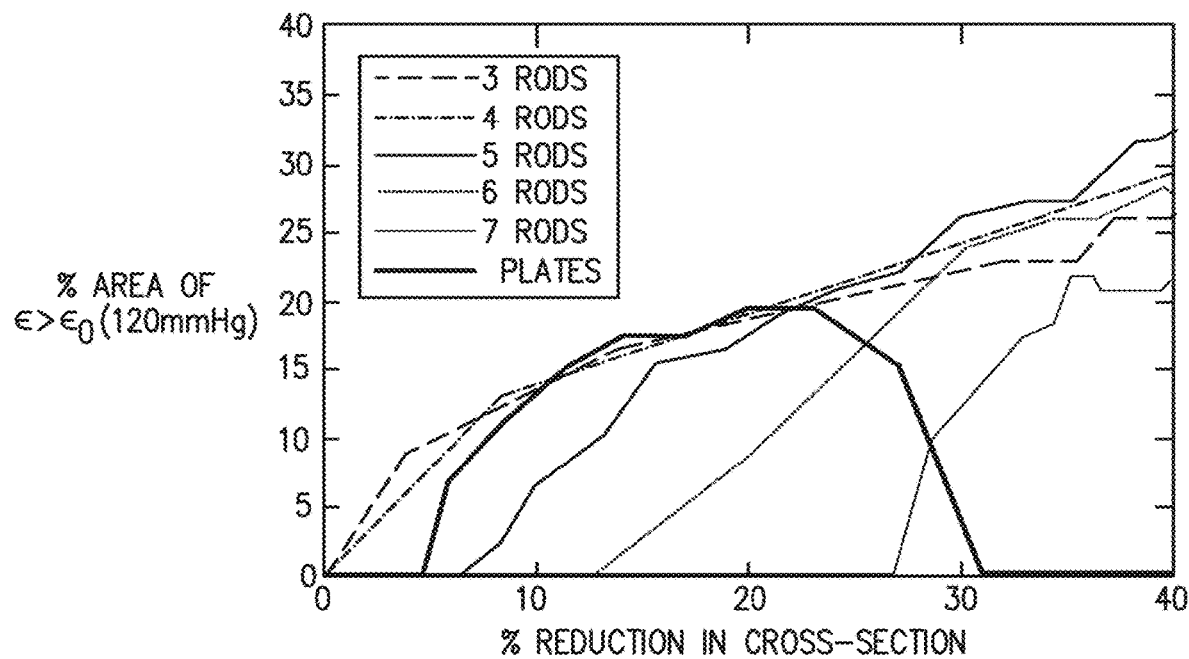
FIG. 10 is a graph that indicates the portion of an arterial wall having a strain that is greater than a threshold value, as a function of the reduction in the cross-sectional area of the artery, for respective extravascular devices, in accordance with some applications of the present disclosure.

Reference is now made to FIG. 10, which is a graph generated by computer simulation, which indicates the circumferential portion of an arterial wall having a strain that is greater than a threshold value, as a function of the reduction in the cross-sectional area of the artery, for respective extravascular devices. For some applications of the present disclosure, an extravascular device is placed around an artery, as described hereinabove. Typically, the extravascular device increases strain in at least regions of the arterial wall without substantially reducing the cross-sectional area of the artery, as described hereinabove. Further typically, the extravascular device increases strain in at least regions of the arterial wall without substantially affecting blood flow through the artery, as described hereinabove.

The graph shows several lines, the lines corresponding to extravascular devices that are similar to the extravascular device described hereinabove with reference to FIGS. 3 and 9A. The lines correspond to extravascular devices that have, respectively, three, four, five, six, and seven contact regions with the arterial wall around the circumference of the artery. In addition, one of the lines corresponds to two flat plates that are placed against the outer surface of the artery.

The simulation was generated for an artery at 100 mmHg of pressure. When the extravascular devices herein are placed on the arterial wall, the strain in at least some portions of the arterial wall is increased. Placing the extravascular devices on the arterial wall typically reduces the cross-sectional area of the artery. For a given device, the more the device compresses the artery, the greater the increase in the strain in the arterial walls, and the greater the reduction in the cross-sectional area of the artery.

The x-axis of the graph of FIG. 10 indicates the reduction in the cross-sectional area of the artery generated by the devices. The y-axis measures the percentage of the circumference of the arterial wall having a strain that is at least equivalent to what the strain of the arterial wall would be, if the pressure in the artery were 120 mmHg. Typically, the baroreceptor firing rate in such areas when the pressure is 100 mmHg, during use of the devices described hereinabove, will be generally equivalent to, or greater than the baroreceptor firing rate at 120 mmHg pressure in the absence of use of the devices. Thus, each of the lines in the graph is a measure of the percentage of the circumference of the arterial wall having the increased strain as a function of the reduction in the arterial cross-sectional area that is necessary to induce the increase in strain.

It may be observed that the devices having a smaller number of contact regions with the artery are typically more effective at increasing the strain in the arterial wall by applying a compression force that does not substantially reduce the cross-sectional area of the artery. For example, devices having three and four contact regions with the artery increase the strain of, respectively, 13 percent and 14 percent of the arterial wall to the equivalent of 120 mmHg of pressure while only reducing the cross-sectional area of the artery by 10 percent. Typically, a 10 percent reduction in the cross-sectional area of the artery does not substantially reduce blood flow through the artery in a manner that has significant adverse physiological effects.

The inventors hypothesize that the devices having a larger number of contact regions with the artery are less effective at increasing the strain in the arterial wall than those with a smaller number of contact regions, because the device acts to support the arterial wall at the contact regions, thereby reducing pulsation of the arterial wall over the course of the cardiac cycle. For this reason, the inventors hypothesize that, at low pressures, the two plates are relatively effective at increasing the strain in the arterial wall, since there is a small amount of contact between the plates and the wall. However, at higher compressive forces, the plates provide more support to the wall since there is a greater contact area between the plates and the wall. Therefore, the plates limit the pulsation of the wall by an increasing amount. At higher compressive forces, the decrease in baroreceptor stimulation due to the reduced pulsation of the artery overrides the increase in baroreceptor stimulation due to the plates exerting pressure on the arterial wall. Thus, at higher compressive forces, the plates are not as effective as the other extravascular devices at increasing the strain in regions of the arterial wall. Nevertheless, the scope of the present disclosure includes the use of such plates, e.g., when strain increase is not the only parameter of importance in selecting an implant.

It is additionally noted that for a broad range of allowed reductions in cross-section, e.g., about 17-30 percent, 3-6 contact regions all function generally well. Thus, at higher compression forces (i.e., by reducing the cross-sectional area of the artery by a greater amount), the devices having a greater number of contact regions with the artery become more effective at increasing the strain in the arterial wall. For example, by reducing the cross-sectional area of the artery by 30 percent, each of the devices having three to six contact regions with the artery increases the strain of between 22 percent and 26 percent of the arterial wall to the equivalent of 120 mmHg of pressure.

Figure 11:
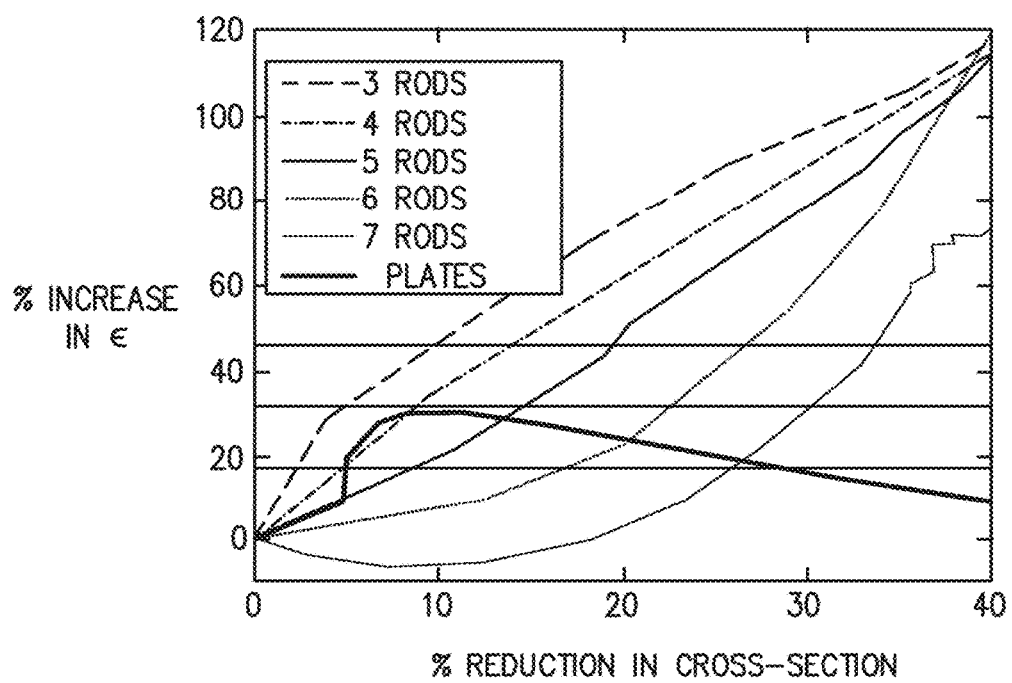
FIG. 11 is a graph showing the maximum percentage increase in the strain of the arterial wall as a function of the reduction in the cross-sectional area of the artery, for respective extravascular devices, in accordance with some applications of the present disclosure.

Reference is now made to FIG. 11, which is a graph showing the maximum percentage increase in the strain of the arterial wall as a function of the reduction in the cross-sectional area of the artery, for respective extravascular devices.

The graph shows several lines, the lines corresponding to extravascular devices that are similar to the extravascular device described hereinabove with reference to FIGS. 3 and 9A. The lines correspond to extravascular devices that have, respectively, three, four, five, six, and seven contact regions with the arterial wall around the circumference of the artery. In addition, one of the lines corresponds to two plates that are placed against the outside surface of the artery.

The simulation was generated for an artery at 100 mmHg of pressure. The bottom, middle, and top horizontal lines correspond, respectively, to the maximum strain in the vessel wall at 120 mmHg, 140 mmHg, and 160 mmHg pressure, when no device is placed on the artery. When the devices herein are placed on the arterial wall, the maximum strain of the arterial wall is increased. Placing the devices on the arterial wall typically reduces the cross-sectional area of the artery. For a given device, the more the device compresses the artery, the greater the maximum strain in the arterial walls, and the greater the reduction in the cross-sectional area of the artery.

The x-axis of the graph of FIG. 11 measures the reduction in the cross-sectional area of the artery generated by the devices. The y-axis measures the maximum strain in the arterial wall.

It may be observed that for the devices for which the data shown in the graph was generated, the fewer the number of contact regions that the device made with the arterial wall, the more effective the device is at increasing the maximum strain in the arterial wall for a given reduction in the cross-sectional area of the artery that is caused by the device. For example, by compressing the artery such that it has a 20 percent reduction in its cross-sectional area:

the device having three contact regions generates a maximum increase of 75 percent in the arterial wall strain, the device having four contact regions generates a maximum increase of 62 percent in the arterial wall strain, the device having five contact regions generates a maximum increase of 50 percent in the arterial wall strain, the device having six contact regions generates a maximum increase of 23 percent in the arterial wall strain, and the device having seven contact regions generates a maximum increase of less than 5 percent in the arterial wall strain.

Thus, in accordance with some applications of the present disclosure, extravascular devices having three or more contact regions (e.g., three to six) with the artery are placed around the outside of the artery. The devices typically provide contact regions and non-contact regions of the arterial wall, as described hereinabove. The devices typically increase the strain in the arterial wall, thereby generating increased baroreceptor firing in the artery.

Figure 12:
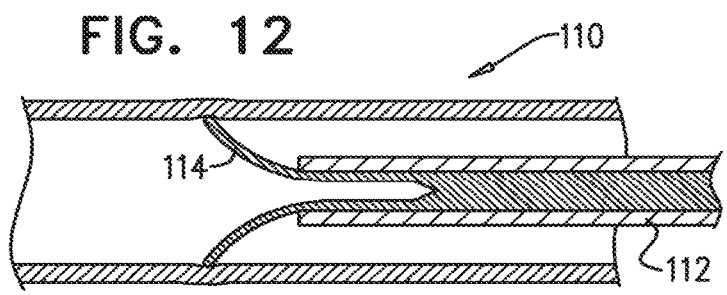
FIG. 12 is a schematic illustration of a device for measuring the baroreceptor response of a subject to pressure that is exerted on the inner wall of an artery of the subject, in accordance with some applications of the present disclosure.

Reference is now made to FIG. 12, which is a schematic illustration of a device 110 that is used to test the baroreceptor response of a subject to a range of intravascular pressures, in accordance with some applications of the present disclosure. For some applications, before an intravascular device is inserted into a subject's artery, the baroreceptor response of the subject is tested using measuring device 110. Cather 112 is inserted into artery 20, in which the intravascular device will be implanted. Extendable arms 114 are extendable from the distal end of the catheter, and are configured such that the pressure that the arms exert on the arterial wall increases, as the portion of the arms that extends from the catheter increases.

Extendable arms 114 are extended incrementally from the distal end of the catheter. At each of the increments, the subject's blood pressure is measured in order to determine the baroreceptor response to the pressure that the arms are exerting on the arterial wall. On the basis of the blood pressure measurements, it is determined which intravascular device should be inserted into the subject's artery, and/or what dimensions the intravascular device should have.

For some applications, a measuring device including arms 114 or a similar measuring device is left in place in the artery, but catheter 112 is removed before the blood pressure measurements are taken. For example, the catheter may be removed in order to increase blood flow through the artery, relative to when the catheter is in place. Once it has been determined, using the measuring device, which intravascular device should be placed inside the artery, and/or what dimensions the intravascular device should have, the measuring device is removed from the artery and the intravascular device is placed inside the artery.

For some applications, a toroid balloon is placed inside the artery and is used as a measuring device. The balloon is inflated incrementally such that the balloon applies varying amounts of pressure to the arterial wall, and the subject's blood pressure is measured in order to measure the response to the pressure being applied to the wall. In this manner, it is determined which intravascular device should be used, and/or what dimensions the intravascular device should have. During the aforementioned measuring procedure, blood continues to flow through the artery, via a central hole in the toroid balloon.

For some applications, the intravascular devices described herein are inserted to an implantation site inside or (using a non-transvascular route) outside of the subject's artery, while the device is in a first configuration thereof. When the device has been placed at the implantation site, the configuration of the device is changed to a second configuration, in which the device is effective to increase baroreceptor stimulation, in accordance with the techniques described herein. For example, the device may be made of nitinol, or another shape memory material, and the configuration of the device may be changed by applying an RF signal, and/or another form of energy, to the device. For some applications, the device is implanted at an implantation site that is close to the subject's skin, and the RF signal is applied to the device via the subject's skin.

For some applications, devices are applied to the carotid artery of a subject who suffers from carotid sinus hypersensitivity, in order to reduce baroreceptor sensitivity of the carotid sinus, by reducing pulsation of the artery. For example, a device may be placed inside or outside the artery such that the device makes contact with the artery at more than six contact points, and/or over more than 180 degrees of the circumference of the artery. For some applications, a device (e.g., a stent) is placed inside or outside of the artery such that the device makes 270-360 degrees of contact with the artery.

Figure 13:
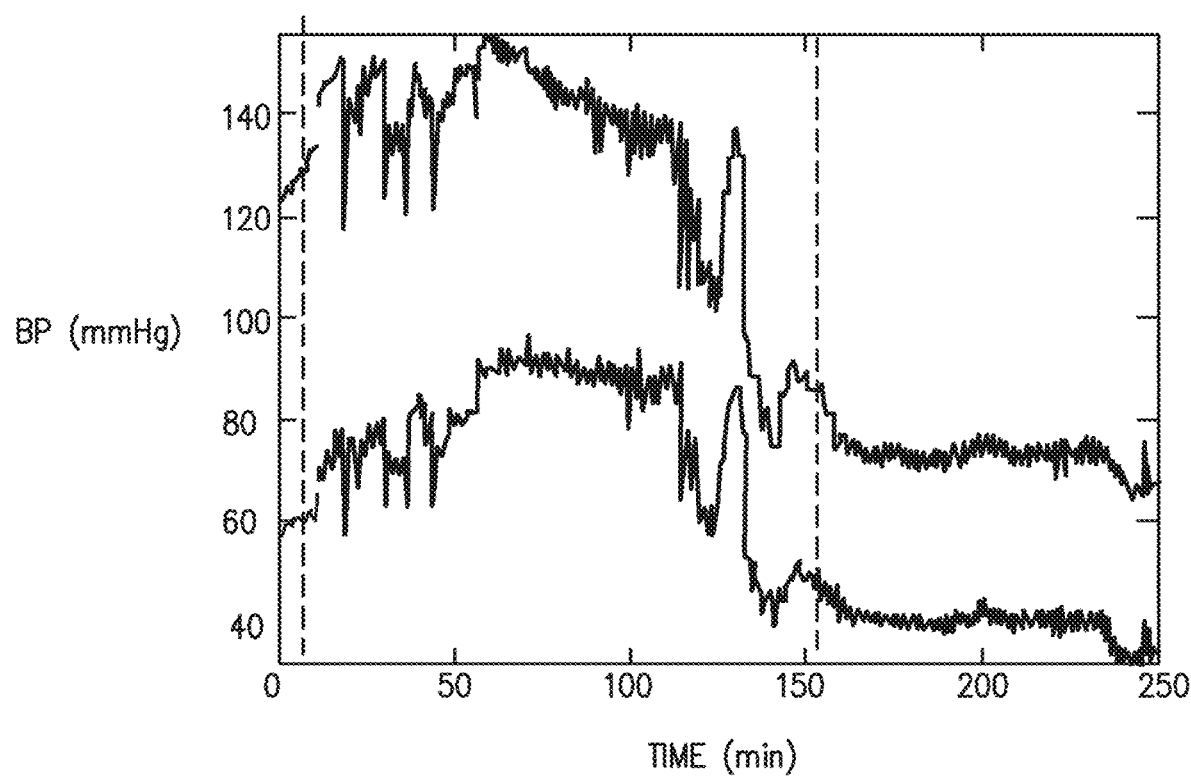
FIG. 13 is a graph showing the blood pressure measured in a dog before and after the insertion of intravascular devices into the dog's carotid sinuses, in accordance with some applications of the present disclosure.

Reference is now made to FIG. 13, which is a graph showing blood pressure measured in a dog, before, during and after the bilateral placement of intravascular devices into the dog's carotid sinuses, in accordance with some applications of the present disclosure. Intravascular devices which made contact with the carotid sinus at four contact regions (the devices being generally as shown in FIGS. 7A-B) were placed in the dog's left and right carotid sinuses. The beginning and end of the implantation period is indicated in FIG. 13 by, respectively, the left and right vertical dashed lines at about five minutes and 153 minutes.

It may be observed that the implantation of the devices in both sinuses resulted in the dog's systolic blood pressure dropping from above 120 mmHg to below 80 mmHg, and in the dog's diastolic blood pressure dropping from about 60 mmHg to about 40 mmHg. During the implantation procedure the dog's blood pressure rose. The inventors hypothesize that the rise in blood pressure is due to catheters blocking the flow of blood to the carotid arteries during the implantation, resulting in reduced baroreceptor stimulation during the implantation procedure. It is noted that the placement of the device in the dog's sinuses did not have a substantial effect in the dog's heart rate.

Figure 14:
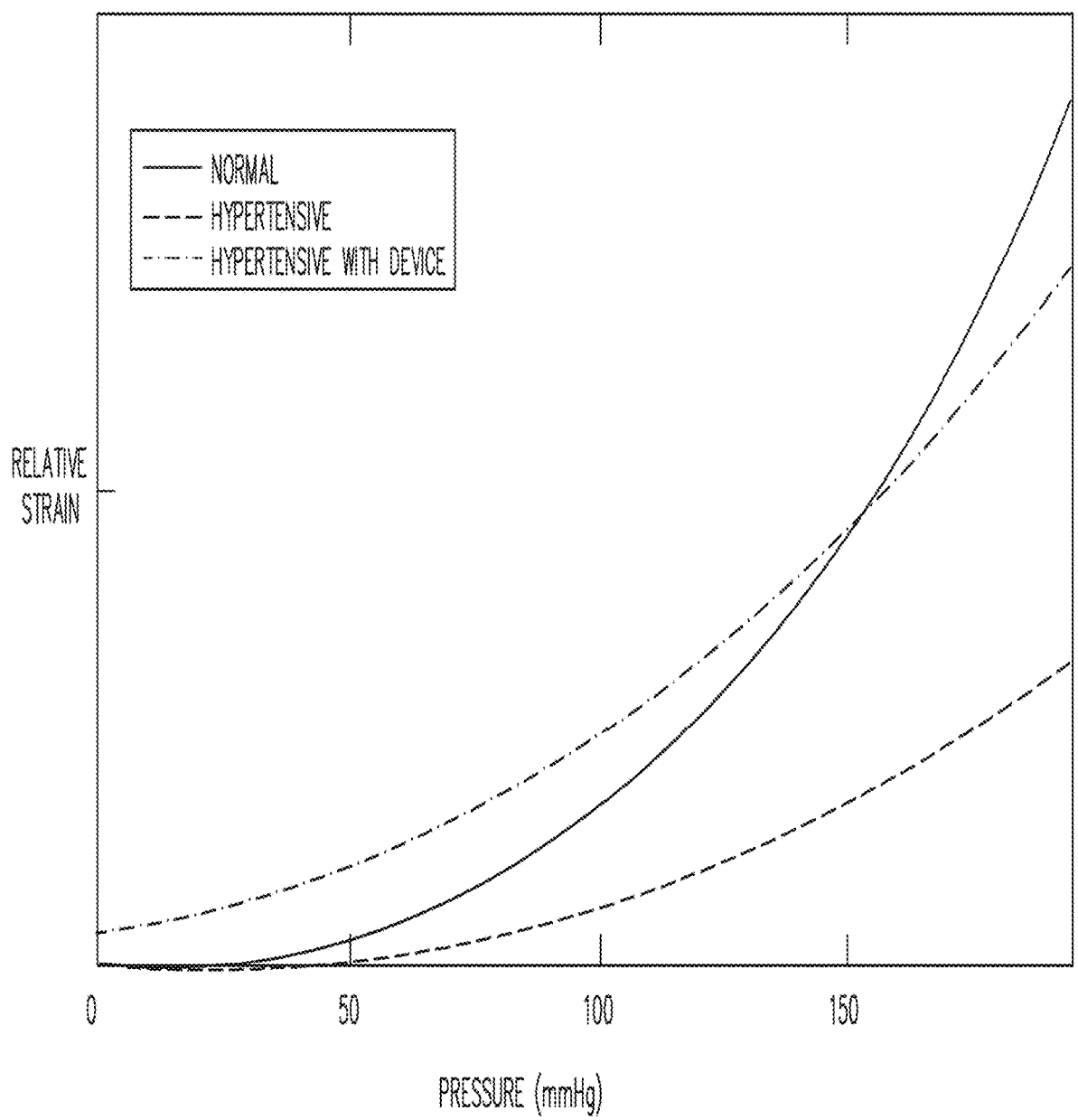
FIG. 14 is a graph showing the pressure-strain curve of the artery of a healthy subject, a hypertensive subject, and a hypertensive subject that uses a device as described herein, in accordance with some applications of the present disclosure.

Reference is now made to FIG. 14, which is a graph showing the pressure-strain curve of an artery of a normal subject, a hypertensive subject, and a hypertensive subject who uses one of the devices described herein. One of the causes of hypertension is that the arterial wall of the subject does not experience as much strain at any given pressure, as the arterial wall of a normal subject. Thus, the pressure-strain curve of the hypertensive subject is flattened with respect to that of a healthy subject and the strain response is shifted to higher pressures.

The devices described herein increase the strain in the arterial wall at all pressure levels within the artery. For some applications, as shown, at increasing arterial pressures, the absolute increase in the strain in the arterial wall caused by the device increases, relative to the strain experienced by the hypertensive subject before implantation of the device. Thus, the devices described herein both shift the pressure-strain curve of a hypertensive subject upwards and increase the gradient of the curve. A device is typically selected such that the subject's pressure-strain curve, subsequent to implantation of the device, will intersect the normal pressure-strain curve at a pressure of between 80 mmHg and 240 mmHg.

Figure 15A:
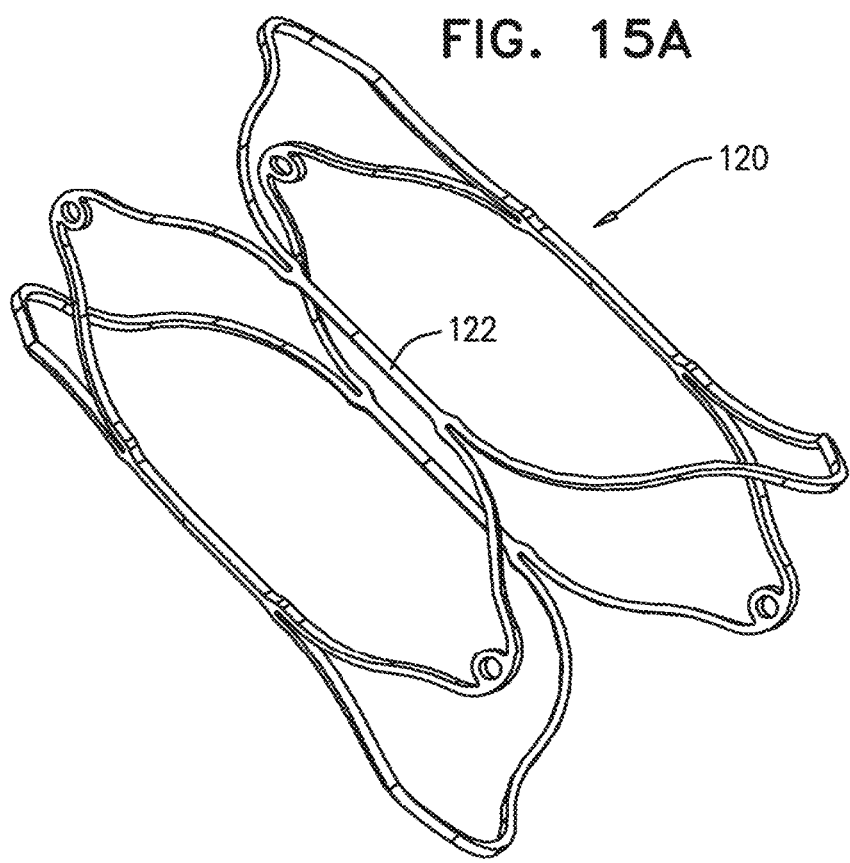
FIGS. 15A-15B, and 15E are schematic illustrations of a device for placing in a subject's artery, in accordance with some applications of the present disclosure.
Figure 15B:
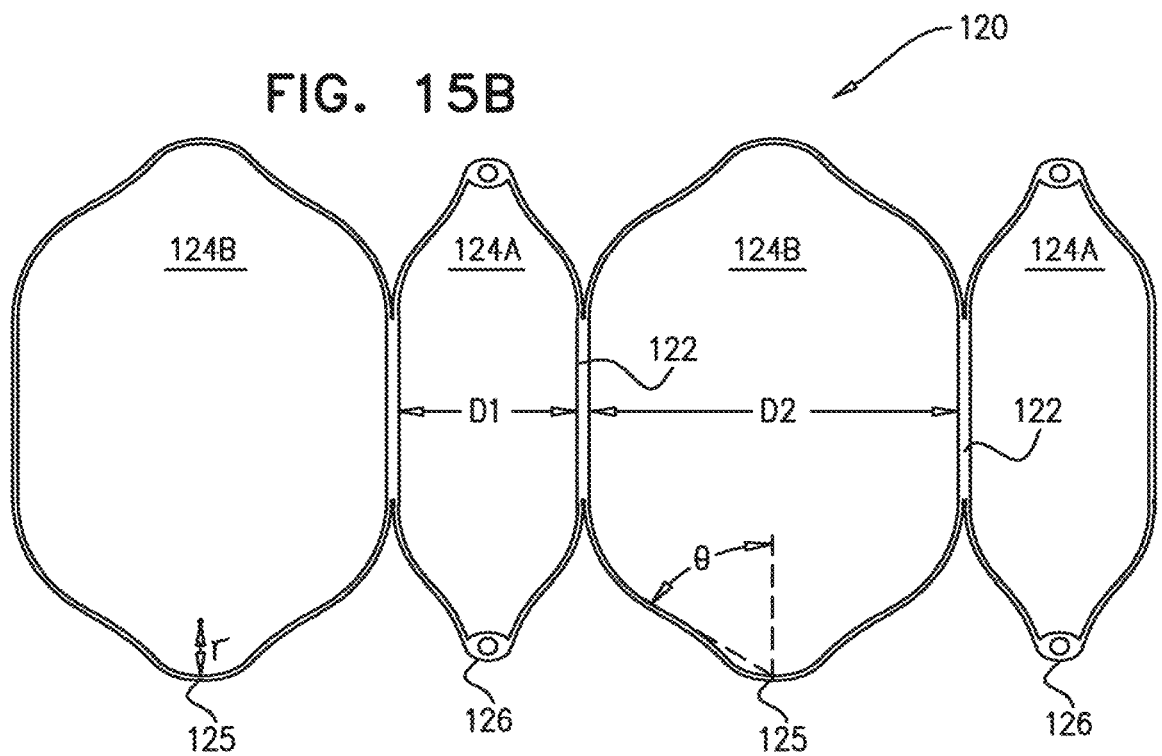

Reference is now made to FIGS. 15A-15B, which are schematic illustrations of a device 120 for placing in artery 20, in accordance with some applications of the present disclosure. Device 120 is generally similar to the intra-arterial devices described hereinabove, except for the differences described hereinbelow. FIG. 15A shows a three-dimensional view of device 120, as the device is shaped when the device is inside the artery, and FIG. 15B shows a flattened, opened, profile of device 120. Device 120 is generally similar to device 80 described hereinabove with reference to FIGS. 7A-7B. Device 120 contacts the wall of the artery at four contact regions 122 (which comprise strut portions), thereby flattening the non-contact regions of the artery that are between the contact regions. For some applications, device 120 includes radiopaque markers 126 at proximal and distal ends of the device (as shown) or at other portions of the device.

As shown in FIG. 15B, each of the strut portions is generally spaced from its two adjacent strut portions by respective distances D1 and D2, D1 being smaller than D2. Thus, the device defines a first set of two sides 124A, having widths D1, and a second set of two sides 124B, having widths D2. Placement of device 120 inside artery 20 typically results in the artery having a cross-sectional shape that is more rectangular than in the absence of the device, the cross-sectional shape having sides with lengths D1 and D2. Each of the sides of the cross-sectional shape is supported by a respective side 124A or 124B of device 120. Typically, the ratio of distance D2 to distance D1 is greater than 1:1, e.g., greater than 2:1, and/or less than 5:1, e.g., between 1.1:1 and 5:1 (e.g., between 1.5:1 and 3:1).

An experiment was conducted by the inventors of the present application in which a spring constant of a device having generally similar characteristics to device 120 was measured. For the purposes of the experiment, the spring constant of the device was measured by measuring the change in force applied by the device versus the change in the diameter of the device during cycles of crimping and expansion of the device. A plot of the force versus the diameter of the device during such a cycle forms a hysteresis curve. It is noted that, subsequent to implantation of the device in a subject's artery, the variation in force versus diameter that the device undergoes during a characteristic cardiac cycle also forms a hysteresis curve. When the device is implanted, the maximum force that the device exerts on the arterial wall, which generates the loading branch of the hysteresis curve, is exerted during diastole. The minimum force that the device exerts on the artery, which generates the unloading branch of the hysteresis curve, is exerted during systole. In the experiment that was conducted by the inventors, the spring constant of the device was determined based upon measurements that were performed using an M250-3 CT Materials Testing Machine manufactured by The Testometric Company Ltd. (Lancashire, UK). The device had a spring constant of 1.14 N/mm. In accordance with the aforementioned experimental result, in accordance with some applications of the disclosure, a device is inserted into a subject's artery in accordance with the techniques described herein, the device having a spring constant of less than 2 N/mm, e.g., less than 1.5 N/mm, or less than 1.3 N/mm.

Typically, at the distal and proximal ends of device 120, the device is shaped to define crimping arches 125. During transcatheteral insertion of the device into the subject's artery, the device is crimped about the crimping arches, such that the span of the device is reduced relative to the span of the device in its expanded state. Upon emerging from the distal end of the catheter, the device expands against the arterial wall.

For some applications, each crimping arch 125 has a radius of curvature r that is less than 6 mm (e.g., less than 1 mm), in order to facilitate crimping of device 120 about the crimping arch. For some applications, each crimping arch has a radius of curvature r that is greater than 0.3 mm, since a crimping arch having a smaller radius of curvature may damage the arterial wall. Furthermore, when the expanded device exerts pressure on the arterial wall, much of the pressure that is exerted on the device by the arterial wall is resisted by the crimping arches. Therefore, for some applications, each crimping arch has a radius of curvature that is greater than 0.3 mm, in order to facilitate resistance to the pressure that is exerted on the device at the crimping arches. Therefore, for some applications, each crimping arch has a radius of curvature that is 0.3-0.6 mm.

For some applications, the thickness of the struts of device 120 at the crimping arches is greater than the thickness of the struts at other portions of the device, in order to facilitate resistance to the pressure that is exerted on the device at the crimping arches. For some applications, there are additional regions of the struts that are susceptible to absorbing much of the pressure that is exerted on the device by the arterial wall, and the thickness of the struts at the additional regions is greater than the thickness of the struts at other portions of the device.

Figure 15C:
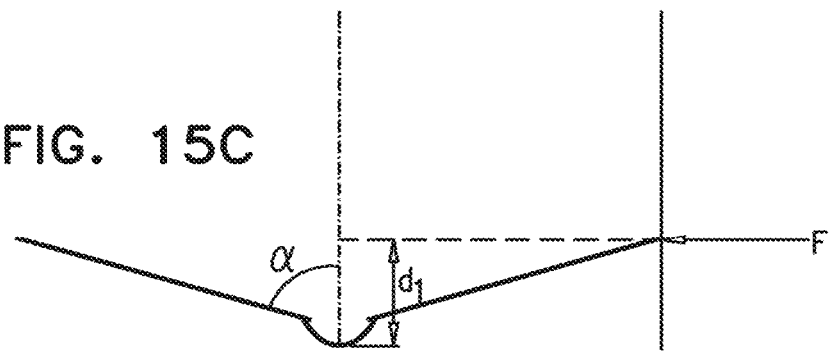
FIGS. 15C-15D are schematic illustrations of an arterial wall exerting a force on struts of a device, in accordance with some applications of the present disclosure.
Figure 15D:
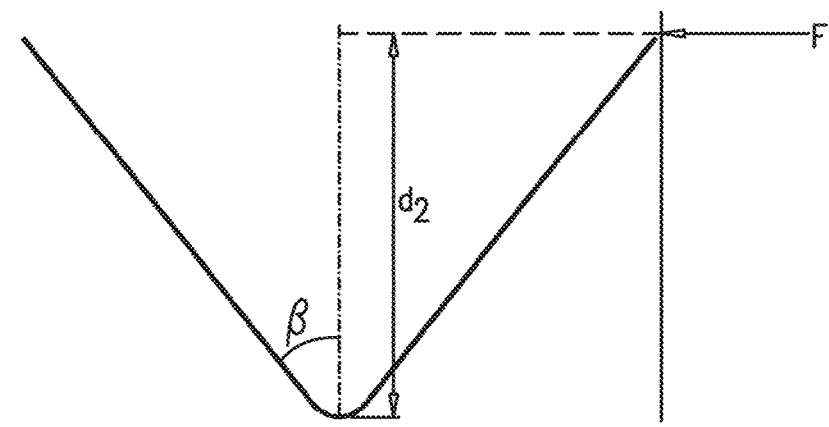

Typically, when device 120 is in a non-constrained state thereof, the strut portions of device 120 project outwardly from crimping arch 125 at an angle theta, angle theta being greater than 30 degrees, e.g., greater than 60 degrees, or greater than 75 degrees. Typically, the outward projection of the struts from the crimping arch at such an angle reduces the moment that the arterial wall exerts about the crimping arch, relative to if the struts projected outwardly from the crimping arch at a smaller angle. This is demonstrated with reference to FIGS. 15C-15D, which show a force F of the arterial wall being exerted on struts that project outwardly, respectively, at angles of alpha and beta, alpha being greater than beta. In FIG. 15C, the force is exerted on the strut at a distance d1 from the crimping arch, and in FIG. 15D, the force is exerted on the strut at a distance d2 from the crimping arch, d1 being less than d2. Therefore, the moment that is exerted about crimping point 125 for the strut shown in FIG. 15C is less than that of FIG. 15D.

Figure 15E:
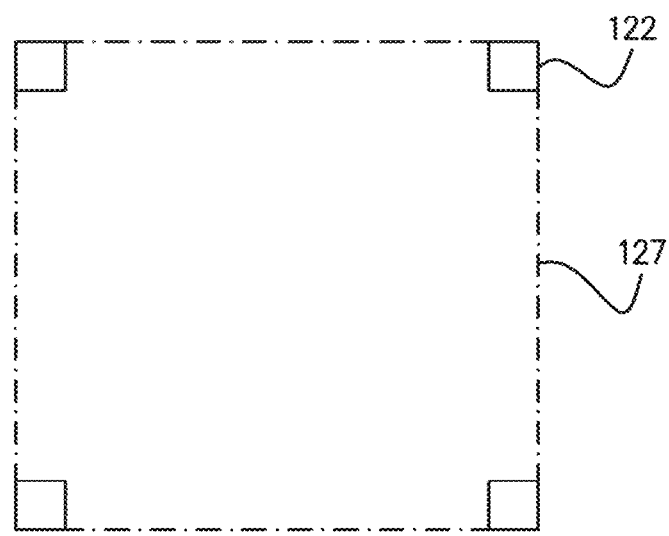

Typically, as a result of angle theta being greater than 30 degrees, e.g., greater than 60 degrees, or greater than 75 degrees, when in the non-constrained state, the perimeter of the cross-section of device 120 at any location along the length of the device is more than 80% (e.g., more than 90%) of the maximum perimeter of the cross-section of the device along more than 80% (e.g., more than 90%) of the length of the device. Conversely, if angle theta were smaller, the perimeter of the cross-section of device 120 would be more than 80% of the maximum perimeter of the cross-section of the device along less than 80% of the length of the device. It is noted that the perimeter of the cross-section of the device at any location along the length of the device is defined as the line that bounds the solid components (e.g., the struts) of device 120 at the location. This is demonstrated with reference to FIG. 15E, which shows a dotted line indicating the perimeter of the cross-section of the device. Further typically, as a result of angle theta being greater than 30 degrees, e.g., greater than 60 degrees, or greater than 75 degrees, the ratio of the perimeter of the cross-section of device 120 to the cross-sectional area of the solid components of the device is more than is more than 80% (e.g., more than 90%) of the maximum value of this ratio along more than 80% (e.g., more than 90%) of the length of the device.

Reference is now made to FIGS. 16A-16D, which are schematic illustrations of another device 130 for placing in artery 20, in accordance with some applications of the present disclosure. Device 130 is generally similar to the intra-arterial devices described hereinabove, except for the differences described hereinbelow. FIGS. 16B-16D show device 130 during the shaping of the device, the device typically being placed on a shaping mandrel 132 during the shaping process. As shown, the cross-sectional shape of intra-arterial device 130 varies along the longitudinal axis of the device. Typically, the device defines strut portions 134, all of which diverge from each other, from a first end of the device to the second end of the device. For some applications, each strut portion includes two or more parallel struts, as described hereinbelow.

As shown in FIGS. 16C-16D, device 130 is shaped such that at the second end of the device, the device has a greater span S2, than the span of the device S1 at the first end of the device. Typically, the ratio of S2 to S1 is greater than 1:1, e.g., greater than 1.1:1, and/or less than 2:1, e.g., between 1.1:1 and 2:1 (e.g., between 1.1:1 and 1.4:1).

For some applications, devices are inserted into a subject's artery that are shaped differently from device 130, but which are also shaped such that at the second end of the device, the device has a greater span S2, than the span of the device S1 at the first end of the device, for example, as described with reference to FIGS. 18A-18D.

Due to the ratio of S2 to S1, upon placement of device 130 inside the artery, the shape of the artery typically becomes increasingly non-circular (e.g., elliptical or rectangular), along the length of the artery, from the first end of the device (having span S1) to the second end of the device (having span S2). Furthermore, due to the ratio of S2 to S1, upon placement of device 130 inside the artery, the cross-sectional area of the artery typically increases along the length of the artery, from the first end of the device (having span S1) to the second end of the device (having span S2). Typically, the device is placed such that the first end of the device (which has the smaller span) is disposed within the internal carotid artery, and the second end of the device (which has the greater span) is disposed in the vicinity of the carotid bifurcation. In this configuration, the device thus stretches the internal carotid artery in the vicinity of the bifurcation, due to the span of the device at the second end of the device, but does not substantially stretch the internal carotid artery downstream of the bifurcation.

Typically, the device is shaped such that the device can be viewed as defining three zones along the length of the device. The second end may be viewed as the maximum-span zone, which is configured to be placed in the common carotid artery and/or within the internal carotid artery in the vicinity of the carotid bifurcation. The first end may be viewed as the minimum-span zone, which is configured to be placed at a location within the internal carotid artery that is downstream of the bifurcation and to reduce strain on the internal carotid artery at the downstream location relative to if the minimum-span zone had a greater span. The portion of the device between the first and second zones may be viewed as the pulsation zone, at which the device exerts strain on the artery, while facilitating pulsation of the artery by having non-contact regions at which the device does not contact the artery. It is noted that, for some applications, the second end (i.e., the maximum-span zone) is configured to be placed downstream of the carotid bifurcation, but to cause stretching of the carotid artery in the vicinity of the carotid bifurcation, due to the span of the device at the second end.

As shown in FIGS. 16C-16D, device 130 is shaped such that in the vicinity of the second end of the device, the device has a greater span S2 in a first direction than a span S3 of the device in a second direction. For some applications, the ratio of S2 to S3 is greater than 1:1, e.g., greater than 2:1, and/or less than 5:1, e.g., between 1.1:1 and 5:1 (e.g., between 1.5:1 and 3:1). Typically, the ratio of S2 to S3 enhances flattening of the artery in which device 130 is placed in the direction of span S2.

Typically, device 130 includes three or more diverging strut portions 134, e.g., four diverging strut portions, as shown. For some applications, device 130 includes crimping arches 125 at the ends of the device, the crimping arches being generally similar to crimping arches 125, as described hereinabove with reference to device 120. For some applications, the strut portions of device 130 project outwardly from crimping arches 125 at an angle theta, angle theta being greater than 30 degrees, e.g., greater than 60 degrees, or greater than 75 degrees, in a generally similar manner to that described with reference to device 120. For some applications, each of the strut portions comprises two struts that are translated longitudinally with respect to one another (i.e., the struts are doubled), in order to provide mechanical strength to the struts. Alternatively, each strut portion includes a single strut, or more than two struts that are translated longitudinally with respect to each other.

Figure 17A:
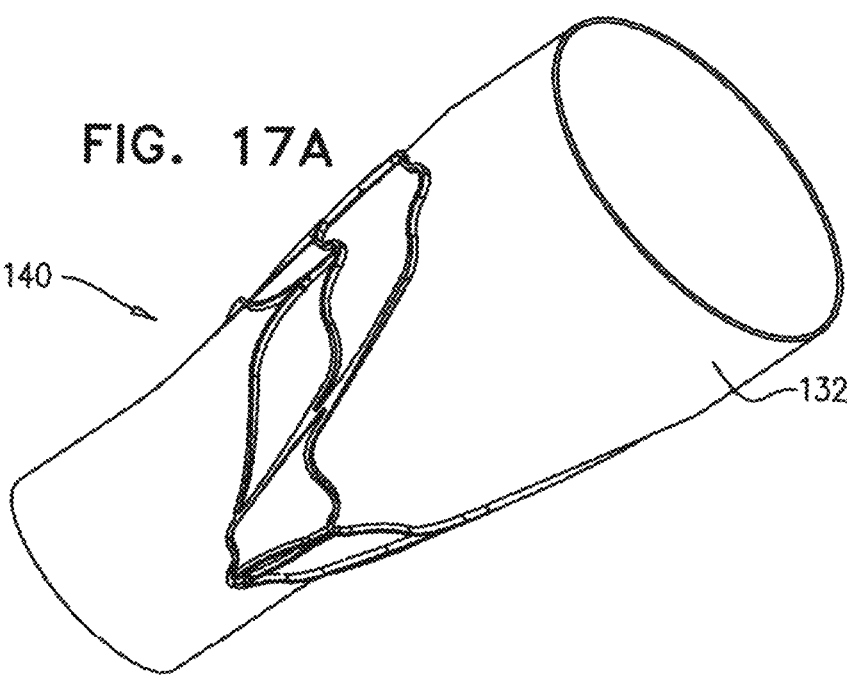
FIGS. 17A-17D are schematic illustrations of yet another device for placing in a subject's artery, in accordance with some applications of the present disclosure.

Reference is now made to FIGS. 17A-17D, which are schematic illustrations of yet another device 140 for placing in artery 20, in accordance with some applications of the present disclosure. Device 140 is generally similar to the intra-arterial devices described hereinabove, except for the differences described hereinbelow. FIG. 17A shows device 140 during the shaping of the device, the device typically being placed on shaping mandrel 132 during the shaping process. As shown, the cross-sectional shape of intra-arterial device 140 varies along the longitudinal axis of the device.

Figure 17B:
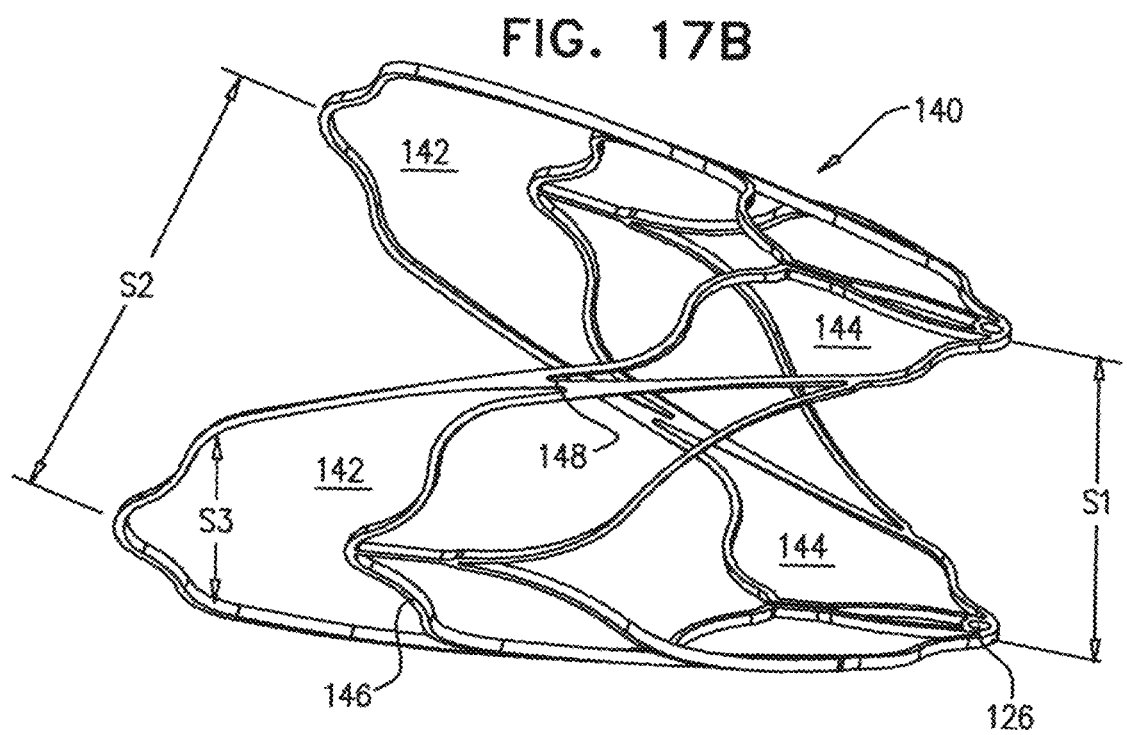

As shown in FIG. 17B, device 140 is shaped such that at the second end of the device, the device has a greater span S2, than the span of the device S1 at the first end of the device. Typically, the ratio of S2 to S1 is greater than 1:1, e.g., e.g., greater than 1.1:1, and/or less than 2:1, e.g., between 1.1:1 and 2:1 (e.g., between 1.1:1 and 1.4:1).

Due to the ratio of S2 to S1, upon placement of device 140 inside the artery, the shape of the artery typically becomes increasingly non-circular (e.g., elliptical or rectangular), along the length of the artery, from the first end of the device (having span S1) to the second end of the device (having span S2). Furthermore, due to the ratio of S2 to S1, upon placement of device 130 inside the artery, the cross-sectional area of the artery typically increases along the length of the artery, from the first end of the device (having span S1) to the second end of the device (having span S2). Typically, the device is placed such that the second end of the device (which has the greater span) is disposed in the common carotid artery and/or within the internal carotid artery in the vicinity of the carotid bifurcation and the first end of the device (which has the smaller span) is disposed within the internal carotid artery downstream of the bifurcation. In this configuration, the device thus stretches the internal carotid artery in the vicinity of the bifurcation, due to the span of the device at the second end of the device, but does not substantially stretch the internal carotid artery downstream of the bifurcation.

Device 140 is shaped to define four sides. Two of the sides, which are opposite to one another, are configured to act as artery contact regions 142 (shown in FIG. 17C), and apply pressure to the walls of the artery by contacting the artery. The other two sides of device 140, which are also opposite to one another, are configured to act as crimping regions 144 (shown in FIG. 17D). During transcatheteral implantation of the device into the artery, the crimping regions facilitate crimping of the device.

It is noted that the sides of device 140 that act as artery contact regions 142 are typically also somewhat crimpable. Typically, as shown, the sides of device 140 that act as artery contact regions 142 include crimping arches 125 (as described hereinabove), which facilitate crimping of the device.

Figure 17C:
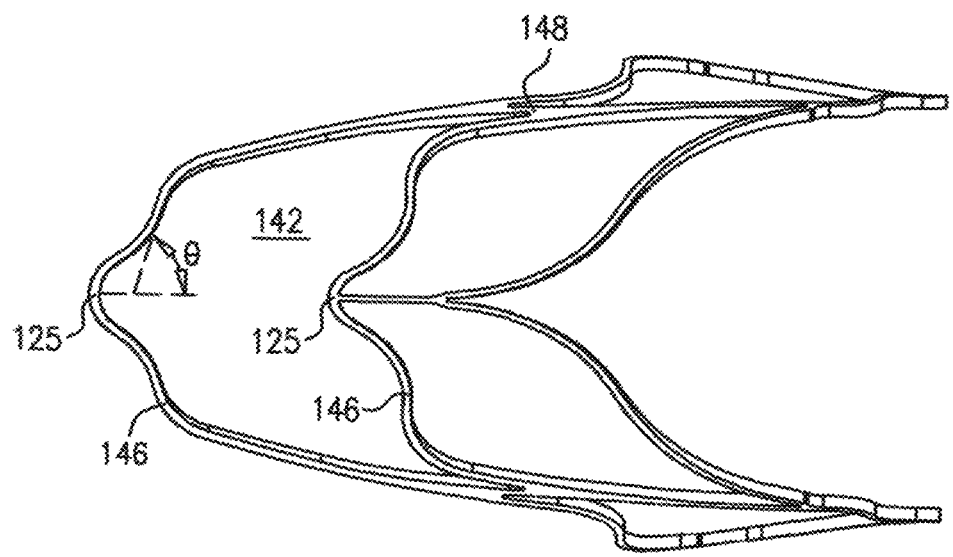

An artery contacting region 142 of device 140 is shown in FIG. 17C. Upon implantation inside an artery, artery contact regions 142 exert pressure on the artery wall, thereby flattening regions of the arterial wall between the artery contact regions, and increasing the strain in the arterial wall at the flattened regions, as described hereinabove. For some applications, the artery contact regions comprise two or more struts 146 that are translated longitudinally with respect to one another. Typically, the struts of a given artery contact region are coupled to one another by a reinforcing element 148. For some applications, the reinforcing element is disposed such that when the artery contact region is crimped, the longitudinal translation of the struts with respect to one another is maintained. For some applications, struts 146 of device 140 project outwardly from crimping arches 125 at an angle theta, angle theta being greater than 30 degrees, e.g., greater than 60 degrees, or greater than 75 degrees, in a generally similar manner to that described with reference to device 120.

Figure 17D:
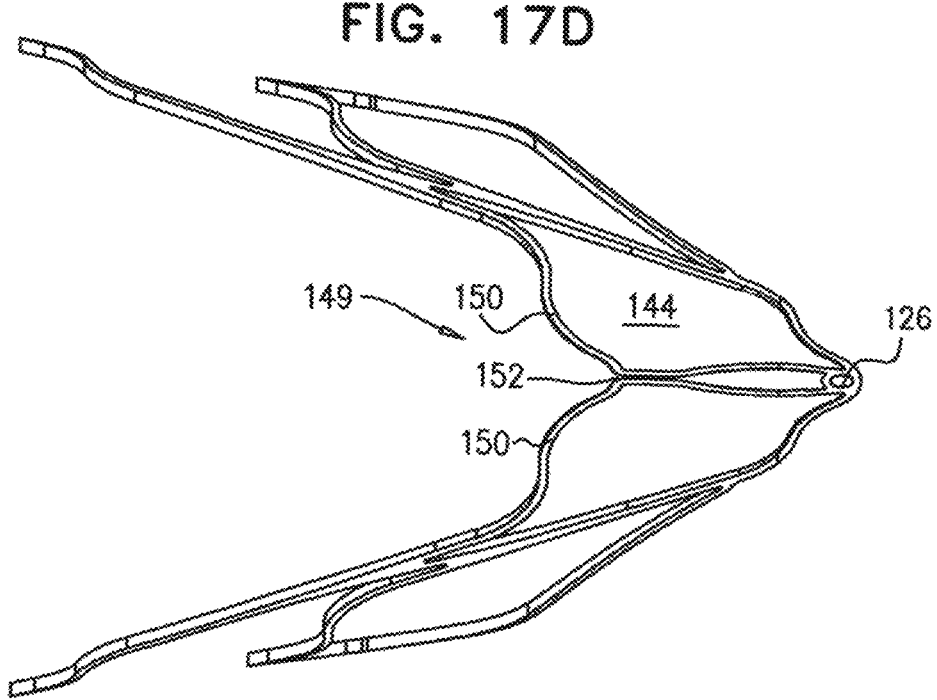

A crimping region 144 of device 140 is shown in FIG. 17D. For some applications, crimping region 144 comprises a locking mechanism 149. During crimping of the device, the locking mechanism is unlocked, to facilitate crimping of the device. When the device is implanted into artery 20, the locking mechanism is locked, so as to prevent the crimping regions from becoming crimped due to pressure that is exerted on the device by the artery. For example, the locking mechanism may comprise two struts 150 that are shaped so as to become locked in placed with respect to one another at a locking interface 152. In order to crimp the device, one of the struts is forced above or below the plane of the locking interface. The struts are pre-shaped, such that when the struts are not locked with respect to one another, the struts move toward one another, such that the struts at least partially overlap with one another. Alternatively or additionally, other locking mechanisms are used. For example, a hinged-based mechanism may be used.

For some applications, device 140 is configured to be at least partially crimpable about the crimping regions even when the device is placed inside the artery. The crimping regions thus facilitate flexing of device 140 when the device is placed inside the artery. For example, the crimping regions may facilitate passive flexing of the device in coordination with the subject's cardiac cycle, due to variations in the pressure that is exerted on the device by the arterial walls, over the course of the cardiac cycle.

Figure 18A:
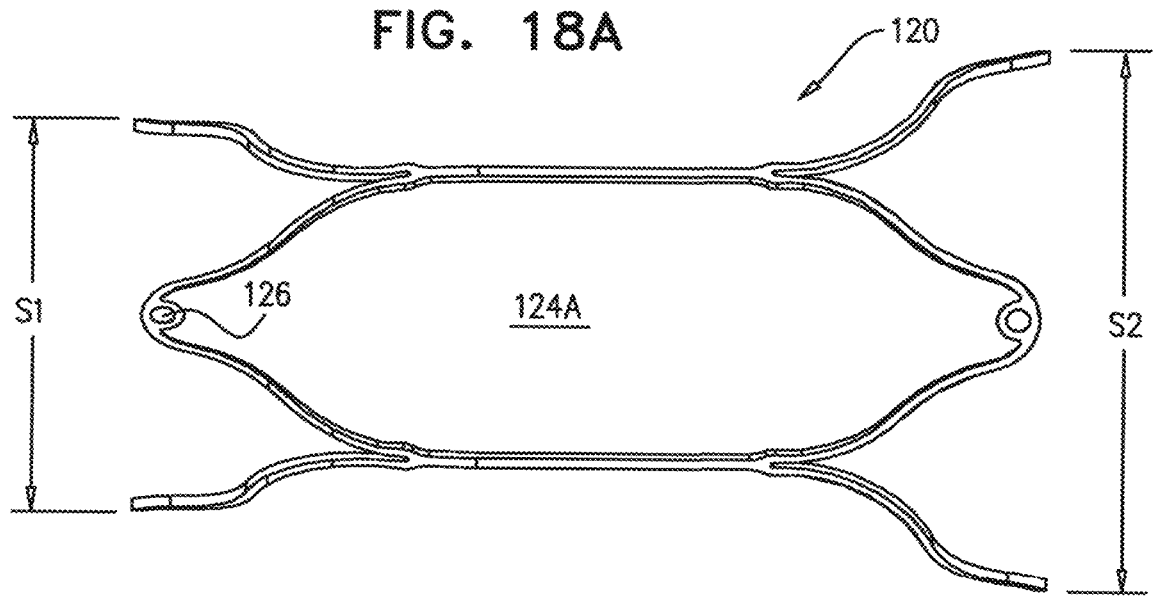
Figure 18B:
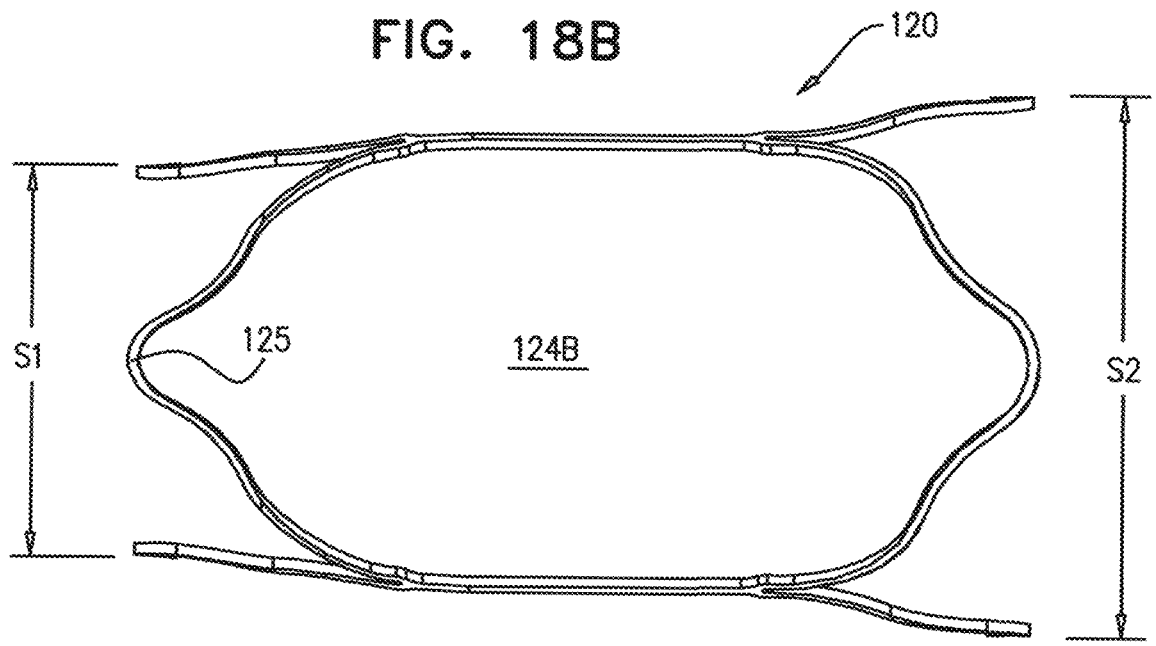

Reference is now made to FIGS. 18A-18B, which are schematic illustrations of respective sides 124A and 124B of device 120 for placing in artery 20, in accordance with some applications of the present disclosure. Device 120 is generally as described hereinabove with reference to FIGS. 15A-15B, except that device 120 as shown in FIGS. 18A-18B is shaped such that at the second end of the device, the device has a greater span S2, than the span of the device S1 at the first end of the device. Typically, the ratio of S2 to S1 is greater than 1:1, e.g., e.g., greater than 1.1:1, and/or less than 2:1, e.g., between 1.1:1 and 2:1 (e.g., between 1.1:1 and 1.4:1).

Reference is now made to FIGS. 18C-18D, which are schematic illustrations of respective sides 124A and 124B of device 120 for placing in artery 20, in accordance with some applications of the present disclosure. Device 120 is generally as described hereinabove with reference to FIGS. 15A-15B and FIGS. 18A-18B, except that device 120 as shown in FIGS. 18C-18D is shaped such that (a) sides 124A and 124B are of equal widths, and (b) at the second end of the device, the device has a greater span S2, than the span of the device S1 at the first end of the device. For some applications, a device is used that defines four parallel artery contact regions 122, all of which are separated from adjacent artery contact regions by an equal distance, as shown in FIGS. 18C-18D.

Typically, the ratio of S2 to S1 of device 120 as shown in FIGS. 18C-18D is as described hereinabove. Thus, the ratio of S2 to S1 is typically greater than 1:1, e.g., e.g., greater than 1.1:1, and/or less than 2:1, e.g., between 1.1:1 and 2:1 (e.g., between 1.1:1 and 1.4:1).

Reference is now made to FIG. 19, which is a schematic illustration of a D-shaped device 150 for placing inside artery 20, in accordance with some applications of the present disclosure. For some applications, a device having a D-shaped cross-section, as shown, is placed inside the artery. A straight portion 152 of the cross-sectional shape flattens a portion of the arterial wall that is adjacent to the straight portion, thereby increasing the strain in the portion of the arterial wall relative to the strain in the portion of the arterial wall in the absence of the device.

It is noted that device 120 and other intra-arterial devices described herein (such as devices 70, 80, and 90) define contact regions that contact the intra-arterial wall, the contact regions comprising a plurality of generally parallel strut portions. Typically, for each of the devices, the minimum distance between a first strut portion of the device and an adjacent strut portion to the first strut portion is 2 mm. It is further noted that the intra-arterial devices described herein (such as devices 60, 70, 80, 90, 120, 130 140, 150, 170, 174, 176, 190, and/or 200) cause the artery to assume a non-circular cross-sectional shape, such as a triangular, a rectangular, or an oval shape.

For some applications, the intra-arterial devices described herein (such as devices 60, 70, 80, 90, 120, 130, 140, 150, 170, 174, 176, and/or 190) are configured, upon implantation of the device inside the artery, to cause one or more contiguous portions of the arterial wall to become flattened, each of the contiguous portions having an area of more than 10% of the total surface area of the artery in the region in which the device is placed. Typically, the aforementioned devices contact less than 20 percent (e.g., less than 10 percent) of the wall of the artery along more than 80% of the length of the region of the artery along which the device is placed. As described hereinabove, for some applications, the intravascular devices described herein (such as devices 60, 70, 80, 90, 120, 130, 140, and 150) have a total cross-sectional area of less than 5 sq mm, e.g., less than 0.8 sq mm, or less than 0.5 sq mm. (The total cross-sectional area should be understood to refer to the cross-sectional area of the solid portions of the devices, and not the space in between the solid portions.) The devices typically have this cross-sectional area over a length of the device of more than 4 mm, e.g., more than 6 mm, and/or less than 12 mm, e.g. less than 10 mm. For example, the devices may have the aforementioned cross sectional area over a length of 4 mm-12 mm, e.g., 6 mm-10 mm, or over a length of 10 mm-30 mm.

For some applications, the dimensions of the intra-arterial devices described herein (such as devices 60, 70, 80, 90, 120, 130, 140, 150, 170, 174, 176, 190, and/or 200) are chosen based upon patient-specific parameters.

For some applications, the intra-arterial devices described herein (such as devices 60, 70, 80, 90, 120, 130, 140, 150, 170, 174, 176, 190, and/or 200) are made of a shape-memory alloy, such as nitinol. The nitinol is configured to assume an open, deployed configuration at body temperature, and to assume a crimped configuration in response to being heated or cooled to a temperature that differs from body temperature by a given amount, such as by 5 C. In order to insert the device, the device is heated or cooled, so that the device assumes its crimped configuration. The device is placed inside the artery, and upon assuming body temperature (or a temperature that is similar to body temperature), the device assumes its deployed, open configuration. Subsequently, the device is retrieved from the artery by locally heating or cooling the region of the artery in which the device is disposed. The device assumes its crimped configuration and is retrieved from the artery using a retrieval device. For some applications, a device is inserted into the artery temporarily in order to cause the artery to undergo a permanent shape change. Subsequent to changing the shape of the artery, the device is retrieved from the artery, for example, in accordance with the techniques described above.

For some applications, the intra-arterial devices described herein (such as devices 60, 70, 80, 90, 120, 130, 140, 150, 170, 174, 176, 190, and/or 200) are configured to expand both radially and longitudinally upon implantation of the device inside the subject's artery.

For some applications, the intra-arterial devices described herein (such as devices 60, 70, 80, 90, 120, 130, 140, 150, 170, 174, 176, 190, and/or 200) are configured such that, upon implantation of the device inside artery 20, the shape of the device remains substantially the same for the duration of a cardiac cycle of the subject. Alternatively, the device is configured to flex in response to the subject's cardiac cycle. For some applications the device flexes passively, in response to blood pressure changes in the artery. Alternatively or additionally, the device is actively flexed. For example, the device may include a piezoelectric element, and an inductive charged coil (inside or outside of the subject's body), drives the piezoelectric element to flex.

For some applications, baroreceptors of the subject are activated by driving an electrical current toward the baroreceptors via an intra-arterial device described herein (such as device 60, 70, 80, 90, 120, 130, 140, 150, 170, 174, 176, 190, and/or 200). Thus, the baroreceptors are stimulated both by mechanical shape changes to the artery as a result of the device being placed inside the artery, and via the electrical stimulation of the baroreceptors. For some applications, baroreceptors at least partially adapt to the shape change of the artery due to the placement of intra-arterial device inside the artery, and the baroreceptors fire with a lower firing rate at a given blood pressure, relative to when the device was first implanted. For some applications, in response to the lowered firing rate of the baroreceptors, due to the adaptation of the baroreceptors to the implanted device, electrical stimulation of the baroreceptors is increased.

Reference is now made to FIG. 20, which is a schematic illustration of intra-arterial device 120, the device including a mesh 160 between artery contact regions 122 of the device, in accordance with some applications of the present disclosure. For some applications, any one of the intra-arterial devices described herein (such as devices 60, 70, 80, 90, 120, 130, 140, 150, 170, 174, 176, 190, and/or 200) is shaped to define struts, or other artery contact regions, that are configured to change a shape of the arterial wall, by exerting a force on the arterial wall. The device additionally includes a mesh in between the regions that are configured to change the shape of the arterial wall. The mesh is configured not to change the mechanical behavior of the artery (e.g., by changing the shape of the arterial wall), but is configured to prevent strokes caused by embolization of arterial plaque, by stabilizing the arterial plaque, in a generally similar manner to a regular stent. In general, for some applications, the intra-arterial devices described herein are used to treat hypertension, and are additionally used to treat arterial disease. For some applications, the intra-arterial devices described herein are placed in a subject's carotid artery subsequent to, or during, a carotid endarterectomy procedure.

Reference is made to FIG. 21, which is a graph showing the derivative of strain versus pressure as a function of rotational position around the artery, in accordance with respective models of an artery, in accordance with some applications of the present disclosure. The graph shows the derivative of strain versus pressure as a function of rotational position around a quadrant of an artery, for the following four models of the artery:

1) A circular elastic artery having no device placed therein, at 150 mmHg.

2) An artery having device 120 placed therein, the device causing the artery to assume a rectangular shape. The artery is modeled at a pressure of 150 mmHg. One of the contact points of the device with the artery wall is between 40 and 80 arbitrary units along the x-axis.

3) A rectangular artery without a device placed therein, at 80 mmHg. One of the corners of the rectangle is at 40 and 80 arbitrary units along the x-axis. This model of the artery was generated in order to separate the effect of changing the shape of the artery to a rectangular shape from the effect of having a device (such as device 120) placed inside the artery.

4) The rectangular artery without a device placed therein, at 150 mmHg.

The shapes of the curves indicate the following:

1) As expected, the derivative of the strain with respect to pressure of the circular, elastic artery is constant due to the elasticity of the artery.

2) At the contact point of the intra-arterial device with the artery, the strain-pressure derivative is reduced relative to the rounded artery. At the non-contact regions of the artery, the strain-pressure derivative is also reduced relative to the rounded artery. However, at the non-contact regions, the pressure-strain derivative is still approximately half that of the rounded artery. This indicates that at the non-contact regions, the pulsatility of the artery is reduced, relative to a rounded artery, but that the artery is still substantially pulsatile. Therefore, for some applications, devices are inserted into an artery which re-shape the arterial wall, such that at any longitudinal point along the artery there are non-contact regions at which regions there is no contact between the device and the arterial wall, such that the artery is able to pulsate.

3) Based on the two rectangular models of the artery (at 80 mmHg and 150 mmHg), it may be observed that at the straightened regions of the artery (i.e., not at the corner of the rectangle), the strain-pressure derivative of the artery increases at low-pressures (e.g., 80 mmHg), relative to a rounded, elastic artery. At higher pressures (e.g., 150 mmHg), the strain-pressure derivative of the straightened regions of the artery is roughly equal to that of the rounded, elastic artery. This indicates that straightening the wall of the artery, by causing the artery to assume a rectangular or an elliptical shape, may increase the pulsatility of the artery. Therefore, for some applications, devices are inserted into the artery that straighten regions of the arterial wall.

Reference is now made to FIGS. 22A-22C, which are schematic illustrations of a delivery device 160 for placing an intra-arterial device in the vicinity of a subject's carotid bifurcation, in accordance with some applications of the present disclosure. For some applications, the intra-arterial devices described herein (such as devices 60, 70, 80, 90, 120, 130, 140, 150, 170, 174, 176, 190, and/or 200) are implanted in the vicinity of a subject's carotid bifurcation, via a delivery device, e.g., delivery device 160. During the implantation of the device, the proximal end of the device is released from the delivery device such that the proximal end of the device is positioned at the start of the bifurcation. Subsequent to the proximal end of the device having been positioned, the distal end of the intravascular device is released from the delivery device. For some applications, prior to releasing the distal end of the device, the effect of the device on baroreceptor firing and/or blood pressure is measured, and the position of the device is adjusted, in response thereto.

For some applications, delivery device 160 is used to facilitate the above-described implantation procedure. (FIGS. 22A-22C show device 120 being implanted inside the artery, by way of illustration and not limitation.) Delivery device 160 includes a retractable sheath 162 at a distal end thereof. During the insertion of the intra-arterial device, the retractable sheath covers the intra-arterial device, as shown in FIG. 22A. The retractable sheath is configured such that, by pulling the sheath proximally, the proximal end of the intra-arterial device is released. Typically, the intra-arterial device is self-expandable. Thus, by releasing the proximal end of the device, the proximal end expands and becomes coupled to the surrounding arterial walls. During the implantation of the device, the proximal end of the device is released from the delivery device, by retracting the retractable sheath, such that the proximal end of the device is positioned at the start of the bifurcation, as shown in FIG. 22B. Subsequent to the proximal end of the device having been positioned, the distal end of the intravascular device is released from the delivery device, by further retracting retractable sheath 162, as shown in FIG. 22C. For some applications, prior to releasing the distal end of the device, the effect of the device on baroreceptor firing is measured, and the position of the device is adjusted, in response thereto.

Although delivery device 160 has been described as being used to facilitate delivery of an intra-arterial device as described herein, the scope of the present disclosure includes using delivery device 160 to facilitate the delivery of any intra-arterial device, in a manner that facilitates the release of the proximal end of the intra-arterial device, before the distal end of the intra-arterial device is released. For example, delivery device 160 could be used with a prosthetic valve and/or a stent, such as a bifurcation stent.

Figure 23A:
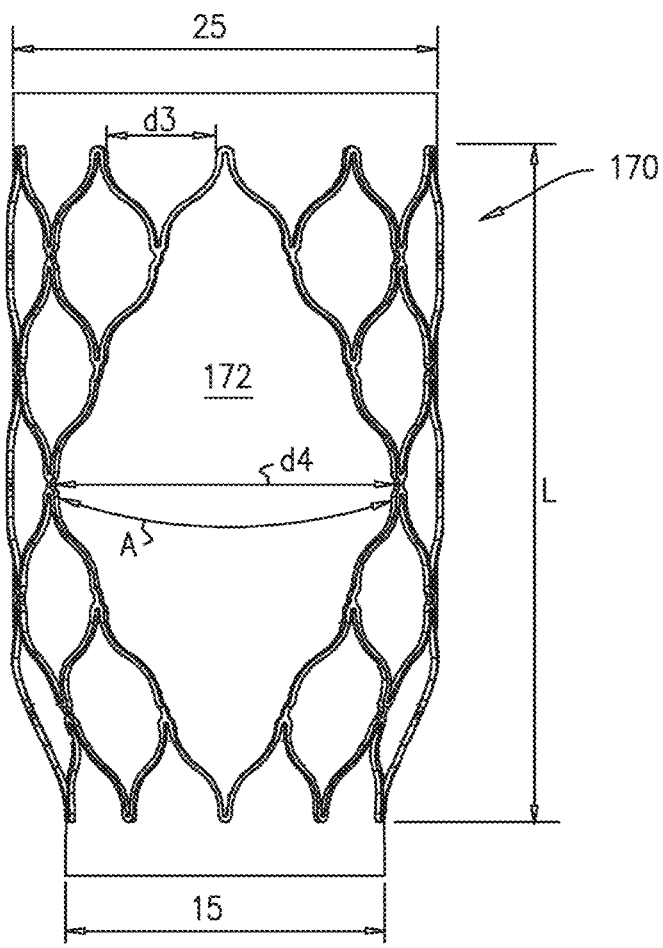
Figure 23B:
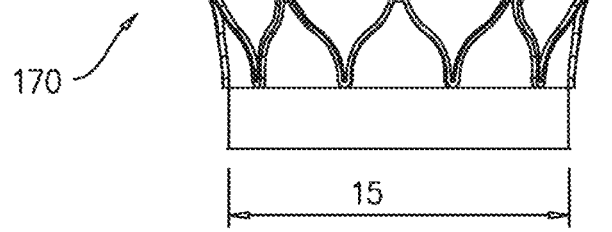

Reference is now made to FIGS. 23A-23B, which are schematic illustrations of respective views of a stent-based intra-arterial device 170, in accordance with some applications of the present disclosure. The views shown in FIGS. 23A and 23B are rotated through 90 degrees about the longitudinal axis of the device, with respect to one another. Device 170 is generally similar to a stent. For example, device 170 is typically cut from nitinol cobalt chrome, and/or stainless steel, such that the device is shaped to define crimpable cells that are defined by struts. However, device 170 typically defines at least one (e.g., two, as shown, or more) non-contact regions 172, at which the device, when placed inside an artery, does not contact the arterial wall.

Typically, each non-contact region 172 defines a contiguous region in which no struts are disposed. Length L of the device is typically greater than 10 mm (e.g., greater than 40 mm), and/or less than 80 mm (e.g., less than 40 mm). At least one of the non-contact regions has a maximum length l, which is typically greater than 5 mm and/or less than 20 mm. Each of the non-contact regions has a maximum width that defines an arc A that defines an angle of more than 30 degrees, e.g., more than 60 degrees. At locations along the length of the device at which a non-contact region is defined, over a continuous portion of the device having a length that is at least 5 mm, a maximum inter-strut distance d4 defined by any set of two adjacent struts is typically at least 1.5 times (e.g., three times) a maximum inter-strut distance d3 defined by any set of two adjacent struts at locations within 3 mm of the longitudinal ends of the device. Thus, by way of illustration and not limitation, if a maximum inter-strut distance defined by any set of two adjacent struts at locations within 3 mm of the longitudinal ends of the device is 3 mm, then, at locations along the length of the device at which a non-contact region is defined, over a continuous portion of the device having a length that is at least 5 mm, a maximum inter-strut distance defined by any set of two adjacent struts is typically at least 4.5 mm.

Although non-contact region 172 is shown having a diamond shape, for some applications, non-contact regions of the devices described herein have different shapes, e.g., a square shape, or a rectangular shape. Typically, non-contact region 172 has a non-circular shape. Although non-contact region 172 is shown as being disposed mid-way along the length of device 170, for some applications, non-contact regions of the devices described herein are disposed such that a center of the non-contact region is closer to a proximal end of the device than to a distal end of the device, or vice versa.

FIGS. 23A-23B show device 170 during the shaping of the device, the device typically being placed on a shaping mandrel 172, during the shaping process. For some applications, device 170 is shaped such that at the second end of the device, the device has a span S2 that is greater than span S1 of the device at the first end of the device. Typically, the ratio of S2 to S1 is greater than 1:1, e.g., greater than 1.1:1, and/or less than 2:1, e.g., between 1.1:1 and 2:1 (e.g., between 1.1:1 and 1.4:1).

Due to the ratio of S2 to S1, upon placement of device 170 inside the artery, the shape of the artery typically becomes increasingly non-circular (e.g., elliptical or rectangular), along the length of the artery, from the first end of the device (having span S1) to the second end of the device (having span S2). Furthermore, due to the ratio of S2 to S1, upon placement of device 170 inside the artery, the cross-sectional area of the artery typically increases along the length of the artery, from the first end of the device (having span S1) to the second end of the device (having span S2). Typically, the device is placed such that the second end of the device (which has the greater span) is disposed in the common carotid artery and/or within the internal carotid artery in the vicinity of the carotid bifurcation, and the first end of the device (which has the smaller span) is disposed within the internal carotid artery, downstream of the bifurcation. In this configuration, the device thus stretches the internal carotid artery in the vicinity of the bifurcation, due to the span of the device at the second end of the device, but does not substantially stretch the internal carotid artery downstream of the bifurcation.

Typically, device 170 is shaped such that the device can be viewed as defining three zones along the length of the device. The second end may be viewed as the maximum-span zone, which is configured to be placed in the vicinity of the carotid bifurcation (or downstream of the carotid bifurcation, as described hereinabove) and to stretch the internal carotid artery in the vicinity of the bifurcation. The first end may be viewed as the minimum-span zone, which is configured to be placed at a location within the internal carotid artery downstream of the bifurcation and to reduce strain on the internal carotid artery at the downstream location relative to if the minimum-span zone had a greater span. The portion of the device between the first and second zones may be viewed as the pulsation zone, at which the device exerts strain on the artery, while facilitating pulsation of the artery by defining non-contact regions at which the device does not contact the artery.

Figure 24A:
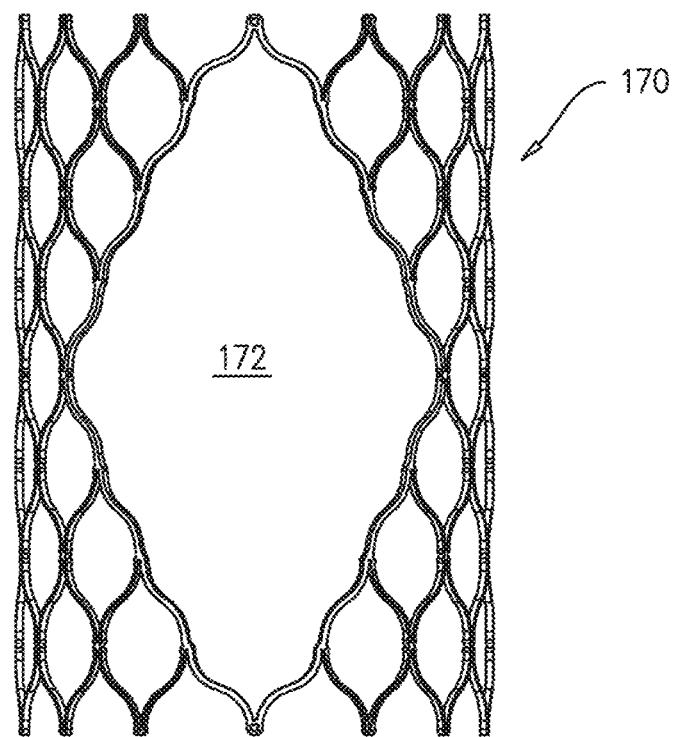
Figure 24B:
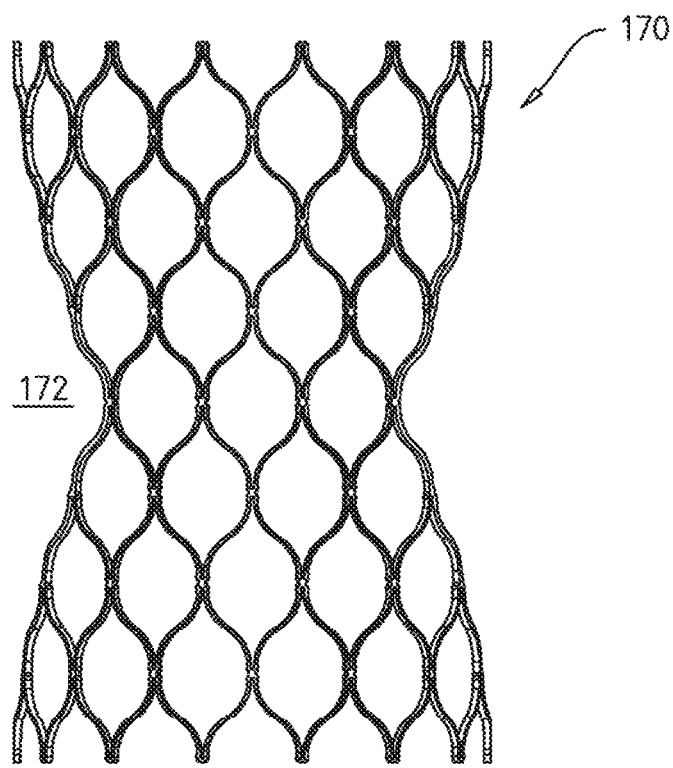

Reference is now made to FIGS. 24A-24B, which are schematic illustrations of respective views of stent-based intra-arterial device 170, in accordance with some applications of the present disclosure. The views shown in FIGS. 24A and 24B are rotated through 90 degrees about the longitudinal axis of the device, with respect to one another. Device 170, as shown in FIGS. 24A-24B is generally similar to device 170 as shown in FIGS. 23A-23B. For example, device 170 typically defines at least two non-contact regions 172, at which the device, when placed inside an artery, does not contact the arterial wall, which are as described hereinabove. However, whereas device 170 as shown in FIGS. 23A-23B is shaped such that span S2, at the second end of the device, is greater than span S1, at the first end of the device, device 170 as show24n in FIGS. 24A-B is shaped such that spans S1 and S2 are approximately equal.

Figure 25A:
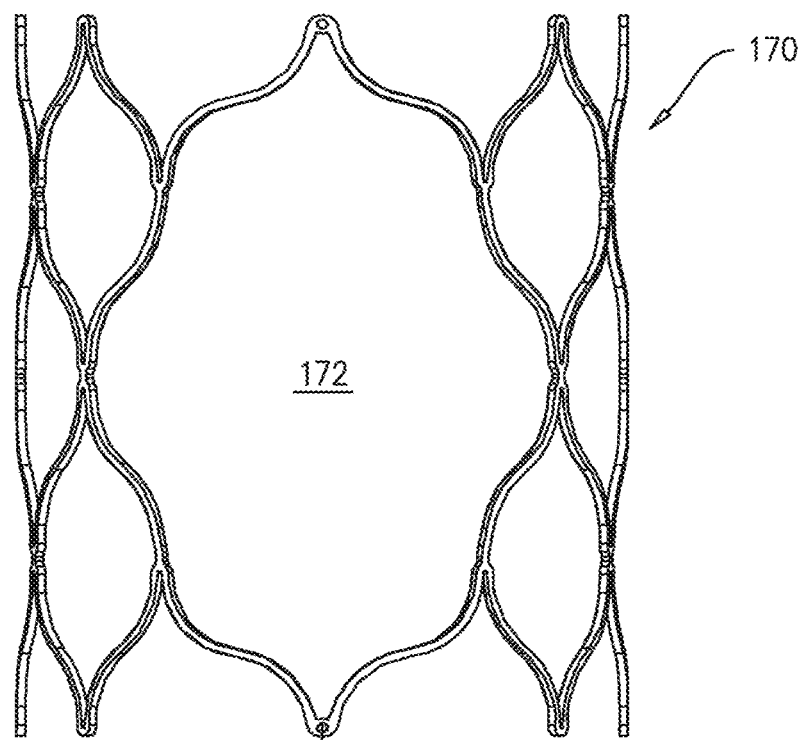
Figure 25B:
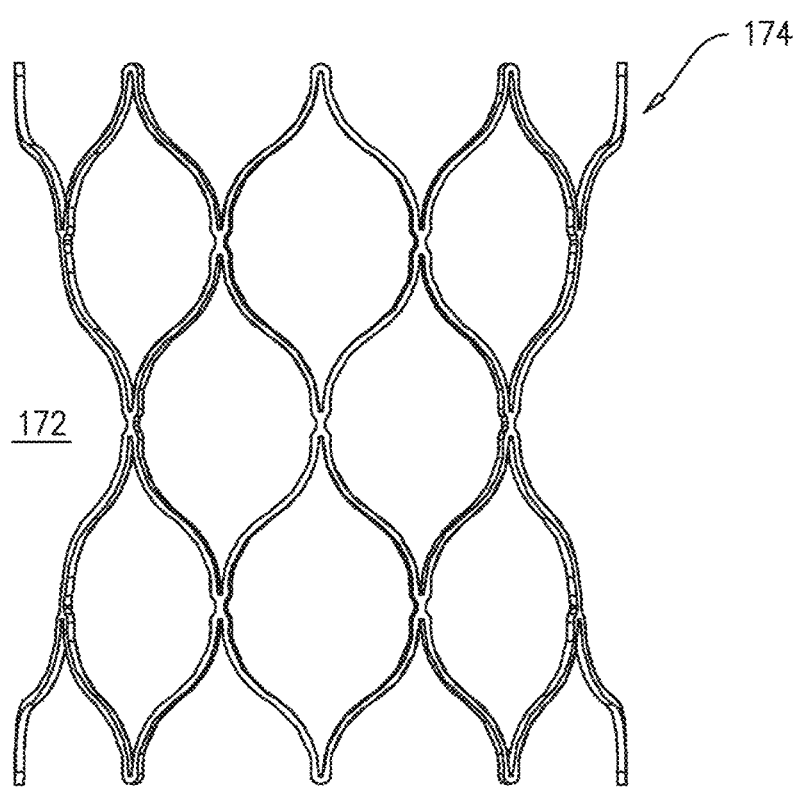

Reference is now made to FIGS. 25A-25B, which are schematic illustrations of respective views of stent-based intra-arterial device 174, in accordance with some applications of the present disclosure. The views shown in FIGS. 25A and 25B are rotated through 90 degrees about the longitudinal axis of the device, with respect to one another. Device 174, shown in FIGS. 25A-25B is generally similar to device 170, shown in FIGS. 23A-23B. For example, device 174 typically defines at least two non-contact regions 172, at which the device, when placed inside an artery, does not contact the arterial wall, which are as described hereinabove. However, the cells of device 174 are typically larger than those of device 170. For some applications, due to larger cells of device 174 relative to those of device 170, device 174 has a smaller area of metal in contact with the intra-arterial wall when device 174 is placed in the artery than does device 170, when device 170 is placed inside the artery.

An experiment was conducted by the inventors of the present application in which a spring constant of a device having generally similar characteristics to device 174 was measured. As described hereinabove with reference to FIGS. 15A-15B, for the purposes of the experiment, the spring constant of the device was measured by measuring the change in force applied by the device to the artery versus the change in the diameter of the device during cycles of crimping and expansion of the device. The spring constant of the device was determined based upon measurements that were performed using M250-3 CT Materials Testing Machine manufactured by The Testometric Company Ltd. (Lancashire, UK). The device had a spring constant of 1.5 N/mm. In accordance with the aforementioned experimental result, in accordance with some applications of the disclosure, a device is inserted into a subject's artery in accordance with the techniques described herein, the device having a spring constant of less than 3 N/mm, e.g., less than 2 N/mm, or less than 1.8 N/mm.

Figure 26A:
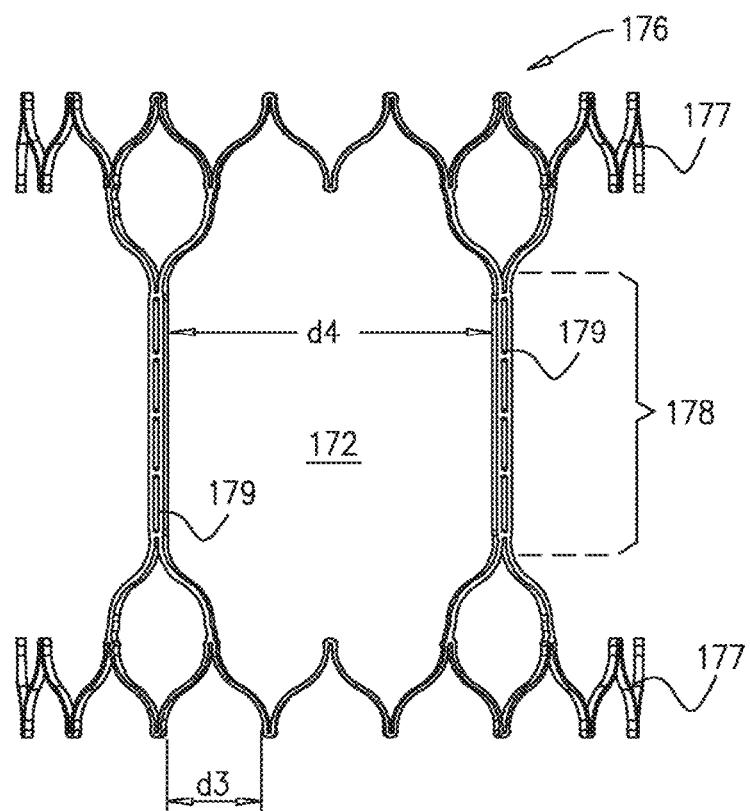
Figure 26B:
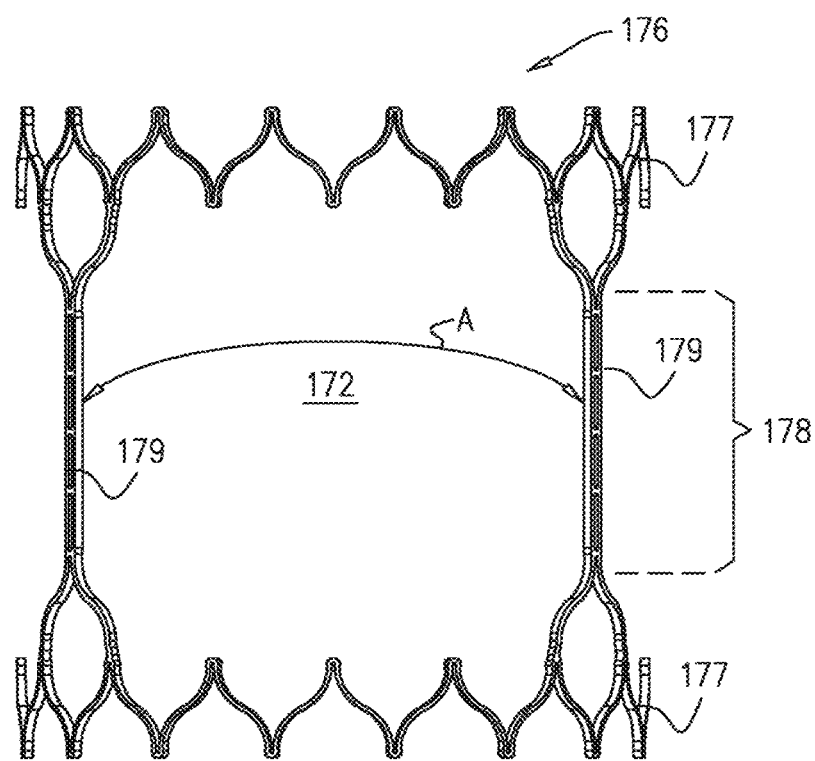

Reference is now made to FIGS. 26A-26B, which are schematic illustrations of respective views of stent-based intra-arterial device 176, in accordance with some applications of the present disclosure. The views shown in FIGS. 26A and 26B are rotated through 90 degrees about the longitudinal axis of the device, with respect to one another. Device 176 typically defines end portions 177, at which struts are typically disposed evenly around the circumference of the device. Device 176 further defines a central portion 178, which defines one or more (e.g., four, as shown) non-contact regions 172. Non-contact regions 172 are typically generally as described hereinabove. The central portion of the device also defines three or more (e.g., four as shown) struts 179, the struts typically being parallel to each other.

As described with reference to device 170, shown in FIGS. 23A-23B, the length of device 176 is typically greater than 10 mm (e.g., greater than 40 mm), and/or less than 80 mm (e.g., less than 40 mm). At least one of the non-contact regions has a maximum length, which is typically greater than 5 mm and/or less than 20 mm. Each of the non-contact regions has a maximum width that defines an arc A (FIG. 26B) that defines an angle of more than 30 degrees, e.g., more than 60 degrees. At locations along the length of the device at which a non-contact region is defined, over a continuous portion of the device having a length that is at least 5 mm, a maximum inter-strut distance d4 (FIG. 26A) defined by any set of two adjacent struts is typically at least 1.5 times (e.g., three times) a maximum inter-strut distance d3 defined by any set of two adjacent struts at locations within 3 mm of the longitudinal ends of the device. Thus, by way of illustration and not limitation, if a maximum inter-strut distance defined by any set of two adjacent struts at locations within 3 mm of the longitudinal ends of the device is 3 mm, then, at locations along the length of the device at which a non-contact region is defined, over a continuous portion of the device having a length that is at least 5 mm, a maximum inter-strut distance defined by any set of two adjacent struts is typically at least 4.5 mm.

Figure 27A:
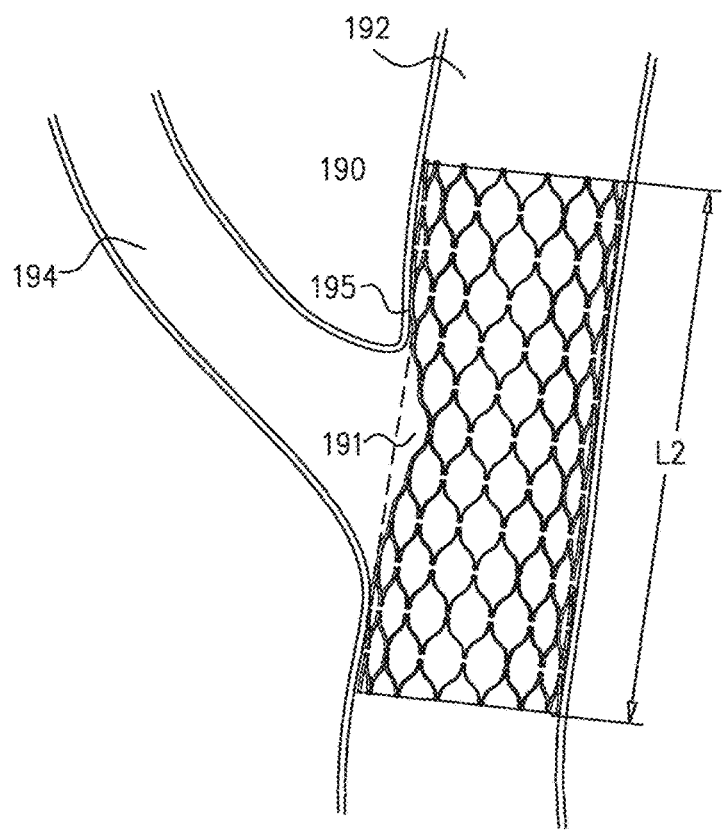
Figure 27B:
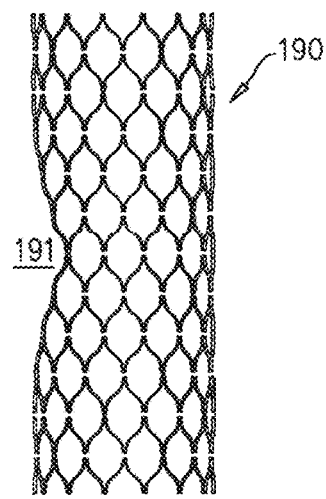
Figure 27C:
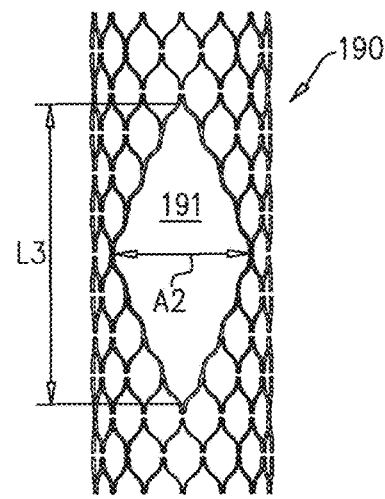

Reference is now made to FIGS. 27A-27C, which are schematic illustrations of a stent-based intra-arterial device 190, in accordance with some applications of the present disclosure. FIG. 27A shows device 190 disposed inside a subject's internal carotid artery 192. Device 190 is generally similar to a stent. For example, device 190 is typically cut from nitinol, cobalt chrome, and/or stainless steel such that the device is shaped to define crimpable cells that are defined by struts. However, device 190 typically defines a non-contact region 191 at which the device does not define any struts. Region 191 is generally similar to non-contact region 172 described hereinabove, except for the differences described hereinbelow.

As described hereinabove, typically, the intra-arterial devices described herein are implanted in a vicinity of the carotid bifurcation, so as to increase the radius of curvature of the internal carotid artery in the vicinity of the bifurcation, thereby causing increased baroreceptor firing. For some applications, the devices described herein, when placed in the vicinity of the bifurcation, are placed such that a proximal end of the device is placed within internal carotid artery 192 immediately distal (i.e., downstream) to the carotid bifurcation, and such that the distal end of the device is placed further downstream from the bifurcation. The device is typically placed such that a non-contact region of the device is placed over a region of the internal carotid artery on a side 195 of the internal carotid artery that defines the carotid bifurcation (i.e., the side of the internal carotid artery that is closer to external carotid artery 194). Thus, the device stretches the region of the internal carotid artery, while facilitating pulsation of the region of the internal carotid artery, in accordance with the techniques described hereinabove.

For some applications, device 190 is placed in the subject's common carotid artery such that a proximal end of the device is placed proximal to (i.e., upstream of) the carotid bifurcation, and such that the distal end of the device is placed within the internal carotid artery downstream of the bifurcation. For such applications, device 190 is typically placed in the common carotid artery such that region 191 is disposed (a) adjacent to the bifurcation of external carotid artery 194 from the common carotid artery, and (b) adjacent to a region of the internal carotid artery on the side of the internal carotid artery that defines the carotid bifurcation (i.e., the side that is closer to the external carotid artery). That is, the device is placed in the carotid artery such that region 191 extends from a location within the common carotid artery that is proximal to the carotid bifurcation until a location within the internal carotid artery that is downstream of the carotid bifurcation. Typically, a maximum length 13 of region 191 is greater than 15 mm and/or less than 45 mm. Further typically, region 191 defines a maximum width thereof that defines an arc A2 that defines an angle of more than 30 degrees, e.g., more than 40 degrees.

Typically, the placement of region 191 adjacent to the bifurcation of the external carotid artery from the common carotid artery facilitates blood flow into the external carotid artery from the common carotid artery, relative to if a portion of a device that defined struts were placed adjacent to the bifurcation (e.g., if a regular stent were placed along the common carotid artery adjacent to the bifurcation of the common carotid artery with the external carotid artery). This is because, since device 190 does not define any struts in region 191, struts of device 190 do not interfere with blood flow through region 191. Furthermore, since device 190 does not define any struts in region 191, there is no build up of matter (e.g., fibrosis) at region 191.

Typically, the placement of region 191 adjacent to the region of the internal carotid artery on the side of the internal carotid artery that defines the carotid bifurcation (i.e., the side of the internal carotid artery that is closer to the external carotid artery), is such that the device stretches the region of the internal carotid artery, while facilitating pulsation of the region of the internal carotid artery, in accordance with the techniques described hereinabove.

For some applications, device 190 is shaped to conform with the shape of the common and internal carotid arteries. Thus, for some applications, a first side of device 190 that is configured to be placed in contact with side 195 of the internal carotid artery is shorter than a second side of the device that is opposite the first side. For some applications, all of the cells of the second side of the device are closed, and at least some of the cells on the first side are open cells, so as to facilitate shortening of the cells of the first side of the device, upon placement of the device inside the artery. Alternatively some of the cells of the second side are also open, but more of the cells of the first side are open than those of the second side. Typically, a maximum length l2 of device 190 is greater than 20 mm, and/or less than 80 mm.

It is noted that the devices shown in FIGS. 23A-27C may be defined as having (a) stent-like proximal and distal end portions, and (b) a central portion in between the end portion that defines one or more non-contact regions in which the device does not define any struts, the non-contact region(s) being contiguous regions, having dimensions as described hereinabove. For example, the end portions may be stent-like in that, within the end portions, a maximum distance between any strut and an adjacent strut thereto is less than 5 mm. For some applications, using devices that have stent-like end portions reduces thickening of the arterial wall adjacent to the end portions relative to if devices were used having end portions that define struts that are adjacent to one another and that are at a distance from one another of more than 3 mm. Typically, the stent-based devices described herein are cut from nitinol, and/or a different metal or alloy (such as cobalt chrome, and/or stainless steel). Alternatively, one or more of the stent-based devices described herein are made of braided mesh.

In general, the devices described herein are typically configured such that the devices define (a) first and second end portions at the proximal and distal end of the device, configured to couple the device to the artery, and (b) a central portion, between the first and second end portions, that defines one or more non-contact regions, configured to increase the radius of a curvature of a portion of the artery adjacent to the non-contact regions while facilitating pulsation of the portion of the artery. The non-contact regions are typically contiguous regions that define no struts having dimensions as described hereinabove. At locations along the length of the device at which a non-contact region is defined, over a continuous portion of the device having a length that is at least 5 mm, a maximum inter-strut distance defined by any set of two adjacent struts is typically at least 1.5 times (e.g., three times) a maximum inter-strut distance d3 defined by any set of two adjacent struts at locations within 3 mm of the longitudinal ends of the device.

Further typically, the cross-section of the device within 3 mm of the longitudinal ends of the device defines a plurality of dots, corresponding to the struts at the end portions. Similarly, the cross-section of the device at any longitudinal location along the length of the device at which a non-contact region is defined, over a continuous portion of the device having a length that is at least 5 mm, typically defines a plurality of dots, corresponding to the struts at the longitudinal location, the number of dots defined by the cross-section at the longitudinal location typically being less than that of the cross-section of the device within 3 mm of the longitudinal ends of the device. Typically, the minimum angle defined by any set of three of adjacent dots of the cross-section within 3 mm of the longitudinal ends of the device is greater than 150 degrees, and the minimum angle defined by any set of three of adjacent dots of the cross-section at any longitudinal location along the length of the device at which a non-contact region is defined, over a continuous portion of the device having a length that is at least 5 mm, is less than 150 degrees. For example, a ratio of the minimum angle defined by the cross-section within 3 mm of the longitudinal ends of the device to the minimum angle defined by the cross-section at any longitudinal location along the length of the device at which a non-contact region is defined, over a continuous portion of the device having a length that is at least 5 mm, may be greater than 1.25 (e.g., 2).

Figure 27D:
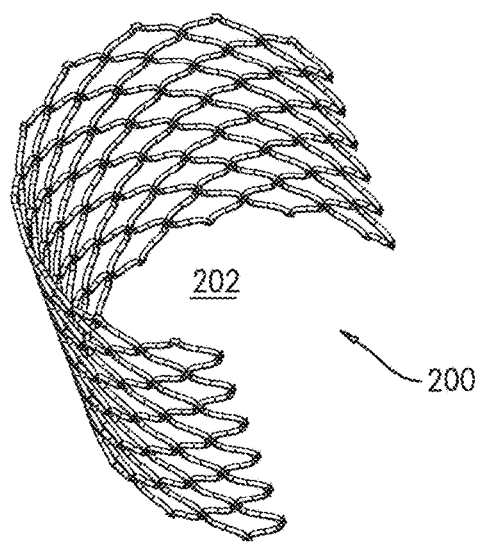

Reference is now made to FIG. 27D, which is a schematic illustration of a stent-based intra-arterial device 200 that defines a C-shaped cross-section, the device defining a non-contact region 202 that runs along the full length of the device, around a given portion of the circumference of the device, in accordance with some applications of the present disclosure. For some applications, the non-contact region may define an arc about the longitudinal axis of the device that is greater than 30 degrees (e.g., greater than 60 degrees). For some applications, device 200 is placed in the subject's carotid artery (FIG. 27A) such that a proximal end of the device is placed proximal to the carotid bifurcation, and such that the distal end of the device is placed within the internal carotid artery downstream of the carotid bifurcation. For such applications, device 200 is typically placed in the carotid artery such that region 202 is disposed (a) adjacent to the bifurcation of the external carotid artery with the common carotid artery, and (b) adjacent to a region of the internal carotid artery on side 195 of the internal carotid artery that defines the carotid bifurcation (i.e., the side that is closer to the external carotid artery).

As described hereinabove with reference to device 190, typically, the placement of region 202 adjacent to the bifurcation facilitates blood flow into the external carotid artery from the common carotid artery, relative to if a portion of a device that defined struts were placed adjacent to the bifurcation (e.g., if a regular stent were placed along the common carotid artery adjacent to the bifurcation of the common carotid artery with the external carotid artery). This is because, since device 200 does not define any struts in region 202, struts of device 200 do not interfere with blood flow through region 202. Furthermore, since device 200 does not define any struts in region 202, there is no build up of matter (e.g., fibrosis) at region 202.

Typically, the placement of region 202 adjacent to the region of the internal carotid artery on the side of the internal carotid artery that defines the carotid bifurcation, is such that the device stretches the region of the internal carotid artery, while facilitating pulsation of the region of the internal carotid artery, in accordance with the techniques described hereinabove.

Reference is now made to FIGS. 28A-C, which are schematic illustrations of cross-sectional views of device 170, in accordance with some applications of the present disclosure. Typically, the devices described herein are configured to increase the radius of curvature of the internal carotid artery on side 195 of internal carotid artery 192, i.e., the side defining the carotid bifurcation. Therefore, devices described herein as defining non-contact regions are typically placed in the carotid artery such that at least one non-contact region (e.g., region 172 of device 170) is placed adjacent to side 195. (For some applications, the devices described herein define one or more additional non-contact regions, which are placed adjacent to other regions of the internal carotid artery.) As described hereinabove, for example with reference to FIGS. 15A-B, for some applications, placement of a device inside the artery results in the artery having a cross-sectional shape that is more rectangular and/or less circular than in the absence of the device. For such applications, the devices are typically placed in the internal carotid artery, such that radius of curvature of side 195 of the internal carotid artery is increased by more than that of the opposite side of the internal carotid artery.

Some of the stent-like devices described herein (e.g., device 190, and device 200) define a single contiguous region that defines no struts and that is configured to be placed adjacent to side 195 of the internal carotid artery. Others of the stent-like devices (such as device 170, and device 174) define two regions 172 that are disposed on opposite sides of the device from one another, each of which is contiguous and defines no struts. For some applications, one or more of devices 170, 174, and/or 190, shown in FIGS. 23A-27C, and/or others of the devices described herein, are configured such that, at least when the device is in a non-constrained state, the device has a cross-sectional shape, such as a rectangular, an elliptical, or a racetrack-shaped cross-sectional shape, that defines a major axis (i.e., a longest axis defined by the cross-sectional shape) and a minor axis (i.e., a shortest axis defined by the cross-sectional shape). The major axis of the cross-section is parallel to the one or two regions of the device that define no struts, and the minor axis of the cross-section is disposed perpendicularly to the one or more regions that define no struts. For example, FIG. 28A shows device 170 in a non-constrained state thereof. Device 170 defines a racetrack-shaped cross-section, the major axis of the cross-section being parallel to non-contact region 172, and the minor axis of the cross-section being perpendicular to region 172. The major axis of the cross-section has a length l4, and the minor axis has a length l5. Typically the ratio of l4 to l5 is greater than 1.1:1.

For some applications, the devices are configured such that, when the device is in a constrained state inside the internal carotid artery, the device assumes a cross-section, such as a square or circular cross-section, in which the major and minor axes become approximately equal, as shown in FIG. 28B. For example, this may be because the device is more compliant in the direction that is parallel to the non-contact regions than in the direction that is perpendicular to the non-contact regions. Therefore, the device becomes more radially compressed in the direction that is parallel to the non-contact regions than in the direction that is perpendicular to the non-contact regions.

Alternatively, the devices are configured such that the device maintains a cross-sectional shape that defines major and minor axes, when the device is in the constrained state inside the internal carotid artery, as shown in FIG. 28C. Thus, the radius of curvature of side 195 of the internal carotid artery is increased by more than the radius of curvature would be increased by a device having a similar cross-section but that is circularly shaped. For some applications, by maintaining the cross-sectional shape that defines major and minor axes inside the artery, the device reduces damage caused to the arterial wall due to discontinuities in the curvature of the wall at edges of the non-contact regions. This is because, the change in the radius of curvature of the artery at the edges of the non-contact region(s) is typically more gradual for a device having a cross-sectional shape that defines major and minor axes (e.g., an elliptical shape or a racetrack-shape), as described, than for that of a device shaped to define a cross-section, such as a square or circular cross-section, in which the major and minor axes are approximately equal.

For some applications, compression of the device in the direction that is parallel to the non-contact regions is reduced by forming thickened struts for the struts that are adjacent to the non-contact regions. The thickened struts are configured to provide resistance to the constraining force of the artery on the device that causes the device to become compressed.

Figure 29:
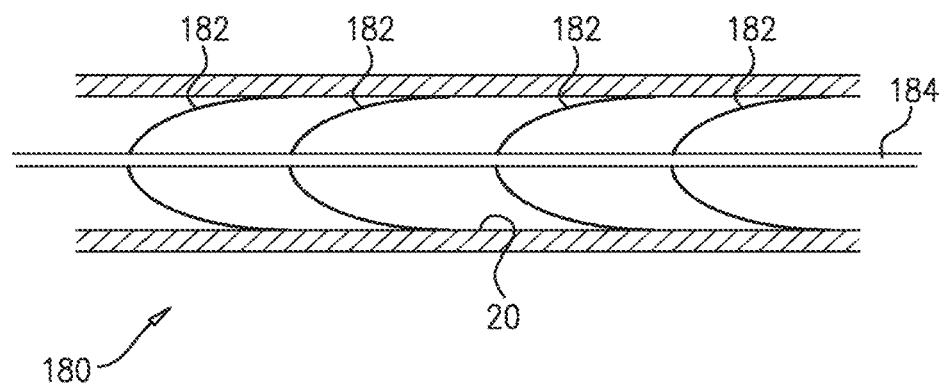
FIG. 29 is a schematic illustration of a further intra-arterial device in accordance with some applications of the present disclosure.

Reference is now made FIG. 29, which is a schematic illustration of a further intra-arterial device 180, in accordance with some applications of the present disclosure. For some applications, intra-arterial device comprises ribs 182 that are disposed on a spine 184, the ribs being configured to expand into contact with the wall of artery 20. Typically, ribs 182 are configured to apply a sufficient mechanical force to the wall of the artery to change a shape of the wall. Further typically, the ribs are placed in a vicinity of a baroreceptor (e.g., within the internal carotid artery in the vicinity of the carotid bifurcation), and are configured to change the shape of the wall in the vicinity of the baroreceptor. Typically, device 180 is configured to accommodate pulsation of regions of the walls between the ribs. For some applications, the springiness of the ribs is adjustable, such as by mechanical, electrical, or thermal means (e.g., at least a portion of the rib may comprises nitinol). The springiness may be mechanically adjusted by sliding a portion of the ribs into a chamber such that such the portion is no longer springy. For some applications, the ribs are configured as electrodes, and an electrical signal is applied to the arterial wall via the ribs. For some applications, device 180 is generally similar to electrode device 20 as described with reference to FIG. 3 of WO 07/013065 to Gross, which is incorporated herein by reference.

Although device 180 is shown in FIG. 29 as having two ribs at each longitudinal location along the device at which the ribs are disposed, for some application, device 180 has more than two, e.g., more than 2, and/or less than 6 ribs at each longitudinal location along the device at which the ribs are disposed.

Figure 30:
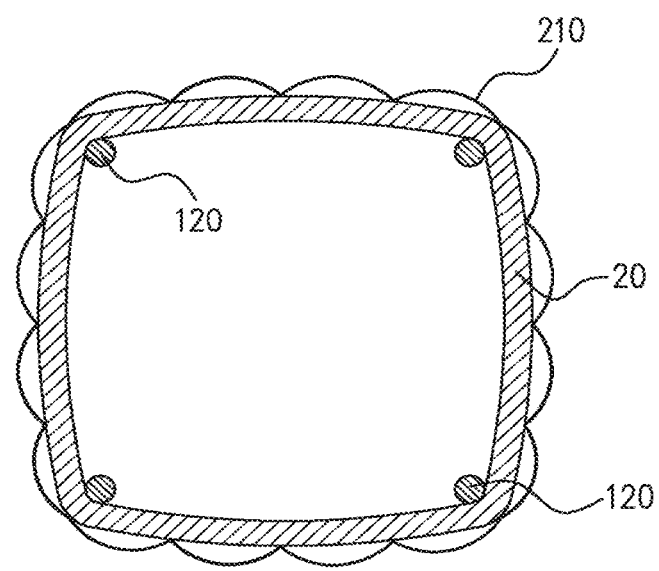
FIG. 30 is a schematic illustration of an extra-arterial device configured to be placed around the outside of an artery, in accordance with some applications of the present disclosure.

Reference is now made to FIG. 30, which is a schematic illustration of an extra-arterial device 210 configured to be placed around the outside of an artery, in accordance with some applications of the present disclosure. For some applications, the intra-arterial devices described herein (such as devices 60, 70, 80, 90, 120, 130, 140, 150, 170, 174, 180, 190, and/or 200) are implanted inside artery 20, and expand at least a portion of the artery, by applying a force to the arterial wall that is directed radially-outwardly. (FIG. 25 shows device 120 implanted inside the artery, by way of illustration and not limitation.) For some applications, extra-arterial device 210 is placed outside the artery and acts to limit the extent to which the intra-arterial device expands the artery. For example, extra-arterial device 210 may comprise sutures as shown, or a ring that is placed on the outside of the artery.

Figure 32:
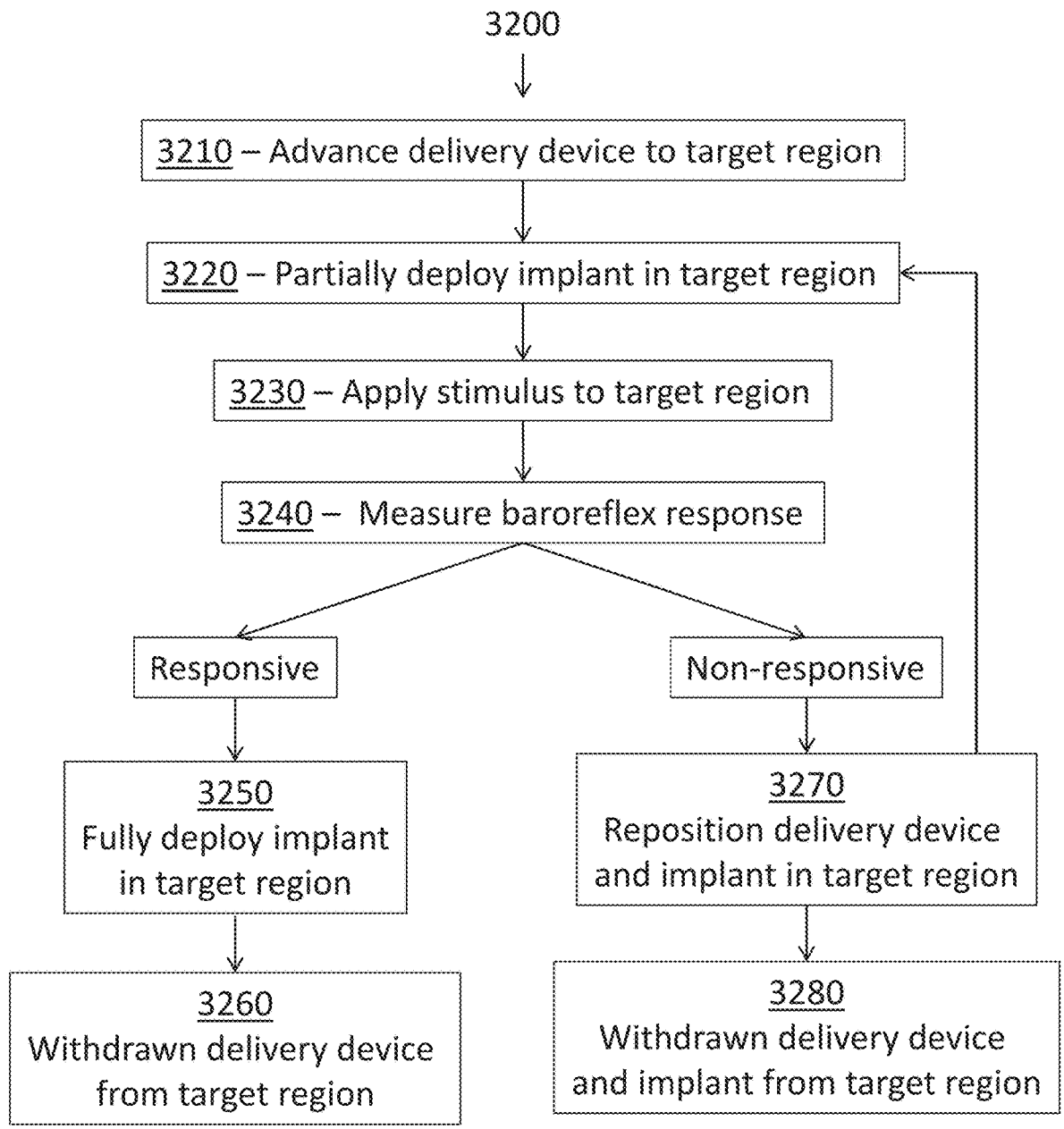
FIG. 32 is a flow chart depicting a method of screening a subject or patient for a therapy, in accordance with some applications of the present disclosure.

Referring now to FIG. 32, an exemplary method 3200 of screening a patient for a therapy, such as a baroreceptor modulation therapy, is described. In a step 3210, a delivery device may be advanced to a target region in a subject. For example, the delivery device may comprise any of the delivery devices described above and herein (such as the delivery device 160), and the target region may comprise a baroreceptor rich region of the vasculature, such as the carotid arteries, the carotid sinus, the aorta, the aortic arch, the subclavian arteries, and/or arteries of the brain. The delivery device 160 may be advanced along the vasculature to be positioned at or adjacent the target region. In a step 3220, an implant or implantable device may be at least partially deployed in the target region. For example, the implant or implantable device may comprise any of the stent-based intra-arterial devices described herein such as device 140 and 170. The intra-arterial device 140 may be enclosed by and deployed from the delivery device 160. In a step 3230, a stimulus may be applied to the target region. The stimulus may be electrical, radiofrequency, thermal, chemical, and/or mechanical, to name a few examples, and may be configured to elicit a baroreceptor signal, which may lead to a significant and measurable decrease in blood pressure and/or heart rate, or a significant and measurable change in baroreceptor activity. In a step 3240, a baroreflex response (e.g., a blood pressure or blood pressure change of the subject or patient) may be measured or sensed. The blood pressure may be measured or sensed in many ways as described herein. If a target blood pressure change is met (i.e., there is a significant drop in blood pressure detected), the subject may be considered a viable candidate for the therapy and the implant may be fully deployed in the target region in a step 3250 before the delivery device may be withdrawn from the target region in a step 3260. If the target blood pressure change is not detected, the delivery device and the implant may be repositioned in the target region in a step 3270 and the steps 3220 and so forth may be repeated. For example, these steps may be repeated to determine an optimal target position for the implantable device. In at least some cases, where the subject is or continues to be non-responsive or partially responsive to the stimulus, the subject may be considered a poor candidate for the therapy and the delivery device and the implant may both be withdrawn from the target region. In some cases, the delivery device and the implant may both be withdrawn from the target region immediately after the non-responsiveness or the partial responsiveness is detected.

Although the above steps show method 3200 of screening a patient for a therapy in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the treatment.

One or more of the steps of the method 3200 may be performed with various circuitry. For example, a controller in operative communication with the lead and/or sensor may be provided. The controller may comprise one or more of a processor or logic circuitry, such as a programmable array logic for field programmable gate array, and the circuitry may be programmed to provide one or more of the steps of the method 3200. The program may comprise program instructions stored on a computer readable memory or programmed steps of the logic circuitry.

Reference is now made to FIGS. 33A-33C, the delivery device 160 may be used to place an intra-arterial device in the vicinity of a subject's carotid bifurcation. For some applications, the intra-arterial devices described herein (such as implant devices 60, 70, 80, 90, 120, 130, 140, 150, 170, 174, 176, 190, and/or 200) are implanted in the vicinity of a subject's carotid bifurcation, via a delivery device, e.g., the delivery device 160. While the delivery of an implant device 140 is shown, the other intra-arterial devices described herein may be delivered similarly as well. The delivery device 160 may first be advanced along the vasculature to the subject's carotid bifurcation (FIG. 33A). During the implantation of the implant device 140, the proximal end of the device 140 may be released from the delivery device 160 such that the proximal end of the device 140 is positioned at the start of the bifurcation (FIG. 33B). The retractable sheath 162 may be withdrawn proximally to free the proximal end of the device 140 from constraint. The withdrawal of the retractable sheath 162 may be reversible and the retractable sheath 162 may be advanced such that the end of the sheath 162 once again covers and constrains the proximal portion of the device 140. Subsequent to the proximal end of the device 140 having been positioned, the distal end of the intravascular device 140 may be released from the delivery device (FIG. 33C). For some applications, prior to releasing the distal end of the device 140, the effect of the device on baroreceptor signaling or firing and/or blood pressure may be measured, and the position of the device is adjusted, in response thereto.

Instead of a proximal to distal release of the implant device 140 or other implant device by the delivery device 160, a delivery device 160a may be configured to release the implant device distally to proximally. Reference is now made to FIGS. 33D-33F, the delivery device 160a may be used to place the intra-arterial device 140 (or other intra-arterial device as described herein) in the vicinity of a subject's carotid bifurcation. The delivery device 160a may first be advanced along the vasculature to the subject's carotid bifurcation (FIG. 33D). During the implantation of the implant device 140, the distal end of the device 140 may be released from the delivery device 160 such that the distal end of the device 140 is positioned at the start of the bifurcation (FIG. 33E). The distal portion of the delivery device 160a may be retracted relative to the implant device 140 to free the distal portion of the implant device 140 from constraint, allowing the distal portion of the delivery device 160a to expand. Such retraction may be reversible and the distal portion of the delivery device 160a may be advanced to once again cover and constrain the distal portion of the device 140. Subsequent to the distal end of the device 140 having been positioned, the proximal end of the intravascular device 140 may be released from the delivery device (FIG. 33F). For some applications, prior to releasing the proximal end of the device 140, the effect of the device on baroreceptor signaling or firing and/or blood pressure may be measured, and the position of the device is adjusted, in response thereto.

The delivery device 160 or 160a may comprise one or more leads 330 that may be coupled to one or more of the delivery device 160 or 160a or the intra-arterial device 140. The one or more leads 330 may be used to electrically map the vicinity of the subject's carotid bifurcation or otherwise detect and measure the effect of the partially deployed intra-arterial device 140, which may provide a mechanical stimulus to the baroreceptors in the region. Alternatively or in combination, the one or more leads 330 may be used to convey a stimulation signal to the vicinity of the subject's carotid bifurcation, such as an electrical or thermal stimulation signal, to elicit a baroreflex response. The stimulation signal may be conveyed through one or more of the delivery device 160 or the intra-arterial device 140. Alternatively or in combination, an external sensor may be used to detect and measure any baroreflex response.

The lead 330 may comprise a distal end in contact with the distal portion of the intra-arterial device 140 such that when the intra-arterial device 140 is partially deployed, the lead 330 remains in contact and connection with the intra-arterial device 140 (FIG. 33B), and when the intra-arterial device 140 is fully deployed, the lead 330 is no longer in contact and connection with the intra-arterial device 140 (FIG. 33C). Alternatively or in combination, the lead 330 may comprise a distal end in contact with the proximal portion of the intra-arterial device 140 such that when the intra-arterial device 140 is partially deployed, the lead 330 remains in contact and connection with the intra-arterial device 140 (FIG. 33E), and when the intra-arterial device 140 is fully deployed, the lead 330 is no long in contact and connection with the intra-arterial device 140 (FIG. 33F). The connection from the lead 330 to the proximal and/or distal portion of the intra-arterial device may comprise a metal-to-metal connection.

Figure 34:
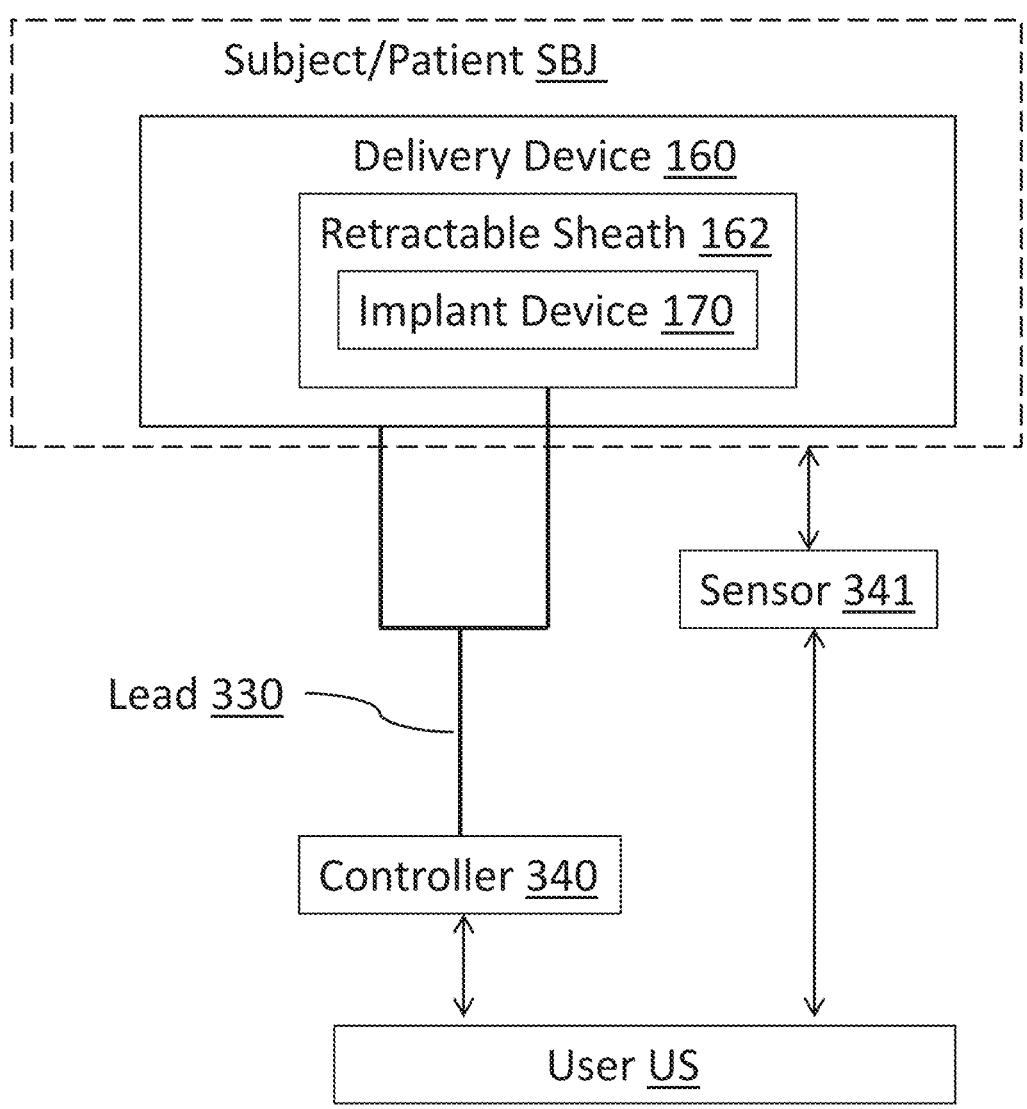
FIG. 34 is a schematic of a delivery device system for screening a subject or patient for placement of an intra-arterial device, in accordance with some applications of the present disclosure.

FIG. 34 shows an exemplary system 3400 for screening a patient for a therapy. The system 3400 may be used to implement the method 3200 above, for example. The system 3400 may comprise the delivery device 160 or 160a and the implant device 140. As described above (FIGS. 33D-33F), the delivery device 160a may be retracted to deliver the implant device 170 distally to proximally. Or, as described above, (FIGS. 33A-33C), the delivery device 160 may comprise a retractable sheath 162 which may enclose the implant device 140 and which may be retracted to deploy the implant device 140 proximally to distally. As shown in FIG. 34, the delivery device 160 may be advanced into a target region in the subject/patient SBJ. The system 3400 may further comprise a controller 340 that may couple to the lead 330. The lead 330 may be coupled to one or more of the implant device 140 or the delivery device 160. The controller 340 may generate a stimulation signal, such as an electrical or thermal stimulation signal, to be conveyed through the lead 330 and optionally the implant device 140 and/or the delivery device 160, 160a to the target region of the vasculature. Alternatively or in combination, the controller 340 may generate a current which may be conveyed through at least the lead 330 to electrically map the target region of the vasculature. Alternatively or in combination, the stimulation signal may simply be mechanical, such as contact on or pressure exerted onto the inner wall of the carotid artery by the partially deployed implant 140. In some embodiments, the system 3400 may further comprise an external sensor 341 for measuring or determining baroreceptor activity extra-vascularly. The external sensor 341 may comprise one or more of a heart rate monitor, a blood pressure monitor (such as an external blood pressure sensor, an intra-arterial blood pressure sensor (i.e., an arterial line), or a blood pressure sensor connected an arterial line of the delivery device 160 or other catheter), a plurality of electrodes for ECG or EEG, a blood flow rate monitor (e.g., using ultrasound), a blood flow velocity monitor (e.g., using ultrasound), an oxygenation sensor (e.g., a pulse oximeter or other optical detector), a vasoactivity sensor, a nerve activity sensor, a piezo electric pressure transducer, a membrane pH electrode, or a strain gage, to provide a few examples. The user US may operate and monitor the controller 340 and optionally the sensor 341.

Figure 35:
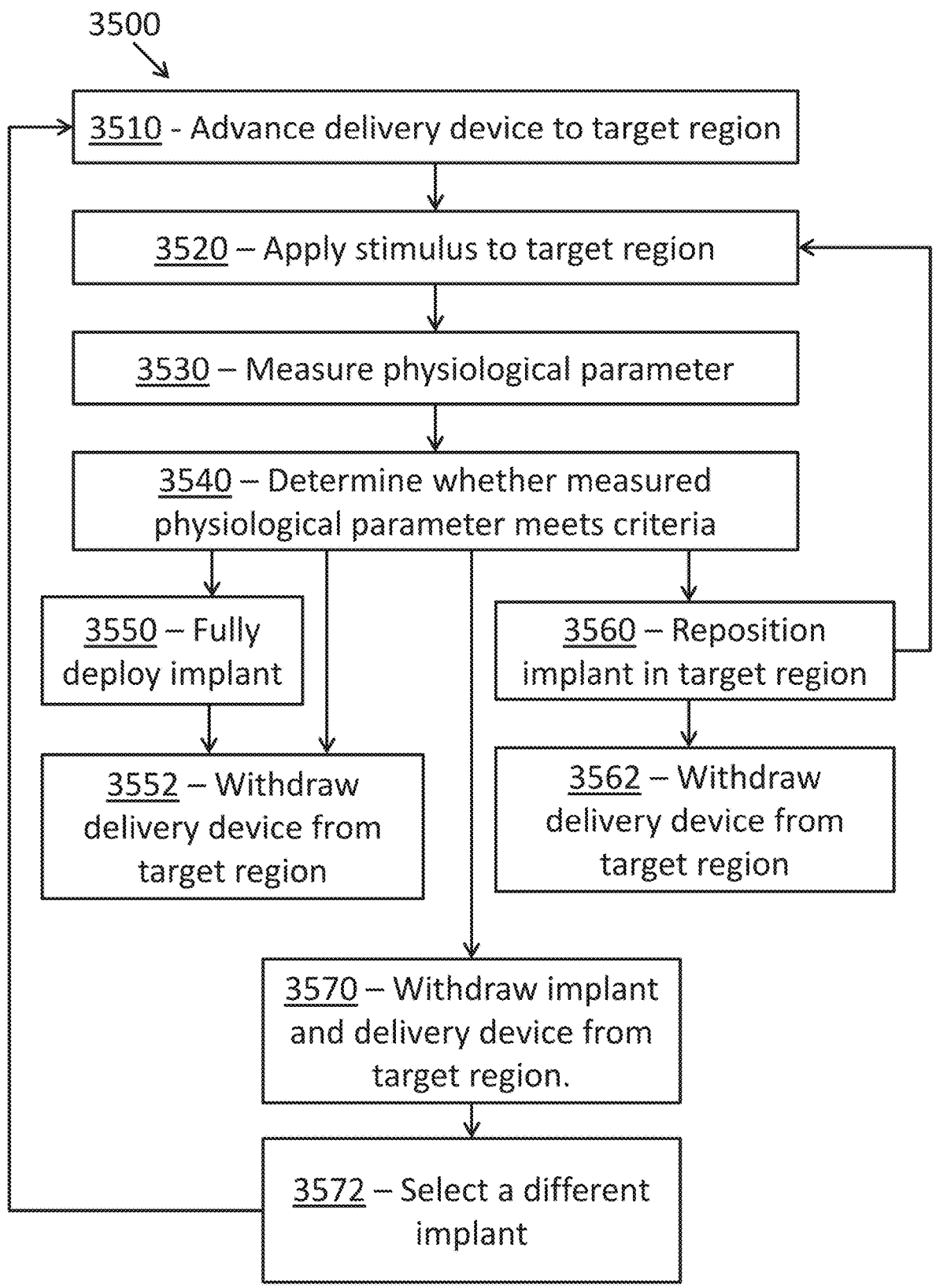
FIG. 35 is a flow chart depicting steps in the use of a system for screening a subject or patient for therapy in accordance with some applications of the present disclosure
Figure 36A:
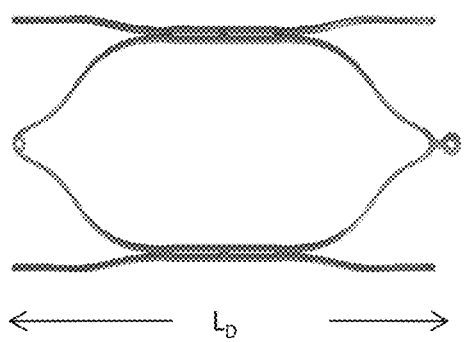
FIGS. 36A-36E show aspects of an intra-arterial device relevant to the screening of a subject or patient for placement of an intra-arterial device, in accordance with some applications of the present disclosure.
Figure 36B:
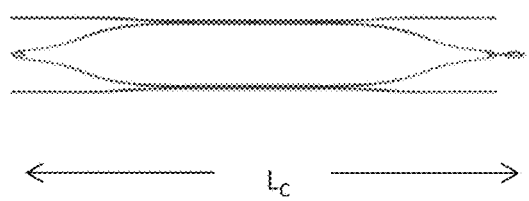
Figure 36C:
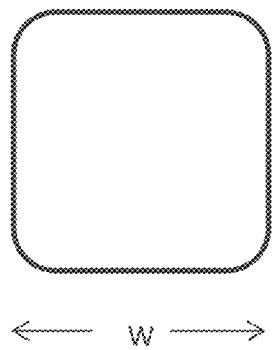
Figure 36D:
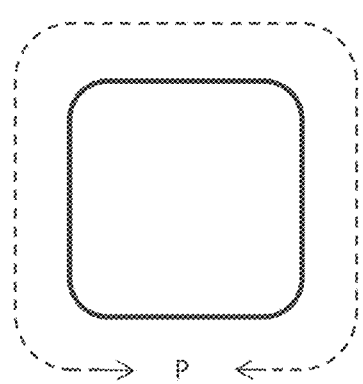
Figure 36E:
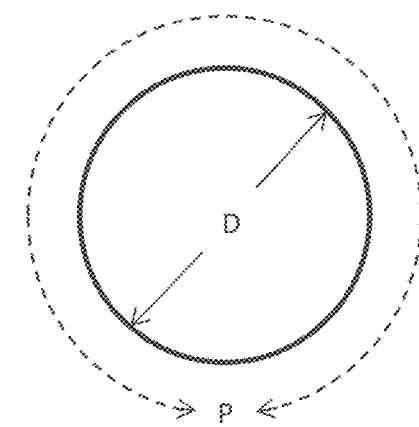

FIG. 35 shows an exemplary method 3500 of screening a patient for a therapy, such as baroreceptor modulation therapy. In a step 3510, a delivery device may be advanced to a target region in a subject. For example, the delivery device may comprise any of the delivery devices or mechanical stimulus apparatuses described above and herein (such as the delivery device 160 or 370). The target region may comprise a baroreceptor rich region of the vasculature, such as the carotid arteries, the carotid sinus, the aorta, the aortic arch, the subclavian arteries, and/or arteries of the brain. The delivery device may be advanced along the vasculature to be positioned at or adjacent the target region.

In a step 3520, a stimulus may be applied to the target region. The stimulus may be electrical, radiofrequency, thermal, chemical, and/or mechanical, to name a few examples, and may be configured to elicit a baroreceptor signal, which may lead to a significant and measurable change in one or more physiological parameter (e.g., a decrease in blood pressure and/or heart rate or a significant and measurable change in baroreceptor activity). In some cases, the stimulus can be applied to the target region by partially or fully deploying the implant at or near the target region. The implant or implantable device may comprise any of the stent-like intra-arterial devices described herein, such as device 120, 160, or 170. In some cases, the implant may be enclosed by and/or deployed from the delivery device.

In a step 3530, a physiological parameter (e.g., a baroreflex response such as a blood pressure value or change in blood pressure of the subject or patient) may be measured or sensed (e.g., detected). In many cases, a physiological parameter measured or sensed in accordance with the methods and systems described herein can be modulated (e.g., can increase or decrease in magnitude or frequency) in response to a stimulus, such as a mechanical and/or an electrical stimulus.

A physiological parameter can comprise a measure of hypertension, an autonomic parameter, a heart failure parameter, a structural configuration of a biological tissue, or a qualitative biological measure. A measure of hypertension can comprise measurement or sensing of heart rate or blood pressure (e.g., systolic blood pressure, diastolic blood pressure, a ratio or difference between systolic and diastolic blood pressure, or mean arterial pressure). An autonomic parameter can comprise a quantification of sympathetic activity (e.g., through measurement or sensing of baroreceptor activity or firing pattern, which can be accomplished, for example, using muscle sympathetic nerve activity (MSNA), skin sympathetic nerve activity (SSNA), or galvanic skin response (GSR)), a baroreflex sensitivity evaluation (e.g., using a non-invasive blood pressure monitor), an evaluation of cardiac bioimpedance (e.g., a non-invasive cardiac system surveyor, such as an ambulatory cardiac impedance monitor), a determination of heart rate variability or other frequency- and time-based metrics such as evaluations of changes or variations in NN intervals (e.g., RMSDD, CDNN, pNN50, etc.), RR intervals (e.g., SDRR, pRR50, etc.), or portions thereof (e.g., evaluations of variations or changes in high frequency (frequencies greater than or equal to 0.15 Hz) periodicity, low frequency (frequencies within a range of approximately 0.04-0.15 Hz) periodicity, very low frequency (frequencies less than or equal to about 0.04 Hz) periodicity, or a ratio thereof), an evaluation of total peripheral resistance (TPR), or a determination of total body water (TBW). Measurement or sensing of a heart failure parameter can comprise determination of heart rate turbulence, stroke volume, cardiac output, or cardiac power (e.g., cardiac power index (CPI)). A measurement or sensing of a structural configuration can comprise the use of fluoroscope, angioscope, or ultrasound (e.g., intravenous ultrasound, Doppler ultrasound, etc.) and can comprise determination of absolute or relative vascular tone or blood velocity. A qualitative biological measure can comprise an evaluation of patient sensation (e.g., pain, tingling, numbness, etc.), an evaluation of patient condition (e.g., skin color or pallor, lethargy, etc.). In some cases, a physiological parameter can comprise a measurement or sensing of a concentration of one or more plasma or urine factor (e.g., catecholamine, endothelins, etc.) or a global or organ-specific noradrenaline spillover rate.

A physiological parameter may be measured or sensed in various ways. Measurement or sensing of a physiological parameter may comprise measuring or sensing a level, value, threshold, or change of a physiological parameter. As described herein, a physiological parameter can be measured or sensed directly or indirectly. A physiological parameter can also be measured manually (e.g., manual evaluation of heart rate) or with the aid of a sensor or specialized equipment (e.g., electrocardiographic evaluation of heart rate and/or electrical waveform). A sensor (such as sensor 341) can be configured to measure or sense one or more level, value, or change related to one or more physiological parameter. A sensor for measuring or sensing a physiological parameter can be configured or used intravascularly, extravascularly, or extracorporeally (e.g., outside of the body). For example, a sensor can be placed against or near the skin to measure one or more physiological parameter. As described herein, a sensor can comprise a means for measuring or sensing a physiological parameter, including a baroreflex sensor, a blood pressure monitor, a heart rate monitor, a blood vessel impedance monitor, or nerve sensor such as a sympathetic nerve sensor.

In a step 3540, a determination regarding the long-term deployment, the repositioning or the removal of the implant can be made based on the one or more measured or sensed physiological parameter. In some cases, a determination regarding whether and/or how an implant should be removed, repositioned, or substituted with another implant can be based on the measurement or sensing of an optimal level, value, or change of the one or more measured or sensed physiological parameter. In some cases, a determination regarding whether and/or how an implant should be removed, repositioned, or substituted with a different implant can be based on a failure to measure or to sense an optimal level, value, or change of the one or more measured and sensed physiological parameter.

An optimal level, value, or change of a measured or sensed physiological parameter (e.g., an optimal response) can be defined or determined before the measuring or sensing of the physiological parameter is performed in the subject or patient. That is, in some cases, an optimal level, value, or change can be a pre-determined criterion. For example, an optimal level, value, or change of a measured or sensed physiological parameter can be based entirely or in part on considerations known before the measuring or sensing, such as accepted literature levels, values, or changes, patient history, or the location of the implant or target region.

In some cases, an optimal level, value, or change of a measured or sensed physiological parameter (e.g., an optimal response) can be determined during one or more step of a method, as described herein (e.g., during one or more the step of method 3500). Thus, an optimal level, value, or change of a physiological parameter may be undetermined prior to one or more step of a method described herein (e.g., an optimal level, value or change may be a non-pre-determined criterion). For example, physiological parameters measured during deployment of an implant (e.g., full deployment, partial deployment, or a combination of full and partial deployments) at a plurality of locations or target regions during the steps of a method 3500 can be compared to determine an optimal level, value, or change for one or more of the measured physiological parameters. Similarly, physiological parameters measured during individual placement (e.g., partial depolyment or full deployment) of a plurality of different implants at one or more locations or target regions can be compared to determine an optimal level, value, or change for one or more of the measured physiological parameters.

In some cases, the subject or patient may be said to be responsive to a stimulus or therapy if one or more measured or sensed physiological parameter meets or exceeds one or more pre-determined criteria (e.g., if a value or a change in the value of a physiological parameter meets or exceeds a pre-determined value, threshold, or degree of change in response to the stimulus).

In some cases, the subject or patient may be said to be non-responsive to a stimulus or therapy either in general or at the target region at which the stimulus was applied if one or more pre-determined criteria is not met by the one or more measured or sensed physiological parameter. Possible courses of action after a non-responsive event include repositioning of an implant to a second target region or withdrawal of the implant from the target region.

In some cases, the measurement or sensing of one or more physiological parameter can indicate that a patient is a viable candidate for a therapy comprising the applied stimulus or a stimulus similar to the applied stimulus. For example, if a target blood pressure change is met (i.e., an optimal decrease in blood pressure compared to a blood pressure of the subject or patient prior to application of the stimulus) after a stimulus is applied during method 3500, the subject or patient may be considered a viable candidate for the therapy. If not done so already, the implant can be fully deployed once it is determined that the subject or patient is responsive to the stimulus in a step 3550. The delivery device can be withdrawn from the target region in a step 3552 after the implant is fully deployed at the target region.

In some cases, a failure to observe (e.g., a failure to measure or to sense) an expected or an optimal level, value, or change of one or more physiological parameter after application of a stimulus can indicate that a subject or patient is not a viable candidate for a therapy comprising the applied stimulus or a stimulus similar to the applied stimulus. In some cases, if a certain level, value, or change in a physiological parameter is not measured or sensed (e.g., if an optimal blood pressure change is not detected), the delivery device and the implant may be repositioned relative to the vessel in a step 3560 and the steps 3520 and so forth may be repeated. Repositioning of an implant may comprise collapsing, crimping, or flexing the implant or it may involve pushing or pulling the implant. Repositioning of an implant can also comprise withdrawing or retracting the implant into the delivery device before it is repositioned and deployed at a new location (e.g., at a second target region). In some cases, the delivery device may be withdrawn, as in a step 3562, after the implant is repositioned.

In some cases, both the implant and the delivery device can be withdrawn from the target region if a preferred level, value, or change of a physiological parameter is not measured or sensed (e.g., if an optimal blood pressure change is not measured or sensed), as in a step 3570. After withdrawal of the implant from the target region, a different implant may be selected, as in a step 3572, and the steps 3510 and so forth may be repeated.

An implant can be selected from a plurality of implants for use in any of the systems and methods described herein. An implant can be selected from a plurality of implants based on its expected or measured effect on one or more physiological parameter. Accordingly, an implant can be selected from a plurality of implants to provide a therapy to a subject or patient based on the measurement or sensing of one or more physiological parameter. That is, an implant can be selected for use in any of the methods or systems described herein to elicit an expected or optimal therapeutic response in a subject or patient (e.g., an optimal baroreflex response, such as an optimal change in blood pressure or baroreceptor firing pattern). In some cases, a determination whether a first or second implant of a plurality of implants should be selected to provide a therapy can be based on a comparison of a change in at least one physiological parameter caused the first and second implants. For example, a determination whether a first or second implant of a plurality of implants should be selected to provide a therapy can be based on which implant is capable of eliciting a more optimal change to at least one physiological parameter (e.g., a more optimal therapeutic response).

As described herein, the size and/or geometry of an implant can modulate one or more physiological parameter when fully or partially deployed at a target region of a subject or patient. As a result, an implant of a plurality of implants can be configured to modulate one or more physiological parameter based on its size or geometry when it is fully or partially deployed at a target region. Moreover, a first implant of a plurality of implants can be better suited to modulate one or more physiological parameter in a subject or patient than a second implant of the plurality of implants. In some cases, one or more implant of a plurality of implants can be configured to alter the geometry or cross-sectional area of a target region. Thus, it can be beneficial to select an implant (e.g., from a plurality of implants) to provide therapy to a subject or patient based on one or more characteristic of the implant, such as the size or geometry of the implant. In some cases, an implant can be selected for long-term deployment at a target region for the purpose of providing therapy to a subject or patient.

A plurality of implants can comprise two or more implants that differ in any aspect, including one or more of size or geometry. For example, a first and second implant of a plurality of implants can differ from one another with respect to device length, the number of vessel-contacting regions, the number of non-contact regions, a number of longitudinal struts, the number of vertices at a given longitudinal position, the relative orientation or configuration of vertices at a given longitudinal position, the relative orientation or arrangement of a first strut to a second strut, the relative arrangement of a crimping region to a strut, or their cross-sectional areas (e.g., the cross-sectional area of an implant when it is fully deployed, partially deployed, or undeployed).

Referring now to FIGS. 36A-36E, an implant can become shorter in length (e.g., longitudinal length, $L_D$ and $L_C$), larger in unconstrained width (W), larger in unconstrained linear perimeter (P), larger in unconstrained diameter (D), or larger in cross-sectional area when deployed or expanded, as compared to the implant's dimensions when crimped or collapsed. An implant can be less than 17.0 mm, 18.0 mm, less than 19.0 mm, less than 20.0 mm, less than 21.0 mm, less than 22.0 mm, less than 23.0 mm, less than 24.0 mm, less than 25.0 mm, from 17.0 to 18.5 mm, from 18.5 mm to 20.0 mm, from 19.5 mm to 21.0 mm, or from 21.0 mm to 25.0 mm in longitudinal length when deployed ($L_D$). In some cases, an implant can be less than 17.0 mm, 18.0 mm, less than 19.0 mm, less than 20.0 mm, less than 21.0 mm, less than 22.0 mm, less than 23.0 mm, less than 24.0 mm, less than 25.0 mm, from 17.0 to 18.5 mm, from 18.5 mm to 20.0 mm, from 19.5 mm to 21.0 mm, or from 21.0 mm to 25.0 mm in longitudinal length when crimped or collapsed ($L_C$).

An implant can be less than 6.5 mm, less than 7.5 mm, less than 8.5 mm, less than 9.5 mm, less than 10.5 mm, less than 11.5 mm, from 6.0 mm to 7.0 mm, from 7.0 mm to 8.0 mm, from 8.0 mm to 9.0 mm, from 9.0 mm to 10.0 mm, or from 10.0 mm to 11.5 mm in width (W) when deployed or otherwise unconstrained. An implant can also be less than 20 mm, less than 25 mm, less than 30 mm, less than 35 mm, less than 40 mm, less than 45 mm, from 15 mm to 20 mm, from 20 mm to 25 mm, from 25 mm to 30 mm, from 30 mm to 35 mm, from 35 mm to 40 mm, or from 40 mm to 45 mm in linear perimeter (P) when deployed or otherwise unconstrained. An implant can also be less than 7.5 mm, less than 8.5 mm, less than 9.5 mm, less than 10.5 mm, less than 11.5 mm, less than 12.5 mm, less than 13.5 mm, from 7.5 mm to 8.5 mm, from 8.5 mm to 9.5 mm, from 9.5 mm to 10.5 mm, from 10.5 mm to 11.5 mm, from 11.5 mm to 12.5 mm, or from 12.5 mm to 13.5 mm in diameter (D) when deployed or otherwise unconstrained.

An implant can be less than 50.0 $mm^2$, less than 60.0 $mm^2$, less than 70.0 $mm^2$, less than 80.0 $mm^2$, less than 90.0 $mm^2$, less than 100.0 $mm^2$, less than 110.0 $mm^2$, less than 120.0 $mm^2$, less than 130.0 $mm^2$, from 50.0 $mm^2$ to 60.0 $mm^2$, from 60.0 $mm^2$ to 70.0 $mm^2$, from 70.0 $mm^2$ to 80.0 $mm^2$, from 80.0 $mm^2$ to 90.0 $mm^2$, from 90.0 $mm^2$ to 100.0 $mm^2$, from 100.0 $mm^2$ to 110.0 $mm^2$, from 110.0 $mm^2$ to 120.0 $mm^2$, or from 120.0 $mm^2$ to 130.0 $mm^2$ in cross-sectional area when deployed or otherwise unconstrained.

In some cases, selection of an implant can be based on the geometry or size of the target region in relationship to the geometry or size of the implant. For example, an implant can be selected to provide a stimulus or to provide therapy to a subject or patient based on the size of the region of the blood vessel into which the implant is to be deployed. In some cases, an implant having an $L_D$ of 17.8 mm to 18.2 mm, an $L_c$ of 18.7 mm, a W of 7.27 mm, a D of 8.49 mm, or an unconstrained cross-sectional area of from 52.85 $mm^2$ to 56.60 $mm^2$ can be used to provide a stimulus or a therapy to a target region in a vessel having a diameter of from 3 mm to 8 mm. Similarly, an implant having an $L_D$ of 19.9 mm to 20.8 mm, an $L_c$ of 21.4 mm, a W of 8.28 mm, a D of 9.78 mm, or an unconstrained cross-sectional area of from 68.56 $mm^2$ to 75.12 $mm^2$ can be used to provide a stimulus or a therapy to a target region in a vessel having a diameter of from 5 mm to 10 mm. An implant having an $L_D$ of 18.6 mm to 20.0 mm, an $L_c$ of 21.1, a W of 10.22 mm, a D of 12.25 mm, or an unconstrained cross-sectional area of from 104.45 $mm^2$ to 117.86 $mm^2$ can, in some cases, be used to provide a stimulus or a therapy to a target region in a vessel having a diameter of from 7 mm to 13 mm. In some cases, it can be beneficial to test the effect of multiple implant sizes or geometries on a target region (e.g., blood vessel) of a given size or dimension. For example, because a plurality of implants having different sizes and/or geometries can be indicated for the provision of a stimulus or therapy to a blood vessel of a given diameter, it may be beneficial to apply a stimulus to a target region of the blood vessel using a plurality of different implants and/or to measure a physiological parameter in response to the stimulus (e.g., in order to determine an optimal level, value, or change of a measured or sensed physiological parameter for the stimulus, implant, target region, or subject or patient).

A target region to which a stimulus or therapy can be provided in accordance with the methods, devices, and systems described herein can comprise a region (e.g., a target region of blood vessel) having an inner or outer diameter of less than 2 mm, from 2 mm to 3 mm, from 3 mm to 4 mm, from 4 mm to 5 mm, from 5 mm to 6 mm from 6 mm to 7 mm, from 7 mm to 8 mm, from 8 mm to 9 mm, from 9 mm to 10 mm, from 10 mm to 11 mm, from 11 mm to 12 mm, from 12 mm to 13 mm, from 13 mm to 14 mm, from 14 mm to 15 mm, from 15 mm to 16 mm, from 16 mm to 17 mm, or more than 17 mm.

An implant can comprise an expandable scaffold. An expandable scaffold can be expanded or collapsed (e.g., crimped) in various ways, such as those described herein. For example, an implant comprising an expandable scaffold can be collapsed (e.g., crimped or compressed) within a delivery device prior to being partially deployed, fully deployed, or repositioning at a target region and allowed to expand at the target region during full or partial deployment.

An expandable scaffold can be a self-expanding scaffold, an actively-controlled expandable scaffold, or a combination of the two. A self-expanding scaffold can comprise a scaffold that expands passively. For example, a self-expanding scaffold may expand, unfold, or enlarge when constrictive or enclosing forces and/or structures are removed from the immediate vicinity of the scaffold (e.g., through the release of potential energy from one or more flexed or collapsed living hinge). An actively-controlled expandable scaffold can be a scaffold wherein the degree to which the scaffold is expanded, collapsed, or retracted can be controlled directly by a user or automatically by a computer system (e.g., by a controller of a computer system operating according to instructions stored in a memory of the computer). For example, a system or method comprising an actively-controlled scaffold can comprise a core wire attached to a portion of the scaffold (e.g., a distal or proximal end of the scaffold), wherein application of force to pull or push on the core wire can be used to expand, to collapse, or to retract the scaffold.

An expandable scaffold of an implant can comprise a plurality of struts (e.g., vessel-contacting struts) and a plurality of crimping regions, and a plurality of non-contact regions). An implant comprising an expandable scaffold can comprise 3, 4, 5, 6, 7, 8, 9, 10 struts, or, from 3 to 7 struts, from 4 to 8 struts, or from 10 to 24 struts (e.g., vessel- or artery-contacting struts). An implant can also comprise 2, 4, 6, 8, 10, 12, 14, 16, 18, 20, 22, or 24 crimping regions. A first strut of an implant can be connected to a second strut of the implant by a pivoting hinge (e.g., a hinge comprising two or more separate pieces that are able to pivot around a common axis) or a living hinge (e.g., a single, continuous structure wherein two or more elements are joined by a flexible region). A strut can also be connected to a crimping region by a pivoting hinge or a living hinge. A crimping region or crimping arch can comprise a living hinge.

An implant comprising an expandable scaffold can be configured to alter the geometry and/or cross-section of a target region when partially or fully deployed. In some cases, an alteration to the geometry or cross-sectional area of a target region can comprise a mechanical stimulus. For example, an implant comprising an expandable scaffold may provide a mechanical stimulus to a target region when fully or partially deployed at the target region. In some cases, a mechanical stimulus provided to a target region by a partially or fully deployed implant can be mediated by a force imparted on the target region by one or more structure of the implant (e.g., a vessel- or artery-contacting region of an implant, such as a strut or crimping region). In some cases, a force that comprises a mechanical stimulus can be generated by the flexure or crimping of a living hinge of the implant.

A mechanical stimulus as described herein can comprise an equal or an unequal application of force around the interior or exterior circumference of a blood vessel. For example, an implant can exert greater force on a vessel wall at a contact region than at a non-contact region. Accordingly, strain in a target region may be equal or unequal around the interior or exterior circumference of a blood vessel. For example, a plurality of vessel-contacting struts of an implant can strain or deform a vessel wall such that the radius of curvature of a first region (e.g., a non-contact region) of the vessel wall is increased and the radius of curvature of a second region (e.g., a contact region) of the vessel wall is decreased when the implant is fully or partially deployed at a target region.

Providing a mechanical stimulus to a blood vessel with an implant, as described herein, can result in a plurality of regions along a circumference of the blood vessel in which the radius of curvature is increased. In some cases, providing a mechanical stimulus to a blood vessel with an implant, as described herein, can result in at least 2 regions, at least 3 regions, at least 4 regions, at least 5 regions, at least 6 regions, at least 7 regions, at least 8 regions, at least 9 regions, at least 10 regions, less than 25 regions, less than 20 regions, less than 15 regions, less than 10 regions, less than 8 regions, less than 4 regions, from 2 to 24 regions, from 2 to 10 regions, from 3 to 7 regions, or from 4 to 8 regions of the blood vessel having an increased radius of curvature.

Providing a mechanical stimulus to a blood vessel with an implant can also result in a plurality of regions along a circumference of the blood vessel in which the radius of curvature is decreased. In some cases, providing a mechanical stimulus to a blood vessel with an implant, as described herein, can result in at least 2 regions, at least 3 regions, at least 4 regions, at least 5 regions, at least 6 regions, at least 7 regions, at least 8 regions, at least 9 regions, at least 10 regions, less than 25 regions, less than 20 regions, less than 15 regions, less than 10 regions, less than 8 regions, less than 4 regions, from 2 to 24 regions, from 2 to 10 regions, from 3 to 7 regions, or from 4 to 8 regions of the blood vessel having a decreased radius of curvature. In some cases, one or more region of increased curvature along a blood vessel's circumference can alternate with one or more region of decreased curvature along a blood vessel's circumference.

In some cases, a mechanical stimulus provided to a target region by an implant can increase the target region's cross-sectional area. In some cases, the cross-sectional area of a target region may not change as a result of a mechanical stimulus applied to the target region by the implant.

A stimulus can be applied to a target region acutely (e.g., transient application of the stimulus) or chronically (e.g., long-term application of the stimulus). Transient application of a stimulus can comprise applying a stimulus to a target region for less than 1 minute, less than 2 minutes, less than 3 minutes, less than 4 minutes, less than 5 minutes, less than 6 minutes, less than 7 minutes, less than 8 minutes, less than 9 minutes, less than 10 minutes, less than 30 minutes, less than 1 hour, less than 2 hours, from 0 to 1 minute, from 1 to 2 minutes, from 2 to 3 minutes, from 3 to 4 minutes, from 4 to 5 minutes, from 5 to 6 minutes, from 6 to 7 minutes, from 7 to 8 minutes, from 8 to 9 minutes, from 9 to 10 minutes, from 10 to 30 minutes, from 30 to minutes to 1 hour, or from 1 hour to 2 hours. For example, transient application of a mechanical stimulus can be accomplished by partially or fully deploying an implant at a target region for less than one hour, as described herein. Long-term application of a stimulus can comprise applying a stimulus to a target region for less than 3 hours, less than 6 hours, less than 9 hours, less than 12 hours, less than 1 day, less than 2 days, less than 3 days, less than 4 days, less than 5 days, less than 6 days, less than 7 days, at least 7 days, at least 2 weeks, at least 3 weeks, at least 4 weeks, at least 5 weeks, greater than 1 month, or greater than 1 year. For example, long-term application of a mechanical stimulus can be accomplished by fully deploying an implant at a target region for at least 1 week. Providing a therapy to a subject or patient can comprise providing a long-term stimulus to the subject or patient.

Providing a stimulus to a target region can comprise withdrawing the stimulus following transient or long-term application of the stimulus. For example, providing a mechanical stimulus to a target region can comprise collapsing, retracting, or withdrawing an implant after transient or long-term application of the mechanical stimulus.

In some cases, and as further described herein, providing a stimulus can comprise deploying a second implant at a target region after retracting or withdrawing a first implant. In some cases, the second implant can be partially or fully deployed at the same target region as the first implant or at a different target region than the first implant. In some cases, the second implant can cause a different mechanical stimulus than the first implant (e.g., as a result of differences in the size or geometry of the second implant relative to the first implant or as a result of the length of time or the degree to which the first or second implant is deployed). For example, a second implant can be deployed at a target region after a first implant is retracted from the target region in order to alter the radius of curvature of the target region differently with the second implant than was possible with the first implant (e.g., because of the relative size or geometry of the second implant relative to that of the first implant).

Figure 37A:
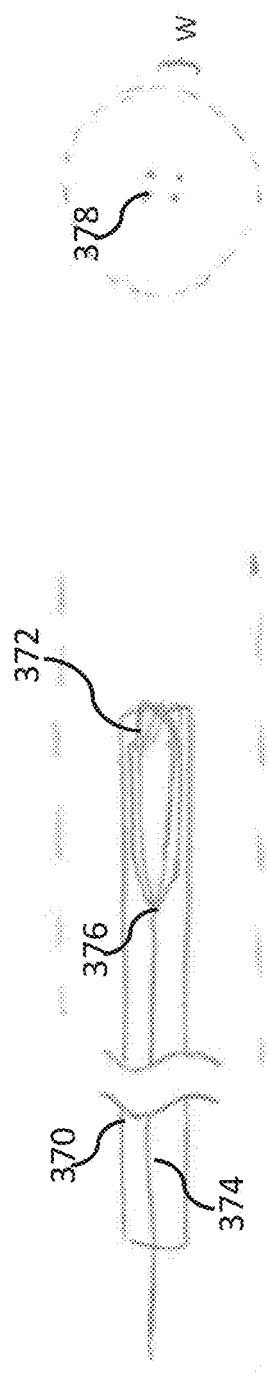
FIGS. 37A-37D are schematic illustrations of devices and steps useful in the screening of a subject or patient for therapy, in accordance with some applications of the present disclosure.
Figure 37B:
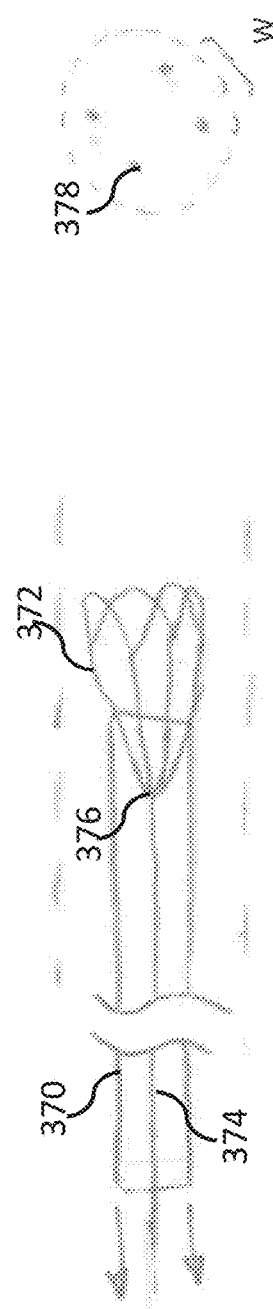
Figure 37C:
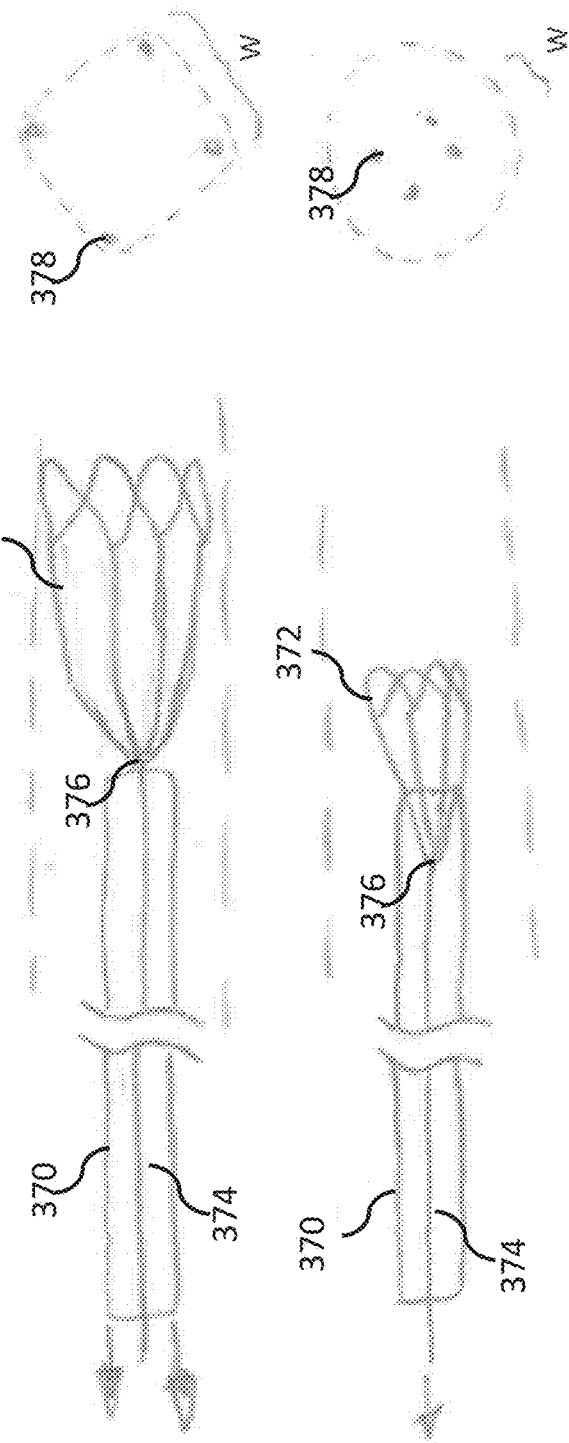
Figure 37D:
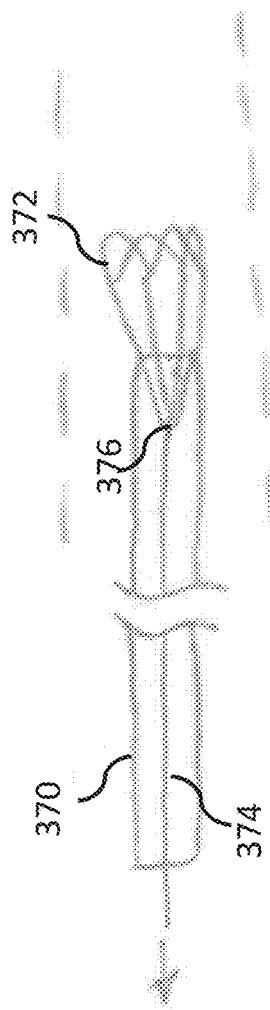

Referring now to FIGS. 37A-37D, an example is shown of full deployment of an implant 372 at a target location. Implant 372 can be an implant or intra-arterial device described herein (e.g., device 120, 160, and/or 190). Delivery device 370 can be inserted into a target area (e.g., a blood vessel, as indicated by dotted line) with implant 372 collapsed or crimped inside of the delivery device. The proximal end 376 of implant 372 can be connected to a tether 374, while the distal end of implant 372 can be free. In accordance with the methods and systems described herein, implant 372 can be partially or fully deployed at a target region (see, for example, FIGS. 37B and 37C). Implant 372 may be deployed by retracting delivery device 370 or a retractable sheath of delivery device 370. Implant 372 may also be deployed by pushing the implant out of the delivery device (e.g., by applying pressure to the proximal end of tether 374, not shown in FIGS. 37A-37D). As implant 372 is deployed from delivery device 370, a portion of implant 372 can expand (e.g., the free distal end of implant 372). As implant 372 expands during deployment, one or more portion of implant 372 (such as a plurality of artery-contacting struts; see, for example, vertices 378) may contact the target region at one or more contact region. Deployment of implant 372 may increase the width (W), diameter, perimeter, or cross-sectional area of implant 372. Deployment of implant 372 may also decrease the longitudinal length of implant 372. Contact between a portion of implant 372 can cause strain and/or deformation in the target region (e.g., as seen in FIG. 37C). As described herein, contact between implant 372 and the target region can comprise a mechanical stimulus to baroreceptors at or in the vicinity of the target region. As shown in FIG. 37D, implant 372 can be retracted into the delivery device (e.g., by pulling on tether 374), and the implant can either be repositioned or withdrawn from the target location along with the delivery device.

Figure 38C:
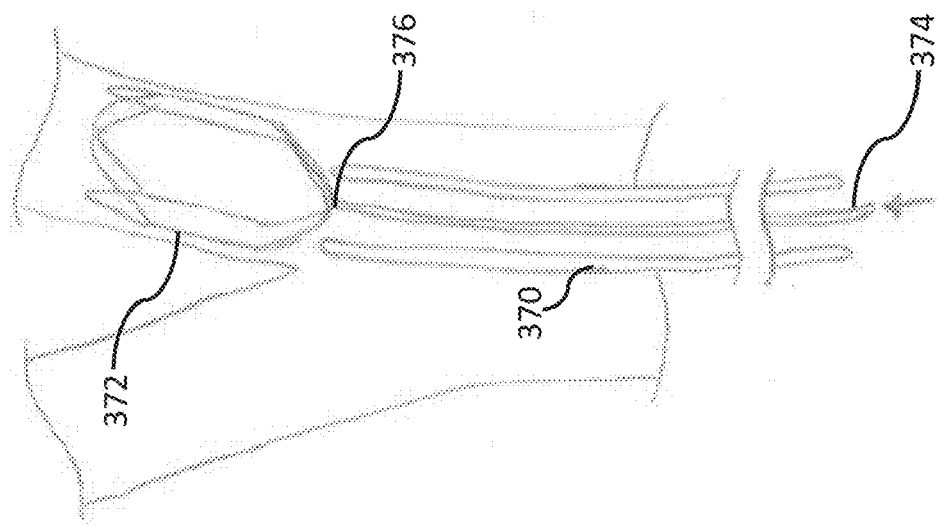
FIGS. 38A-38F are schematic illustrations of steps in the use of a system for the screening of a subject or patient for therapy, in accordance with some applications of the present disclosure.
Figure 38B:
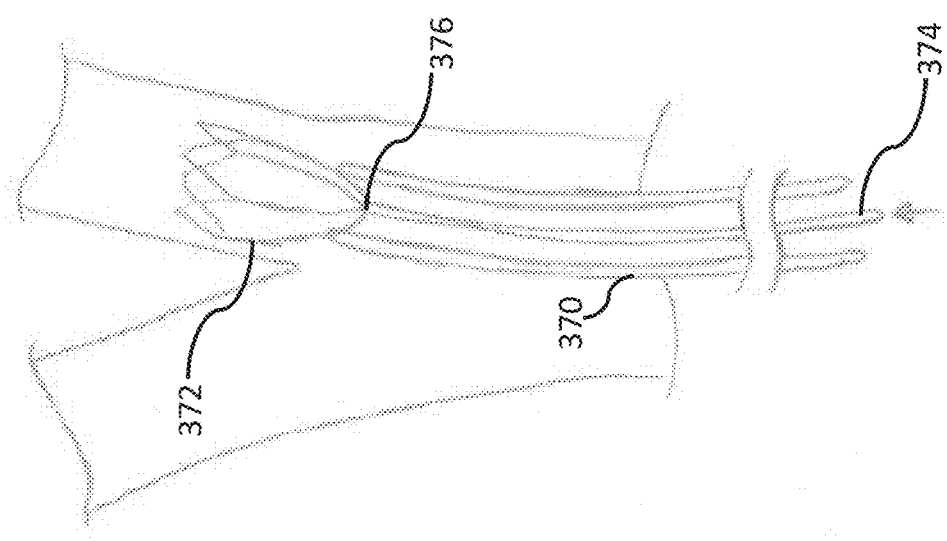
Figure 38A:
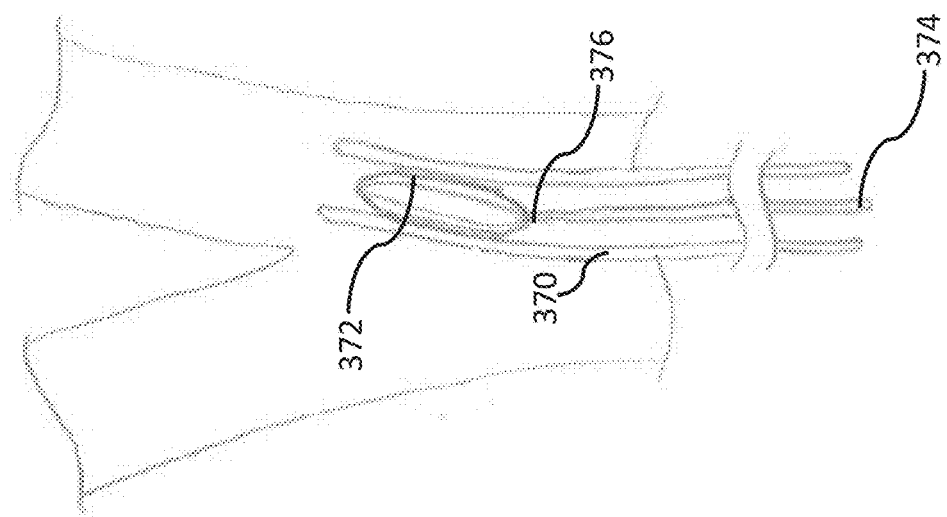
Figure 38F:
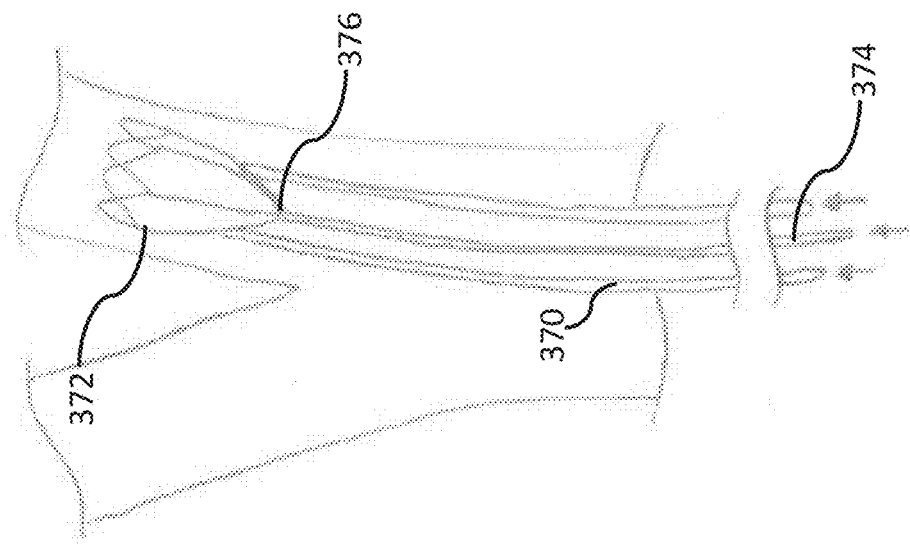
Figure 38E:
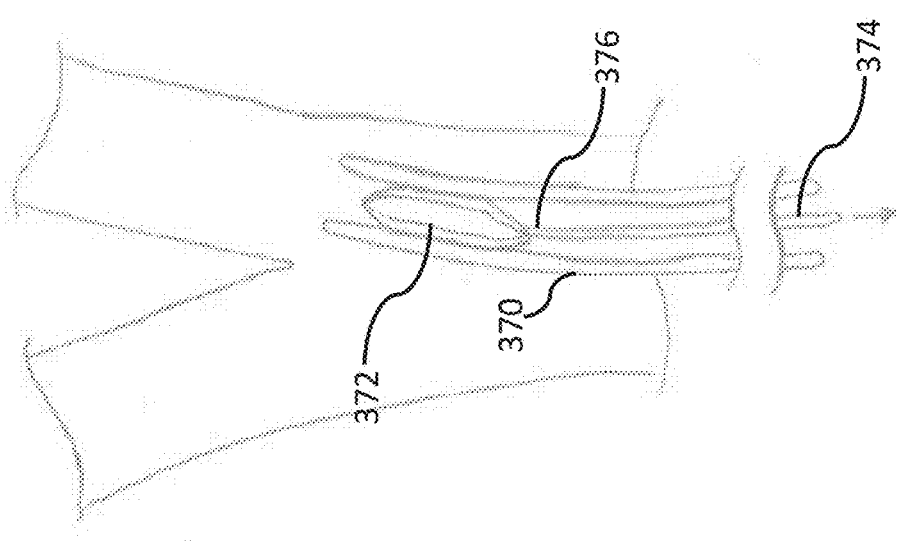
Figure 38D:
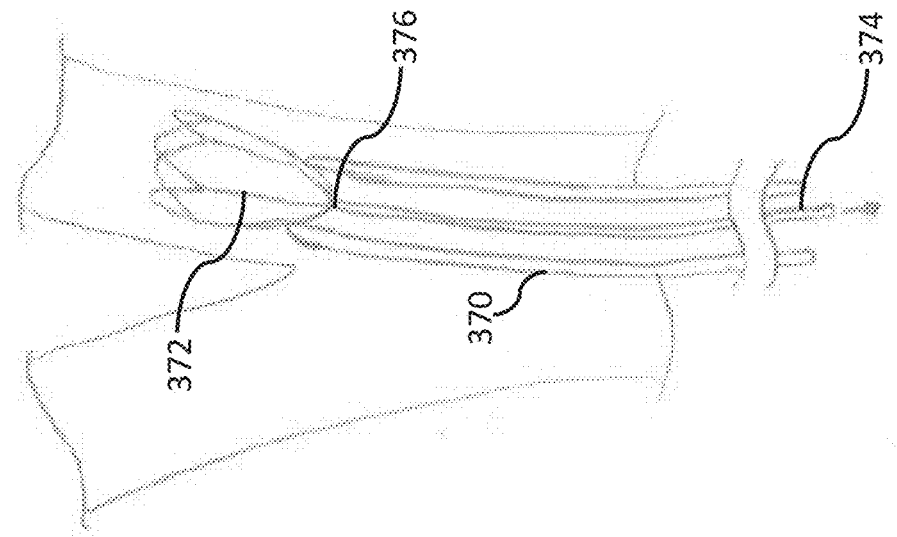

FIGS. 38A-38F show steps in the use of a system for applying a stimulus to a target region, comprising deploying implant 372 at a target region. Implant 372 can be advanced to a target region inside of delivery device 370 (e.g., as in FIG. 38A) and then either partially or fully deployed at the target location (see, for example, FIG. 38B and FIG. 38C, respectively). As described herein, implant 372 may contact a target area when partially or fully deployed, which may cause strain or deformation at the target region and, potentially, changes to one or more physiological parameter, including baroreceptor activity and/or blood pressure. FIG. 38B and FIG. 38C show deployment of implant 372 from delivery device 370 being accomplished by pushing on tether 374; however, retraction of delivery device 370 or of a retractable sheath of delivery device 370 can also comprise a step in deploying the implant from the delivery device. Examples of steps for retracting implant 372 into delivery device 370 can be seen in FIG. 38D and FIG. 38E. As shown in FIG. 38F, for example, the implant and/or delivery device can be repositioned in the subject or patient, and the implant can subsequently be redeployed, either partially or fully at a location (e.g., a second target region). Alternatively, delivery device 370 may be removed from the subject or patient with or without implant 372.

Referring now to FIGS. 39A-39C, an example of deployment of an implant (e.g., an intra-vascular device, as described herein) is shown. Optionally, a portion of implant 372 may be in contact with delivery device 370 (e.g., at point 394). As shown in FIGS. 39A-39C, implant 372 can be connected to delivery device 370 at point 394. For example, point 394 can be a hinge (e.g., a pivoting hinge or a living hinge) connecting delivery device 370 to implant 372. Hinge 396 can be a pivoted hinge or living hinge connecting two or more portions of implant 372. For example, hinge 396 can join a strut to a strut or a strut to a crimping arch or crimping region. As shown in FIGS. 39A-39C, implant 372 can comprise a core wire 390. Core wire 390 may be fixed to the distal end 392 of implant 372. As shown in FIG. 39B, implant 372 can be deployed or expanded by applying tension to core wire 390. In some cases, applying tension to core wire 390 can cause hinge 396 and/or hinge 394 to flex. Flexure or relaxation of hinge 396 and/or hinge 394 (e.g., through the application or release of tension to core wire 390) may modulate the width (W), perimeter, or cross-sectional area of implant 372. Flexure or relaxation of hinge 396 and/or hinge 394 may affect the longitudinal length of implant 372, as exemplified in FIG. 39A-39C. Flexure of hinge 396 and/or hinge 394 can bring one or more portion of implant 372 into contact with the target region (e.g., a contact region of a vessel wall). As described herein, contact between one or more portion of implant 372 can cause strain and/or deformation of the target region. As further described herein, contact between one or more portion of implant 372 and the target region can modulate one or more physiological parameter, such as baroreceptor activity and/or blood pressure. Implant 372 can be repositioned or withdrawn by releasing tension on core wire 390 or by pushing core wire 390.

FIGS. 40A-40E show steps in the use of a system for applying a stimulus to a target region. As described herein, implant 372 may be advanced through the vasculature to a target region, wherein implant 372 may be deployed. In some cases, point 394 can be an unpinned point of contact between delivery device 370 and implant 370, wherein a portion of implant 370 (e.g., a strut or portion of a crimping arch) is free to slide over the distal end of delivery device 370. Core wire 390 may be joined to implant 372 at the distal end 392 or at the proximal end of implant 372. As described herein, application of tension to core wire 390 can cause flexure of hinges 396 and an increase in the width and/or cross-sectional area of the implant. As a result, application of tension to core wire 390 can cause one or more portion of implant 390 to contact the target region (e.g., at one or more contact region), which can provide a stimulus to the target region. Implant 372 can be repositioned or withdrawn by releasing tension on core wire 390 and adjusting the positioning of delivery device 370.

Figure 41:
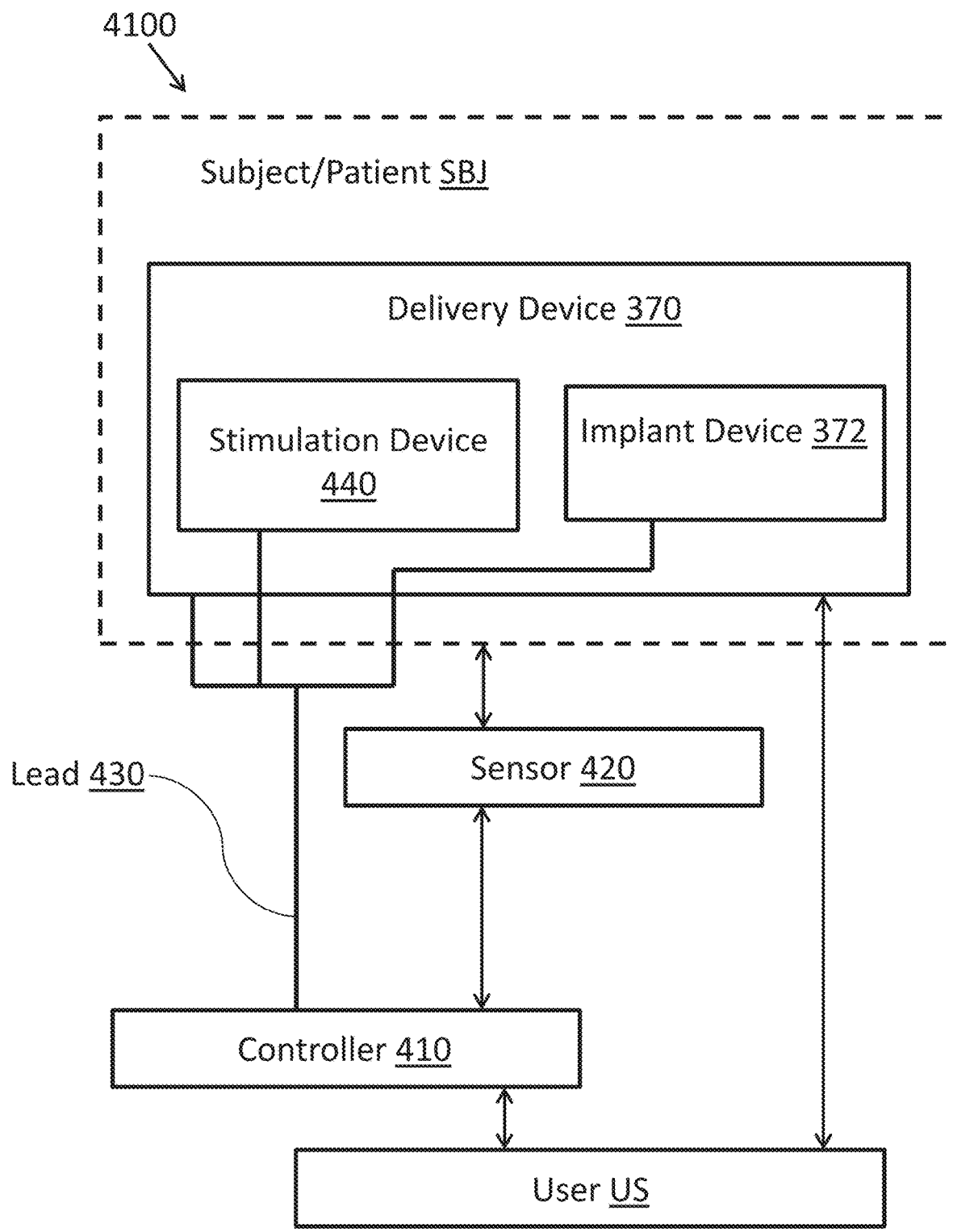
FIG. 41 is a schematic of a system for screening a subject or patient for therapy, in accordance with some applications of the present disclosure.

As shown in FIG. 41, system 4100 can comprising delivery device 370 and may be used to provide a stimulus to a subject/patient SBJ or to measure or sense one or more physiological parameter from subject/patient SBJ. The system 4100 may further comprise a controller 410 that may couple to the lead 430. The lead 430 may be coupled to one or more of the implant device 372, the delivery device 370, or an optional stimulation device 440. Optional stimulation device 440 may comprise a means for applying a non-mechanical stimulus to the patient (e.g., at the target region), as described herein. The controller 410 may generate a stimulation signal, such as an electrical or thermal stimulation signal, to be conveyed through the lead 430 and, optionally, through the implant device 372, the stimulation device 440, and/or the delivery device 370 to the target region of the vasculature. Alternatively or in combination, the controller 410 may generate a current which may be conveyed through at least the lead 430 to image or electrically map the target region of the vasculature, as described herein. Alternatively or in combination, the stimulation signal may simply be mechanical, such as contact on or pressure exerted onto the inner wall of the carotid artery by a partially or fully deployed implant 372. System 4100 may further comprise a sensor 341, which may be an extravascular or extracorporeal sensor, for measuring or determining baroreceptor activity. External sensor 420 may comprise one or more means of measuring or sensing one or more physiological parameter, including a heart rate monitor, a blood pressure monitor (such as an external blood pressure sensor, an intra-arterial blood pressure sensor (i.e., an arterial line), or a blood pressure sensor connected an arterial line of the delivery device 372 or other catheter), a plurality of electrodes for ECG or EEG, a blood flow rate monitor (e.g., using ultrasound), a blood flow velocity monitor (e.g., using ultrasound), an oxygenation sensor (e.g., a pulse oximeter or other optical detector), a vasoactivity sensor, a nerve activity sensor, a piezo electric pressure transducer, a membrane pH electrode, or a strain gage, to provide a few examples. The user US may operate and monitor the controller 410 and optionally the sensor Experimental Data A number of experiments were conducted by the inventors in accordance with the techniques described herein.

In one experiment, acute unilateral carotid stimulation was applied to a first set of dogs, either the left or right carotid sinus of the dogs of the first set being squeezed between two smooth metal plates for a period of two to five minutes. Acute bilateral carotid stimulation was applied to a second set of dogs, both carotid sinuses of the dogs of the second set being squeezed between two smooth metal plates for a period of 10 to 30 minutes. The mean effect of the unilateral carotid sinus stimulation was to decrease systolic blood pressure by 11 mmHg, and the mean effect of the bilateral stimulation was to decrease systolic blood pressure by 29 mmHg. The results of the bilateral stimulation had a p-value of less than 0.001. These results indicate that using the devices described herein for either unilateral or for bilateral carotid sinus stimulation may be effective at reducing a subject's blood pressure.

In another experiment, two dogs were chronically implanted (for periods of more than two months) with plates that squeezed the carotid sinus, in accordance with the techniques described herein. The dogs had the plates implanted around both carotid sinuses. On a first one of the dogs, the plates became dislodged from one of the sinuses within two days of implantation. The plates remained implanted around both carotid sinuses of the second dog, until the plates were removed. The blood pressure of the dogs was measured, via an implanted telemeter, for two to four weeks before the device implantation. In the first dog, the dog's blood pressure was measured after the implantation of the device for two weeks, and was subsequently terminated, due to a malfunction in the transmission of the telemeter. In the second dog, the dog's blood pressure was measured for six weeks after the implantation of the device.

For the dog that had the plates chronically implanted around only one carotid sinus, the average diastolic blood pressure measured in the dog over two weeks post-implantation was 6 mmHg less than the average diastolic blood pressure measured in the dog over two weeks pre-implantation. The average systolic blood pressure measured in the dog over two weeks post-implantation was 8 mmHg less than the average systolic blood pressure measured in the dog over two weeks pre-implantation.

For the dog that had the plates chronically implanted bilaterally, the average diastolic blood pressure measured in the dog over six weeks post-implantation was 10 mmHg less than the average diastolic blood pressure measured in the dog over two weeks pre-implantation. The average systolic blood pressure measured in the dog over six weeks post-implantation was 18 mmHg less than the average systolic blood pressure measured in the dog over two weeks pre-implantation.

These results indicate that chronic implantation of the devices described herein for either unilateral or for bilateral carotid sinus stimulation may be effective at chronically reducing a subject's blood pressure.

In addition to measuring the blood pressure of the dog that had plates chronically implanted bilaterally around its carotid sinuses, the inventors measured the baroreceptor sensitivity of the dog, for several weeks, both pre-implantation and post-implantation of the device using generally similar techniques to those described in "The effect of baroreceptor activity on cardiovascular regulation," by Davos (Hellenic J Cardiol 43: 145-155, 2002), which is incorporated herein by reference. Pre-implantation of the device, the mean baroreceptor sensitivity was 14±5 sec/mmHg. Post-implantation of the device, the mean baroreceptor sensitivity was 20±8 sec/mmHg. These results indicate that chronic implantation of the devices described herein may be effective at increasing baroreceptor sensitivity.

In a further experiment that was conducted in accordance with the techniques described herein, five human patients had a device placed around either the left or right carotid sinus, subsequent to undergoing endarterectomy procedures. The device was configured to flatten regions of the wall of the carotid sinus, in accordance with techniques described herein. Of the five patients, two were excluded from the study, since these patients were administered atropine, which may have interfered with the results. Of the three patients who were included in the study, the placement of the device in all of the patients resulted in a decrease in both the systolic and diastolic blood pressure of the patient. For the three patients who were included in the study, the placement of the device resulted in a mean decrease in diastolic blood pressure of 8 mmHg (standard deviation 5) and a mean decrease in systolic blood pressure of 22 mmHg (standard deviation 14), relative to the blood pressures before placement of the device. These results indicate that using the devices described herein for carotid sinus stimulation may be effective at reducing a human subject's blood pressure.

Figure 31A:
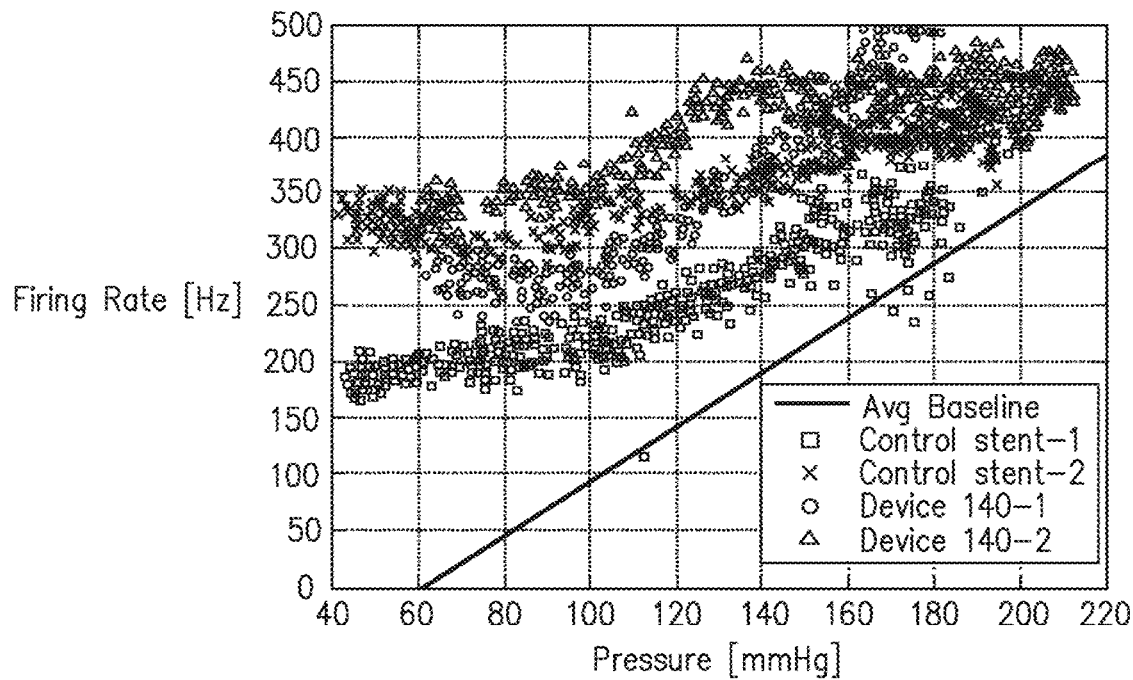
FIGS. 31A-31B are graphs showing the Herring's nerve firing rate at respective blood pressures recorded in dogs that had been implanted with medical devices, in accordance with some applications of the present disclosure.
Figure 31B:
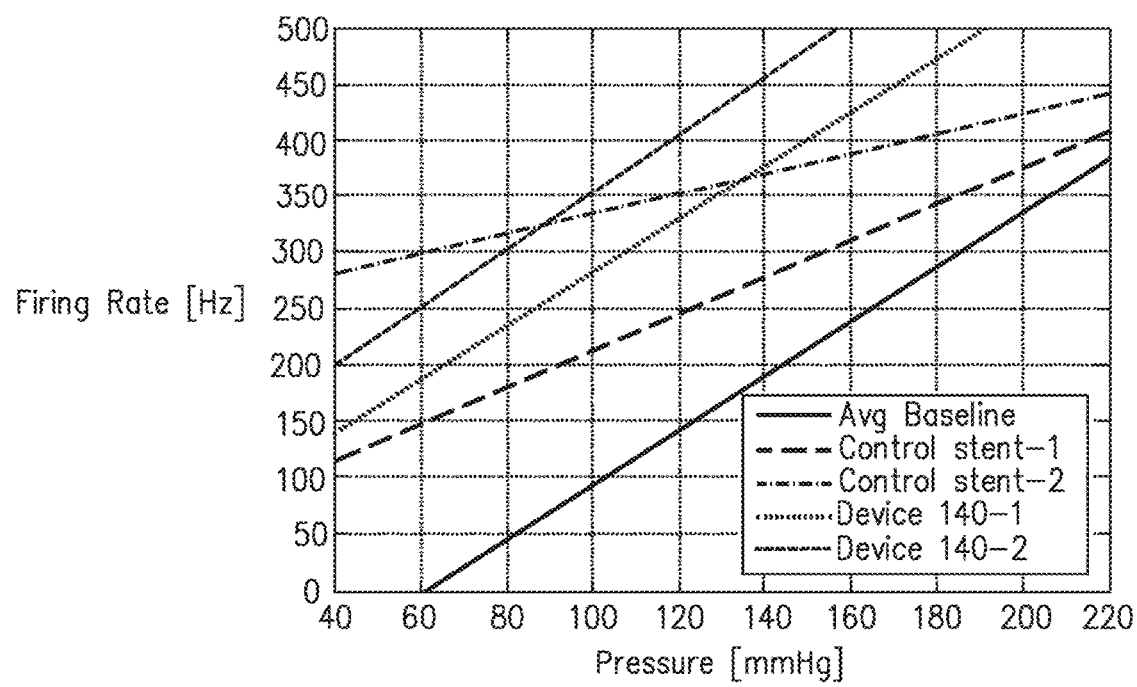

Reference is now made to FIGS. 31A-B, which are graphs showing the herring's nerve firing rate at respective blood pressures recorded in dogs that had been implanted with medical devices, in accordance with some applications of the present disclosure. Reference is also made to FIGS. 32A-B, which are graphs showing the herring's nerve integrated nerve activity at respective blood pressures recorded in dogs that been implanted with medical devices, in accordance with some applications of the present disclosure Four dogs were used in the experiments. In each of the dogs, one femoral artery was accessed with a 6 Fr sheath for the purposes of catheterization, and the contralateral femoral artery was accessed with a 4 Fr sheath, via which invasive blood pressure monitoring was performed. In three out of the four dogs, bilateral vagotomy was performed before the carotid artery was exposed, by complete cutting of the vagus nerve approximately 6 cm caudal to the level of the neck dissection. Unilateral exploration of the neck was directed to the hypogloseal nerve and lingual artery. The hypogloseal nerve and lingual artery were cut such as to expose the plane at which the herring's nerve crosses to join the carniocervical ganglion. Following identification of herring's nerve, the nerve was desheathed and divided to micro bundles under a surgical microscope. The nerve bundle was isolated and placed on an electrode.

The nerve biopotentials at respective blood pressures was recorded (a) on the native, untreated carotid sinus (i.e., baseline recordings), and (b) following implantation in the carotid sinus of either a device that is similar to device 140 (FIGS. 17A-D), or a control stent. Each event recording was initiated at a low blood pressure (e.g., systolic blood pressure of approximately 60 mmHg). The blood pressure was lowered via continuous intravenous infusion of nitroglycerine 1.2 mcg/kg/min. During the event recording, the blood pressure of the dog was gradually raised by continuous intravenous infusion of phenylephrine 150 mcg/kg/min, the dosage of which was gradually increased. When the event recording was completed for the native carotid sinus, a device similar to device 140, or a control stent, was endovascularly implanted in the carotid sinus. An event recording was performed subsequent to the device implantation, the event recording being as described above. In two of the dogs, subsequent to performing the event recording after the implantation of the first device in the carotid sinus, the other type of device was implanted within the contralateral carotid sinus, and the event recording as described hereinabove was then repeated. All of the dogs were euthanized at the end of the procedures.

FIG. 31A shows (a) a line that plots the average firing rate of the dogs' herring's nerves during the baseline recordings, in addition to (b) two sets of raw nerve firing rate recordings that were recorded subsequent to the implantation of a device that is similar to device 140 into two of the dogs, and (c) two sets of raw nerve firing rate recordings that were recorded subsequent to the implantation of control stents into two of the dogs. Each of the raw data points in FIG. 31A is based on data averaged over a 1 second running interval. FIG. 31B shows a linear fit of the region of interest of the raw data for each of the experiments. The linear fit assumes that overall shape of the curve is sigmoid, and that the region of interest is in the sloped region of the sigmoid. The flat portions at pressures above and below the region of interest were assumed to be saturation regions, the effect of the implanted devices being limited within these regions. In all cases, the transition from the flat portion of the sigmoid to the linear slope was assumed to be at approximately 100 mmHg. For the device indicated as device 140-2 in FIGS. 31A-31D, it was assumed that at pressures above 140 mmHg, the effect of the device was saturated, and the data corresponding to this region were not used in the generation of the linear fit line for this device. For all other event recordings, it was assumed that the upper saturation region was not reached within the blood pressure range that was generated during the experiment. It is noted that the size of the device indicated as device 140-2 in FIGS. 31A-31D was too small for the carotid sinus in which the device was implanted. This may be the reason why the response curve for this device appears to have an upper saturation region from a pressure of approximately 140 mmHg.

It is noted that there was a discontinuity in the data recorded during the event recording for the device indicted by control stent-2 in FIGS. 31A-31D. The experiment that was conducted with control stent-2 was prolonged due to technical issues, which caused increased bleeding of the animal. This gave rise to electronic noise that was captured by the electrodes and which caused a discontinuity in the data. The discontinuity was corrected for in the data plotted in FIGS. 31A-31D.

It is noted that experimental data for one of the dogs are not shown. This is because one of the dogs did not undergo a vagotomy. Therefore, the administration of nitroglycerine and phenylephrine to the dog (which was performed in order to induce changes in the dog's blood pressure, as described above) did not substantially affect the dog's blood pressure. The experimental results from this dog are not included in the data shown in FIGS. 31A-31D.

In addition, in a second one of the four dogs, only the control stent deployed correctly, and in a third one of the dogs, only the device that was similar to device 140 was deployed due to difficulties in locating the nerve innervating the carotid sinus on the dog. Therefore, for the second dog, experimental results for the device that was similar to device 140 are not included in the data shown in FIGS. 31A-31D, and, for the third dog, experimental results for the control stent are not included in the data shown in FIGS. 31A-31D.

Figure 31C:
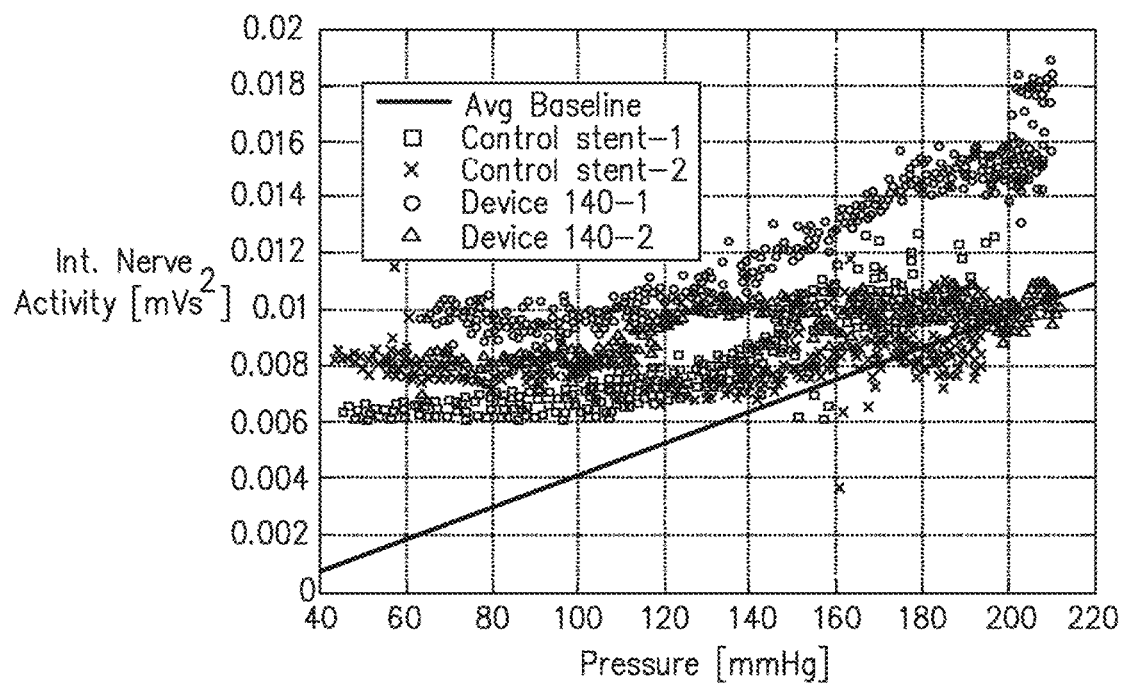
FIGS. 31C-31D are graphs showing the Herring's nerve integrated nerve activity at respective blood pressures recorded in dogs that been implanted with medical devices, in accordance with some applications of the present disclosure.
Figure 31D:
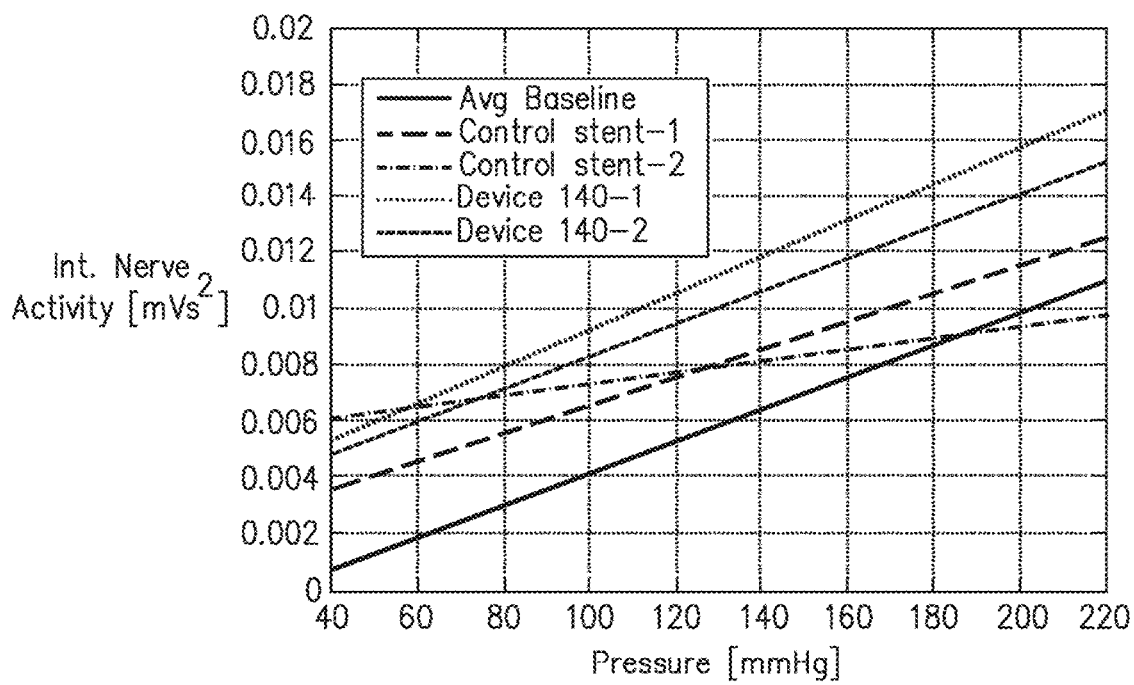

FIGS. 31C-31D are generally similar to FIGS. 31A-31B respectively but show the integrated nerve activity recorded in the dogs' herring's nerves during the events, rather than the nerve firing rates.

As indicated in FIGS. 31A-31D, the effect of the implantation of both device 140 and the control stent in the dogs' carotid sinuses resulted in a shift of the response curve of the herring's nerve to lower pressures. This is because, at all blood pressures, the implanted devices increase nerve activity by deforming the carotid sinus, thereby increasing baroreceptor stimulation. The shift in the response curve resulting from the implantation of device 140 is greater than that resulting from the implantation of the control stents. In addition, the shapes of the response curves indicate that implantation of device 140 resulted in a steeper nerve response curve than the response curve that resulted from the implantation of the control stents. The shape of the response curve resulting from the implantation of device 140 is similar in shape to the shape of the baseline curve.

The results shown in FIGS. 31A-31D indicate that the devices described herein are effective at (a) shifting the baroreceptor response curve of a subject toward lower blood pressures, without (b) substantially impairing (and possibly improving) the responsiveness of the baroreceptors to changes in blood pressure. The inventors hypothesize that the implantation of the devices described herein do not substantially impair, and may even improve, the responsiveness of the baroreceptors to changes in blood pressure, since the devices are shaped such as to maintain pulsatility of the carotid artery, subsequent to implantation of the devices inside the carotid artery. The inventors hypothesize that by maintaining the natural arterial baroreceptor response curve, the devices described herein may prevent long-term resetting of the responsiveness of the baroreceptors subsequent to device implantation. Alternatively, it is possible that in the experiments described with reference to FIGS. 31A-31D, the devices activated the high pressure c-fibers which are not normally activated and do not reset.

The scope of the present disclosure includes combining the apparatus and methods described herein with those described in US 2008/0033501 to Gross, WO 10/035271 to Gross, US 2011/0213408 to Gross, US 2011/0077729 to Gross, and/or US 2011/0178416 to Gross, all of which applications are incorporated herein by reference.

It will be appreciated by persons skilled in the art that the present disclosure is not limited to what has been particularly shown and described hereinabove. Rather, the scope of the present disclosure includes both combinations and subcombinations of the various features described hereinabove, as well as variations and modifications thereof that are not in the prior art, which would occur to persons skilled in the art upon reading the foregoing description.

What is claimed is:

1. A method of screening a subject for a therapy, the method comprising:
   providing at least one mechanical stimulus to a blood vessel, the at least one mechanical stimulus generating at least a first region of the blood vessel having increased radius of curvature and at least a second region of the blood vessel having decreased radius of curvature, wherein the at least one mechanical stimulus is provided intra-vascularly, and wherein providing the at least one mechanical stimulus comprises advancing a mechanical stimulus device through vasculature of the subject to a target location;
   detecting at least one change in at least one physiological parameter in response to the provided at least one mechanical stimulus; and
   selecting an implant to provide the therapy to the subject based on the detected at least one change in the at least one physiological parameter, wherein at least the first region of the blood vessel having increased curvature comprises a plurality of first regions having increased radius of curvature, wherein at least the second region of the blood vessel having decreased curvature comprises a plurality of second regions having decreased radius of curvature, and wherein the first and second regions alternate with one another around a circumference of the blood vessel.

2. The method of claim 1, wherein the target location is located in a carotid artery, carotid sinus, aorta, aortic arch, subclavian artery, cranial artery, heart, or common artery of the subject.

3. The method of claim 1, wherein the at least the first region of the blood vessel having increased radius of curvature comprises at least one region of the blood vessel with increased strain.

4. The method of claim 1, wherein the at least the second region of the blood vessel having decreased radius of curvature comprises at least one region of the blood vessel with increased strain.

5. The method of claim 1, wherein providing the at least one mechanical stimulus comprises deploying a first implant from the mechanical stimulus device to the target location, the implant increasing the curvature of at least the first region of the blood vessel and decreasing curvature of at least the second region of the blood vessel.

6. The method of claim 5, wherein providing the at least one mechanical stimulus further comprises retracting the first implant from the target location.

7. The method of claim 6, wherein the first implant is retracted from the target location after a time period of between 0 minutes and 1 minute, from 1 minute to 2 minute, from 2 minutes to 3 minutes, from 3 minutes to 4 minutes, from 4 minutes to 5 minutes, from 5 minutes to 10 minutes, from 10 minutes to 20 minutes, from 20 minutes to 30 minutes, from 30 minutes to 1 hour, or from 1 hour to 2 hours.

8. The method of claim 6, wherein providing the at least one mechanical stimulus further comprises deploying a second implant from the mechanical stimulus device to the target location after the retracting the first implant, the second implant increasing the curvature of at least the first region of the blood vessel and decreasing curvature of at least the second region of the blood vessel differently than the first implant.

9. The method of claim 1, wherein the plurality of first regions having increased radius of curvature comprises at least three regions having increased radius of curvature, and wherein the plurality of second regions having decreased radius of curvature comprises at least three regions having decreased radius of curvature.

10. The method of claim 1, wherein the at least one physiological parameter comprises one or more of a baroreflex response, blood pressure, heart rate, blood vessel impedance, a sympathetic nerve activity, or a nerve activity.

11. The method of claim 1, wherein selecting the implant to provide the therapy based on the detected at least one change in the at least one physiological parameter comprises selecting one implant of a plurality of implants, the selected one implant being suited to affect an optimal therapeutic response.

12. The method of claim 11, wherein the optimal therapeutic response comprises an optimal baroreflex response modification.

13. The method of claim 1, wherein selecting the implant to provide the therapy based on the detected at least one change in the at least one physiological parameter comprises selecting one or more of a size or geometry of the implant.

14. The method of claim 13, wherein the geometry of the implant comprises one or more of a number of vertices or corners of a cross-section of the implant, an orientation of the vertices or corners, or a number of vessel wall contacting struts of the implant.

15. The method of claim 1, wherein the implant comprises an expandable scaffold, the expandable scaffold being configured to alter one or more of a geometry or cross-sectional area of the target region.

16. A method of screening a subject for a therapy, the method comprising:
providing at least one mechanical stimulus to a blood vessel, the at least one mechanical stimulus generating at least a first region of the blood vessel having increased radius of curvature and at least a second region of the blood vessel having decreased radius of curvature, wherein the at least one mechanical stimulus is provided intra-vascularly and wherein providing the at least one mechanical stimulus comprises advancing a mechanical stimulus device through vasculature of the subject to a target location;
detecting at least one change in at least one physiological parameter in response to the provided at least one mechanical stimulus; and
selecting an implant to provide the therapy to the subject based on the detected at least one change in the at least one physiological parameter,
wherein selecting the implant to provide the therapy based on the detected at least one change in the at least one physiological parameter comprises selecting one or more of a size or geometry of the implant, and
wherein the size of the implant comprises a cross-sectional area of the implant and the cross-sectional area of the implant is in a range of $50.0 \text{ mm}^2$ to $60.0 \text{ mm}^2$, $60.0 \text{ mm}^2$ to $70.0 \text{ mm}^2$, $70.0 \text{ mm}^2$ to $80.0 \text{ mm}^2$, $80.0 \text{ mm}^2$ to $90.0 \text{ mm}^2$, $90.0 \text{ mm}^2$ to $100.0 \text{ mm}^2$, $100.0 \text{ mm}^2$ to $110.0 \text{ mm}^2$, $110.0 \text{ mm}^2$ to $120.0 \text{ mm}^2$, or $120.0 \text{ mm}^2$ to $130.0 \text{ mm}^2$.

17. The method of claim 16, wherein the target location is located in a carotid artery, carotid sinus, aorta, aortic arch, subclavian artery, cranial artery, heart, or common artery of the subject.

18. The method of claim 16, wherein the at least the first region of the blood vessel having increased radius of curvature comprises at least one region of the blood vessel with increased strain.

19. The method of claim 16, wherein the at least the second region of the blood vessel having decreased radius of curvature comprises at least one region of the blood vessel with increased strain.

20. The method of claim 16, wherein providing the at least one mechanical stimulus comprises deploying a first implant from the mechanical stimulus device to the target location, the implant increasing the curvature of at least the first region of the blood vessel and decreasing curvature of at least the second region of the blood vessel.

21. The method of claim 20, wherein providing the at least one mechanical stimulus further comprises retracting the first implant from the target location.

22. The method of claim 21, wherein the first implant is retracted from the target location after a time period of between 0 minutes and 1 minute, from 1 minute to 2 minute, from 2 minutes to 3 minutes, from 3 minutes to 4 minutes, from 4 minutes to 5 minutes, from 5 minutes to 10 minutes, from 10 minutes to 20 minutes, from 20 minutes to 30 minutes, from 30 minutes to 1 hour, or from 1 hour to 2 hours.

23. The method of claim 21, wherein providing the at least one mechanical stimulus further comprises deploying a second implant from the mechanical stimulus device to the target location after the retracting the first implant, the second implant increasing the curvature of at least the first region of the blood vessel and decreasing curvature of at least the second region of the blood vessel differently than the first implant.

24. The method of claim 16, wherein at least the first region of the blood vessel having increased curvature comprises a plurality of first regions having increased radius of curvature, wherein at least the second region of the blood vessel having decreased curvature comprises a plurality of second regions having decreased radius of curvature, and wherein the first and second regions alternate with one another around a circumference of the blood vessel.

25. The method of claim 24, wherein the plurality of first regions having increased radius of curvature comprises at least three regions having increased radius of curvature, and wherein the plurality of second regions having decreased radius of curvature comprises at least three regions having decreased radius of curvature.

26. The method of claim 16, wherein the at least one physiological parameter comprises one or more of a baroreflex response, blood pressure, heart rate, blood vessel impedance, a sympathetic nerve activity, or a nerve activity.

27. The method of claim 16, wherein selecting the implant to provide the therapy based on the detected at least one change in the at least one physiological parameter comprises selecting one implant of a plurality of implants, the selected one implant being suited to affect an optimal therapeutic response.

28. The method of claim 27, wherein the optimal therapeutic response comprises an optimal baroreflex response modification.

29. The method of claim 16, wherein the geometry of the implant comprises one or more of a number of vertices or corners of a cross-section of the implant, an orientation of the vertices or corners, or a number of vessel wall contacting struts of the implant.

30. The method of claim 16, wherein the implant comprises an expandable scaffold, the expandable scaffold being configured to alter one or more of a geometry or cross-sectional area of the target region.

* * * * *